(12) United States Patent
Fathi et al.

(10) Patent No.: US 11,633,385 B2
(45) Date of Patent: *Apr. 25, 2023

(54) COMBINATION COMPOSITIONS FOR TREATMENT OF CANCER

(71) Applicant: RedHill Biopharma Ltd., Tel-Aviv (IL)

(72) Inventors: Reza Fathi, Oradell, NJ (US); Dror Ben-Asher, Tel-Aviv (IL); Danielle Abramson, Towaco, NJ (US)

(73) Assignee: RedHill Biopharma Ltd., Tel-Aviv (IL)

( * ) Notice: Subject to any disclaimer, the term of this patent is extended or adjusted under 35 U.S.C. 154(b) by 75 days.

This patent is subject to a terminal disclaimer.

(21) Appl. No.: 17/147,093

(22) Filed: Jan. 12, 2021

(65) Prior Publication Data

US 2021/0128538 A1  May 6, 2021

Related U.S. Application Data

(63) Continuation of application No. 16/573,325, filed on Sep. 17, 2019, now Pat. No. 10,946,000, which is a continuation of application No. 15/805,682, filed on Nov. 7, 2017, now Pat. No. 10,463,654, which is a continuation of application No. 15/287,381, filed on Oct. 6, 2016, now Pat. No. 9,844,540.

(60) Provisional application No. 62/237,925, filed on Oct. 6, 2015.

(51) Int. Cl.

| | | |
|---|---|---|
| *A01N 43/04* | (2006.01) | |
| *A61K 31/70* | (2006.01) | |
| *A61K 31/4409* | (2006.01) | |
| *A61K 31/438* | (2006.01) | |
| *A61P 35/04* | (2006.01) | |
| *A61K 31/7048* | (2006.01) | |
| *A61P 35/00* | (2006.01) | |
| *A61K 31/435* | (2006.01) | |
| *A61K 31/495* | (2006.01) | |
| *A61K 31/498* | (2006.01) | |
| *A61K 45/06* | (2006.01) | |

(52) U.S. Cl.
CPC ........ *A61K 31/4409* (2013.01); *A61K 31/435* (2013.01); *A61K 31/438* (2013.01); *A61K 31/495* (2013.01); *A61K 31/498* (2013.01); *A61K 31/7048* (2013.01); *A61K 45/06* (2013.01); *A61P 35/00* (2018.01); *A61P 35/04* (2018.01)

(58) Field of Classification Search
None
See application file for complete search history.

(56) References Cited

U.S. PATENT DOCUMENTS

| | | |
|---|---|---|
| 5,795,871 A | 8/1998 | Narita et al. |
| 2006/0142305 A1 | 6/2006 | Sperl et al. |
| 2010/0016393 A1 | 1/2010 | DeMattei et al. |
| 2014/0314878 A1 | 10/2014 | Sacchettini et al. |

FOREIGN PATENT DOCUMENTS

| | | |
|---|---|---|
| JP | 2004-536857 A | 12/2004 |
| JP | 2007-513062 A | 5/2007 |
| JP | 2008-546714 A | 12/2008 |
| JP | 2011-511012 | 4/2011 |
| WO | 95/28939 A1 | 11/1995 |
| WO | 2003/007957 A1 | 1/2003 |
| WO | 2006/138660 A2 | 12/2006 |

OTHER PUBLICATIONS

Yamada et al., "An ability to proliferate, infiltrate, and vascularize ovarian cancer cell line for 14, 15-membered macrolide antimicrobial agent", Japan Society of Clinical Oncology, 2000, vol. 35, No. 2, p. 557, p. 956.
Yamada et al., "Effect of Clarithromycin (CAM) on neovascularization and tumor growth of endometrial cancer", Japanese Journal of Cancer Research, article in the Japanese Cancer Associate, the 59th congress (Yokohama), 2000, vol. 91 Supplement, p. 347, 2601.
Heinemann et al., British Journal of Cancer (2013), vol. 108, pp. 766-770.
Beljanski et al., Invest New Drugs (2011), vol. 29, pp. 1132-1142.
Shih et al., Drugs (2014), vol. 74, pp. 1993-2013.

*Primary Examiner* — Patrick T Lewis
(74) *Attorney, Agent, or Firm* — Greenberg Traurig, LLP

(57) ABSTRACT

Provided are methods for treating cancer in a patient by administering at least one antibiotic selected from the group consisting of clofazimine, rifabutin and clarithromycin, in combination with an aryladamantane compound. In an embodiment, the aryladamantane compound is [3-(4-chlorophenyl)-adamantane-1-carboxylic acid (pyridin-4-ylmethyl)amide], or a pharmaceutically acceptable salt thereof.

19 Claims, 17 Drawing Sheets

COMBINATION COMPOSITIONS FOR TREATMENT OF CANCER

RELATED APPLICATION

This application is a continuation of U.S. patent application Ser. No. 16/573,325, filed Sep. 17, 2019, which is a continuation of U.S. patent application Ser. No. 15/805,682, filed Nov. 7, 2017, now U.S. Pat. No. 10,463,654, which is a continuation of U.S. patent application Ser. No. 15/287,381, filed Oct. 6, 2016, now U.S. Pat. No. 9,844,540, which claims the benefit of and priority to U.S. provisional Application Ser. No. 62/237,925, filed Oct. 6, 2015, the entire disclosures of each of which is incorporated by reference in their entirety.

BACKGROUND

Cancer is a group of diseases characterized by the uncontrolled growth and spread of abnormal cells. There are many different types of cancer treatment, including traditional therapies (such as surgery, chemotherapy, and radiation therapy), newer forms of treatment (targeted therapy), and complementary and alternative therapies. It is becoming increasingly evident that cancers are dependent on a number of altered molecular pathways and can develop diverse mechanisms of resistance to therapy with single agents. Therefore, combination regimens may provide the best hope for effective therapies with durable effects.

SUMMARY

Combination therapies for treating cancer are disclosed herein.

In an embodiment, a combination therapy of the present disclosure for treating cancer offers the advantage of having enhanced anti-invasion effects on cancer cells as compared with therapy that only includes administering a single compound of the combination.

In an embodiment, a combination therapy of the present disclosure for treating cancer offers the advantage of having enhanced anti-migration effects on cancer cells as compared with therapy that only includes administering a single compound of the combination.

In an embodiment, a combination therapy of the present disclosure for treating cancer offers the advantage of having enhanced anti-metastatic effects on cancer cells as compared with therapy that only includes administering a single compound of the combination.

In an embodiment, a combination therapy of the present disclosure for treating cancer offers the advantage of having enhanced anti-proliferative effects on cancer cells as compared with therapy that only includes administering a single compound of the combination. In an embodiment, the enhanced anti-proliferation effects on cancer cells is a result of one or more of the compounds ability to decrease or stop the production of, or overexpression of, cytokines in the tumor cells, stromal cells, or both. In an embodiment, the cytokine affected by the compound is interleukin-6 (IL-6).

In an embodiment, each agent of the present invention alone is capable of at least one of anti-invasion effects, anti-migration effects, anti-metastatic effects, anti-proliferative effects, and apoptosis, and the combination of two or more agents of the present invention synergistically inhibit cell growth and increase apoptosis.

It is contemplated that a combination therapy of the present disclosure can provide synergistic benefits in cytotoxicity. For instance, the cytotoxicity of the combination treatment can be superior to the additive effect of the individual treatment of the compounds administered alone. Additionally, or alternatively, a combination therapy of the present disclosure can provide acceptable cytotoxicity, but at a reduce dosage of the individual treatment of the compounds alone. This can result in less adverse side effects during the treatment protocol, but with the same or better efficacy toward the cancer being treated.

In an embodiment, a pharmaceutical composition of the present invention comprises a first agent in combination with at least a second agent selected from the agents of Table 1, or an analog thereof, and a pharmaceutically acceptable carrier or diluent. Potential combinations of anticancer agents include a variety of permutations of agents selected from Table 1 with/without standards of care (e.g., chemotherapy, targeted agents, and immunomodulators).

The methods of the present invention include administering to a patient a first agent in combination with a second agent selected from the agents of Table 1, or an analog thereof, in an amount that is effective to treat the patient. In an embodiment, the method further includes administering a third agent selected from the agents of Table 1. In an embodiment, the method further includes administering a fourth agent selected from the agents of Table 1. In an embodiment, the method further includes administering a fifth agent selected from the agents of Table 1. In an embodiment, the method further includes administering a sixth agent selected from the agents of Table 1. In some embodiments, the methods of the present invention include administering to a patient two agents selected from the agents of Table 1, or analogs thereof, in an amount that is effective to treat the patient. In some embodiments, the methods of the present invention include administering to a patient three agents selected from the agents of Table 1, or analogs thereof, in an amount that is effective to treat the patient. In some embodiments, the methods of the present invention include administering to a patient four agents selected from the agents of Table 1, or analogs thereof, in an amount that is effective to treat the patient. In some embodiments, the methods of the present invention include administering to a patient five agents selected from the agents of Table 1, or analogs thereof, in an amount that is effective to treat the patient. In some embodiments, the methods of the present invention include administering to a patient six agents selected from the agents of Table 1, or analogs thereof, in an amount that is effective to treat the patient. In the present disclosure, the inventors have found that clinical combination of two or more of the agents listed in Table 1 may act as a more potent version of a single drug alone. In some embodiments, the desired effect(s) of combinations of anticancer agents listed in Table 1, including a variety of permutations of agents selected from Table 1, is significantly higher than the effect of each single agent administered alone. A combination therapy of the present disclosure might be hypothesized to interact in two general ways: (a) one agent may reinforce the action of another agent, or (b) the two drugs may combine to exert effects that are distinct from either individual compound.

In an embodiment, a method of limiting the growth and proliferation of pancreatic cancer in a patient having or suspected of having pancreatic cancer comprises co-administrating to the patient at least two drugs from Table 1, the amounts of the drugs in combination, being effective for achieving the limiting of growth and proliferation of cancerous cells. In an embodiment, the administration is concurrent. In an embodiment, the administration is sequential.

According to aspects illustrated herein, there is disclosed a combination cancer therapy that includes administering effective amounts of two or more of rifabutin, clofazimine and clarithromycin to a patient in need of such treatment. In an embodiment, effective amounts of rifabutin, clofazimine and clarithromycin are administered to a cancer patient expressing higher than normal levels of IL-6 in their serum and, after an effective treatment period with rifabutin, clofazimine and clarithromycin, the serum concentration of IL-6 in the patient has diminished from the initial level to result in the reduction or ablation of cancer progression.

According to aspects illustrated herein, there is disclosed a combination cancer therapy that includes at least one antibiotic selected from the group consisting of rifabutin, clofazimine and clarithromycin, with at least one or more of a serine protease inhibitor, a nucleoside analogue or a sphingosine kinase inhibitor. In an embodiment, the serine protease inhibitor is upamostat. In an embodiment, the nucleoside analogue is brivudine. In an embodiment, the sphingosine kinase inhibitor is an aryladamantane compound.

According to aspects illustrated herein, a method for treating a patient having cancer includes administering at least one of clofazimine, rifabutin, or clarithromycin, in combination with at least one of upamostat, brivudine or an aryladamantane compound to a subject in need of such treatment. In an embodiment, the method of administering includes administering to the patient therapeutically effective amounts of agents multiple times per day to reach therapeutic efficacy dosages. In an embodiment, the therapeutically effective amount of clarithromycin is from about 95 mg to about 1000 mg daily. In an embodiment, clarithromycin is administered orally as a solid dosage form one or more times per day. In an embodiment, the therapeutically effective amount of clarithromycin is up to 1 gram daily for an adult. In an embodiment, two doses of 500 mg clarithromycin are administered as an IV infusion, using a solution concentration of about 2 mg/ml. 1 gram daily of clarithromycin can be administered as an IV infusion for a period of from two days to five days. In an embodiment, 1 gram daily of clarithromycin can be administered as an IV infusion for a period of three days. In an embodiment, the therapeutically effective amount of rifabutin is from about 45 mg to about 450 mg daily. In an embodiment, rifabutin is administered orally as a solid dosage form one or more times per day. In an embodiment, the therapeutically effective amount of clofazimine is from about 10 mg to about 1000 mg daily. In an embodiment, clofazimine is administered orally as a solid dosage form one or more times per day. Brivudine can be administered as an active metabolite, a salt, or in protected or in prodrug form. In an embodiment, a therapeutically effective amount of BVDU is up to 600 mg/day. In an embodiment, the 600 mg is administered once daily as a single oral dosage form. In an embodiment, the 600 mg is administered as a 150 mg single oral dosage form taken four times daily. In an embodiment, a therapeutically effective amount of BVDU is up to 500 mg/day for an adult. In an embodiment, the 500 mg is administered once daily as a single oral dosage form. In an embodiment, the 500 mg is administered as a 125 mg single oral dosage form taken four times daily. In an embodiment of the present disclosure, upamostat is administered orally at a dose of about 0.5 mg/kg to about 1.1 mg/kg. In an embodiment, upamostat is administered orally at a daily dose of between about 200 mg to 400 mg. In an embodiment, upamostat is administered orally at a daily dose of between about 150 mg to 550 mg. In an embodiment, upamostat is administered orally at a daily dose of between about 200 mg to 550 mg. In an embodiment, upamostat is administered orally at a daily dose of between about 250 mg to 550 mg. In an embodiment, upamostat is administered orally at a daily dose of between about 300 mg to 550 mg. In an embodiment, upamostat is administered orally at a daily dose of between about 350 mg to 550 mg. In an embodiment, upamostat is administered orally at a daily dose of between about 400 mg to 550 mg. In an embodiment, upamostat is administered orally at a daily dose of between about 450 mg to 550 mg. In an embodiment, upamostat is administered orally at a daily dose of between about 500 mg to 550 mg. In an embodiment, upamostat is administered orally at a daily dose of between about 200 mg to 550 mg. In an embodiment, upamostat is administered orally at a daily dose of between about 200 mg to 500 mg. In an embodiment, upamostat is administered orally at a daily dose of between about 200 mg to 450 mg. In an embodiment, upamostat is administered orally at a daily dose of between about 200 mg to 350 mg. In an embodiment, upamostat is administered orally at a daily dose of between about 200 mg to 300 mg. In an embodiment, upamostat is administered orally at a daily dose of between about 200 mg to 250 mg. In an embodiment, upamostat is administered orally at a daily dose of between about 500 mg to 1000 mg. In an embodiment, upamostat is administered orally at a daily dose of between about 750 mg to 1000 mg. In an embodiment, upamostat is administered orally at a daily dose of between about 500 mg to 750 mg. In an embodiment, the therapeutically effective amount of aryladamantane compound is 0.5 grams to 3.5 grams daily. In an embodiment, the aryladamantane compound is administered orally at a daily dose of 1.5 grams daily. In an embodiment, the aryladamantane compound is administered orally at a daily dose of 2.0 grams daily. In an embodiment, the aryladamantane compound is administered orally at a daily dose of 2.5 grams daily. In an embodiment, the aryladamantane compound is administered orally at a daily dose of 3.0 grams daily.

In an embodiment, a combination of the present disclosure includes a compound of Structure (I)

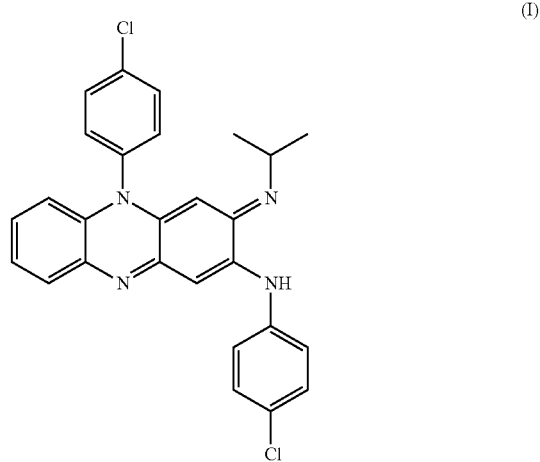 [SMILES: CC(C)/N=c1\cc2n(-c3ccc(Cl)cc3)c3ccccc3nc-2cc1Nc1ccc(Cl)cc1]

or a pharmaceutically acceptable salt thereof; and a compound of Structure (II)

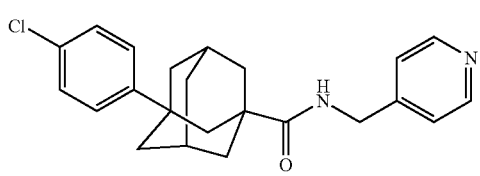

3-(4-Chloro-phenyl)-adamantane-1-carboxylic acid (pyridin-4-ylmethyl)-amide or a pharmaceutically acceptable salt thereof. In an embodiment, the combination further comprises a compound of Structure (III)

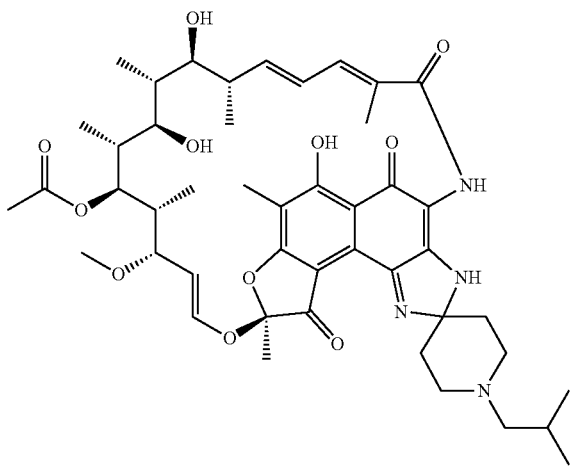

or a pharmaceutically acceptable salt thereof. In an embodiment, the combination further includes a compound of Structure (IV)

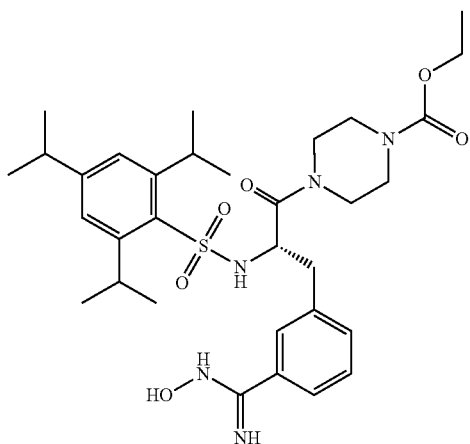 [SMILES: CCOC(=O)N1CCN(C(=O)[C@H](Cc2cccc(C(=N)NO)c2)NS(=O)(=O)c2c(C(C)C)cc(C(C)C)cc2C(C)C)CC1]

or a pharmaceutically acceptable salt thereof.

In an embodiment, a method for treating cancer, or preventing cancer recurrence or progression in a human in need thereof includes administering to a human, concurrently or sequentially, a therapeutically effective amount of at least one antibiotic, and an aryladamantane compound.

BRIEF DESCRIPTION OF THE FIGURES

FIG. 2A shows the median relative tumor volumes as a function of time; FIG. 2B shows individual relative tumor volumes on day 28 (day of min. T/C value) (including LOCF values).

FIG. 3A shows the median relative tumor volumes as a function of time; FIG. 3B shows individual relative tumor volumes on day 28 (day of min. T/C value) (including LOCF values).

FIG. 4A shows the median relative tumor volumes as a function of time; FIG. 4B shows individual relative tumor volumes on day 28 (day of min. T/C value) (including LOCF values).

FIG. 5A shows the median relative tumor volumes as a function of time; FIG. 5B shows individual relative tumor volumes on day 28 (day of min. T/C value) (including LOCF values).

DETAILED DESCRIPTION

Figure 1:
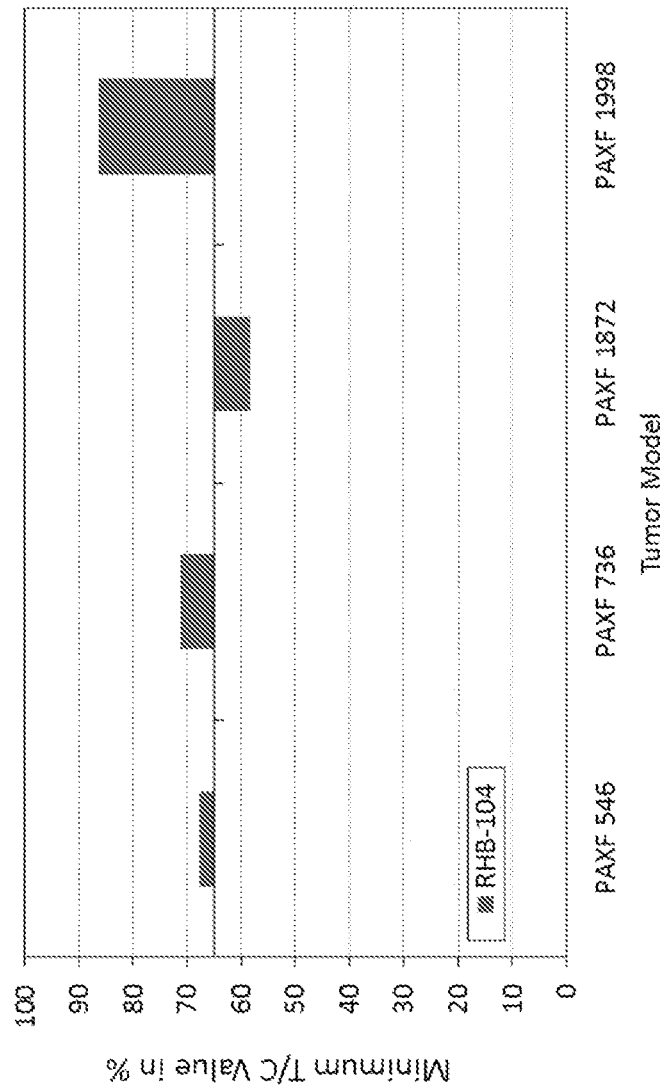
FIG. 1 shows the efficacy of RHB-104 in monotherapy in four tumor models. Shown are the minimum T/C values for all experiments. As a turning point, a minimum T/C value of 65% (upper limit for borderline anti-tumor efficacy) was chosen.
Figure 2A:
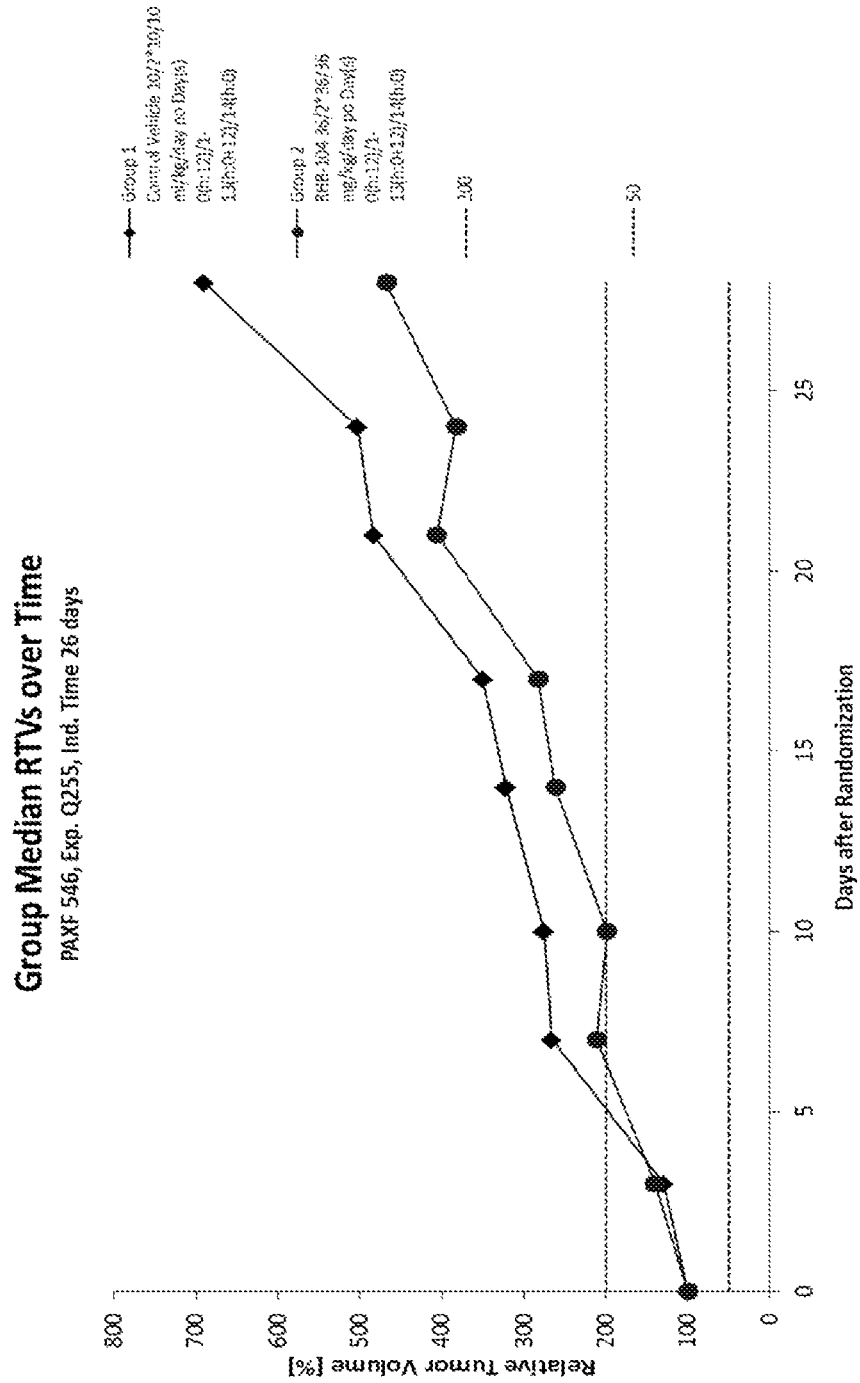
FIGS. 2A and 2B show the anti-tumor efficacy of RHB-104 in monotherapy (PDX: PAXF 546).
Figure 2B:
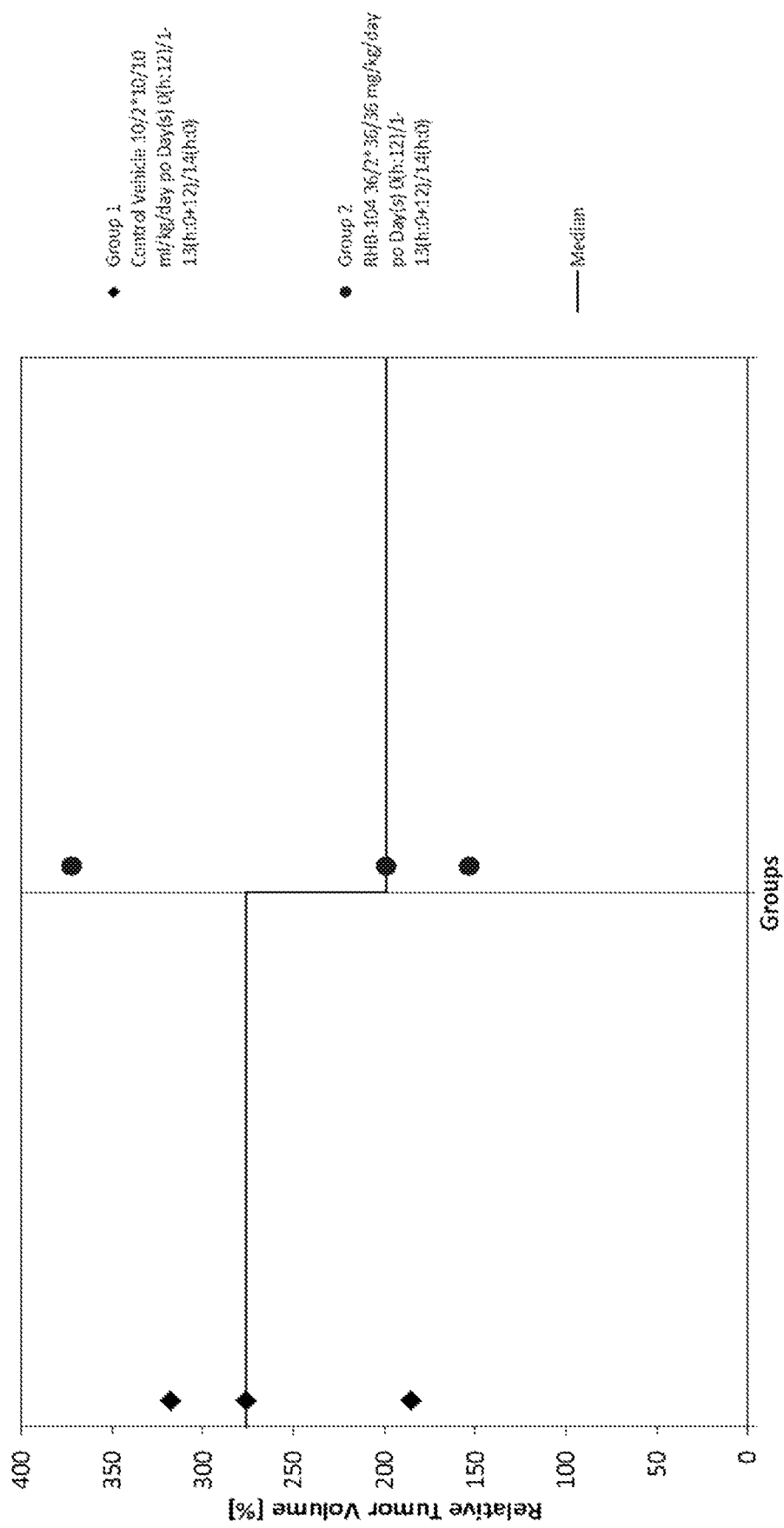
Figure 3A:
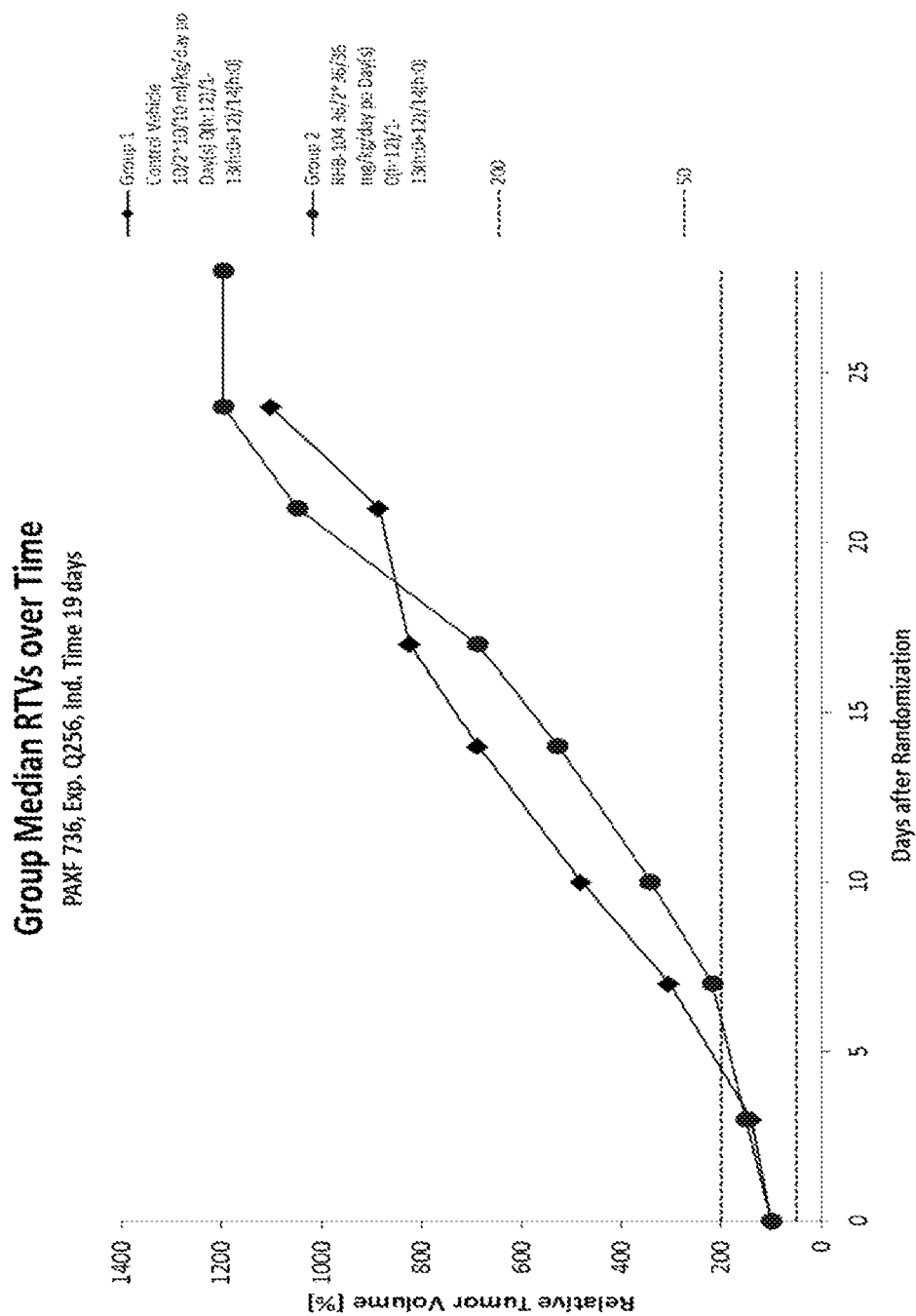
FIGS. 3A and 3B show the anti-tumor efficacy of RHB-104 in monotherapy (PDX: PAXF 736).
Figure 3B:
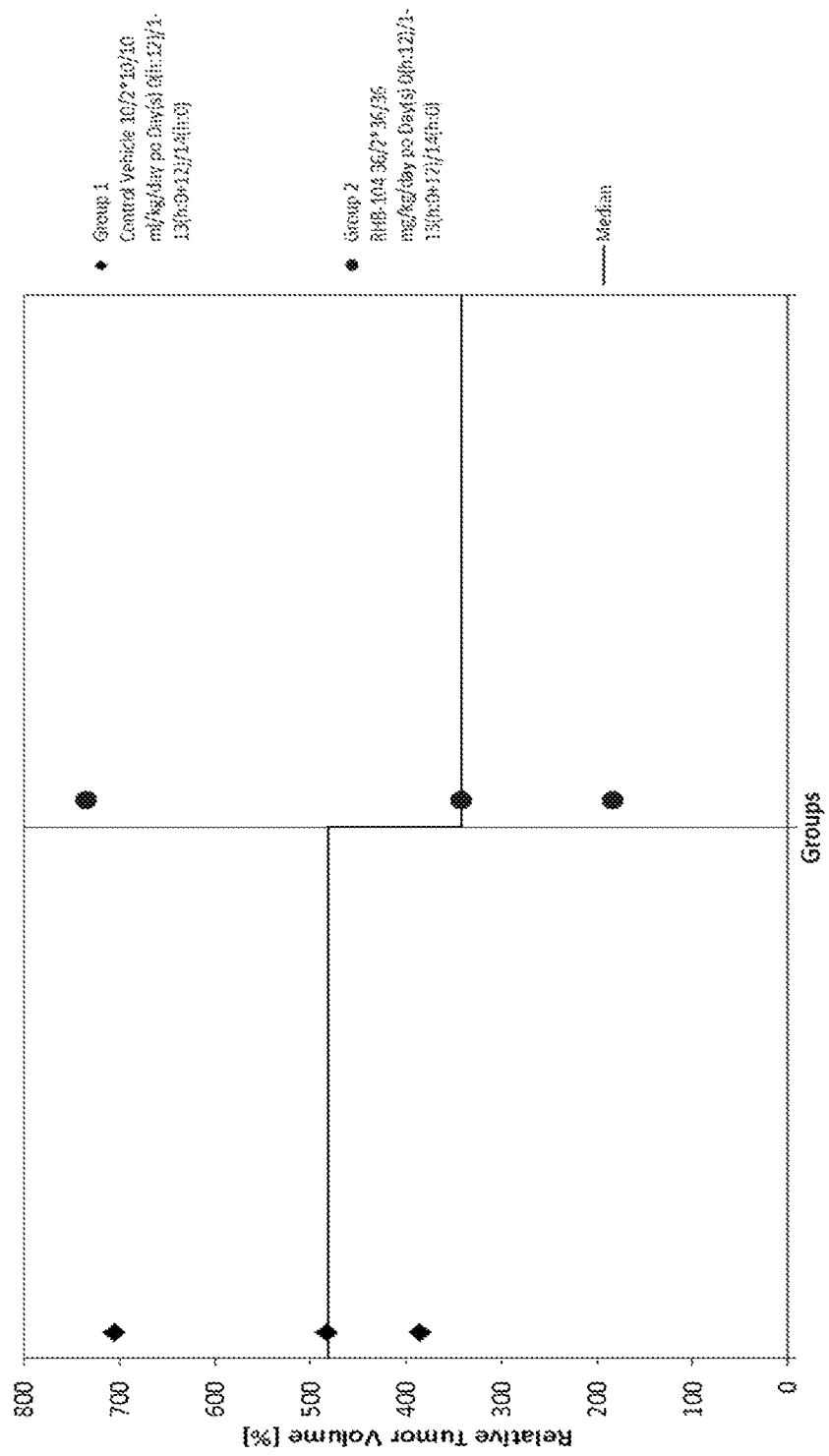
Figure 4A:
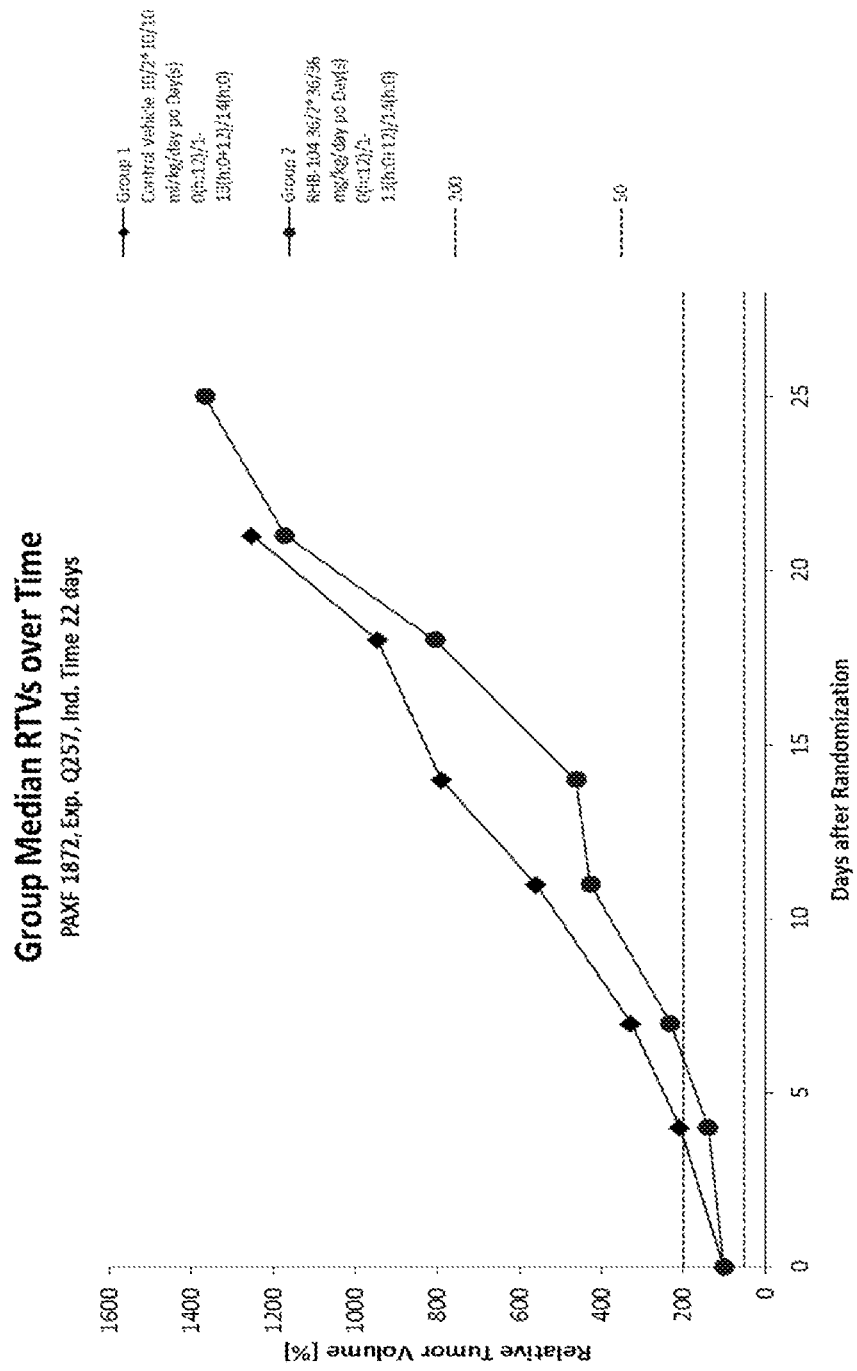
FIGS. 4A and 4B show the anti-tumor efficacy of RHB-104 in monotherapy (PDX: PAXF 1872).
Figure 4B:
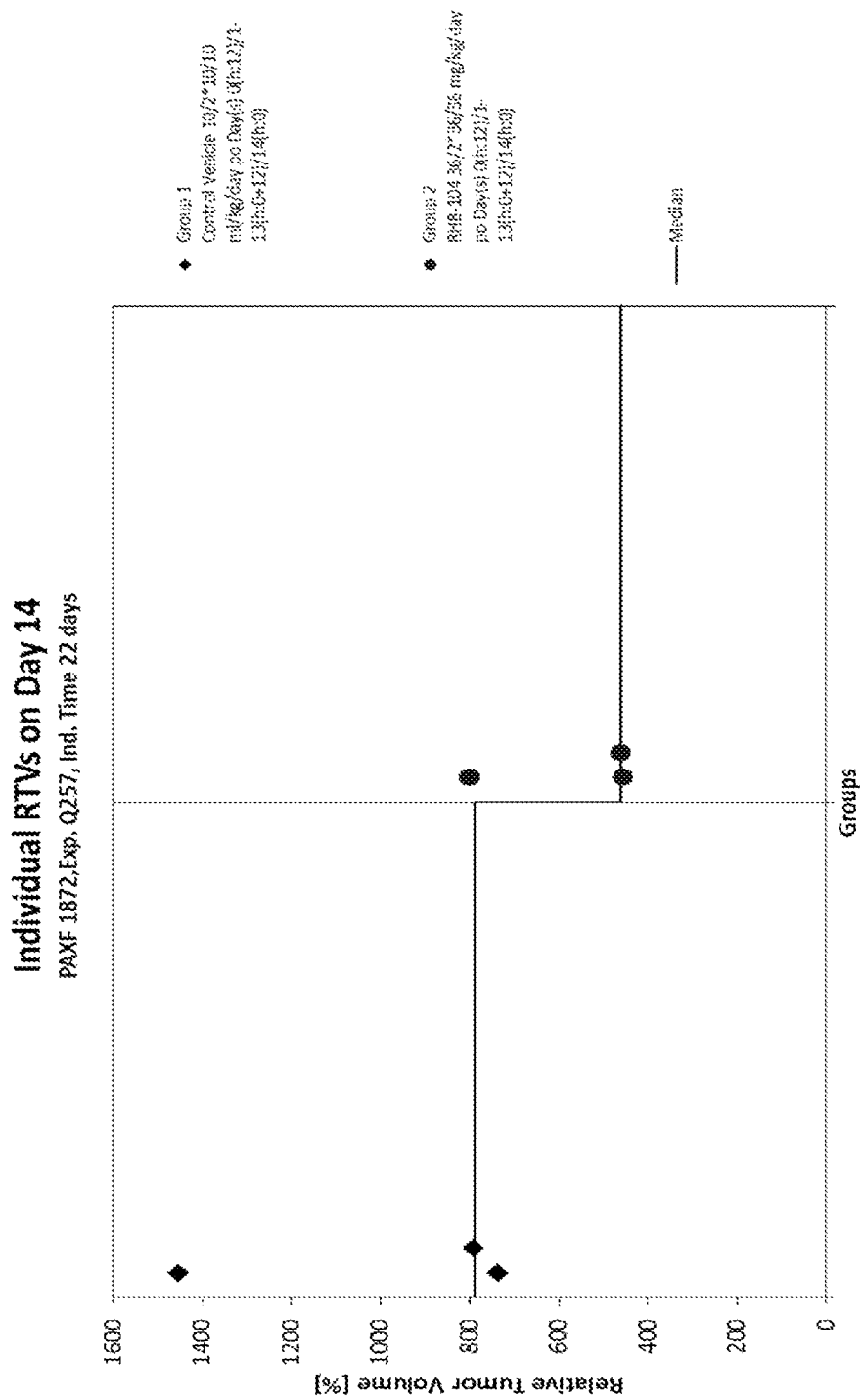
Figure 5A:
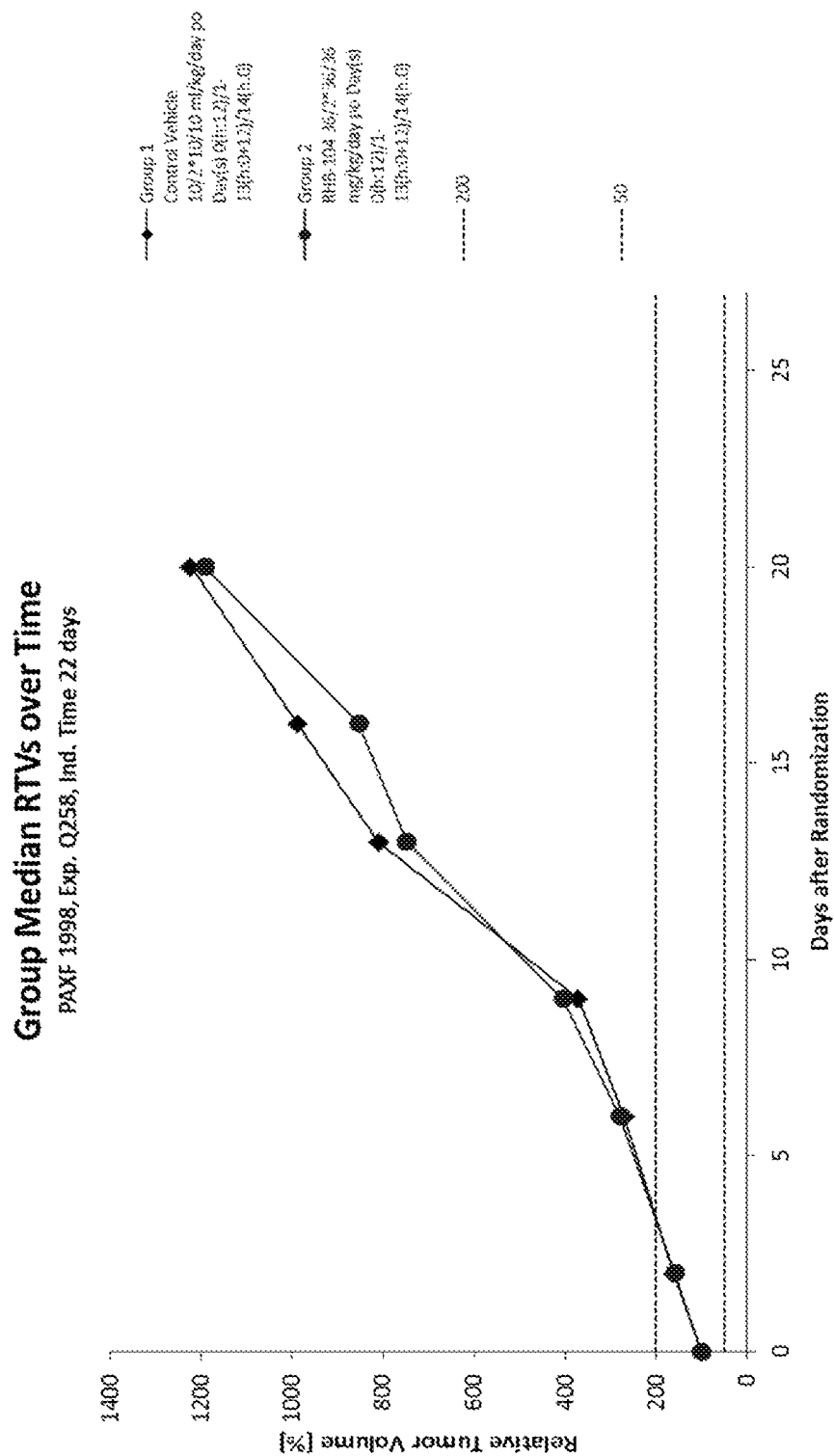
FIGS. 5A and 5B show the anti-tumor efficacy of RHB-104 in monotherapy (PDX: PAXF 1998).
Figure 5B:
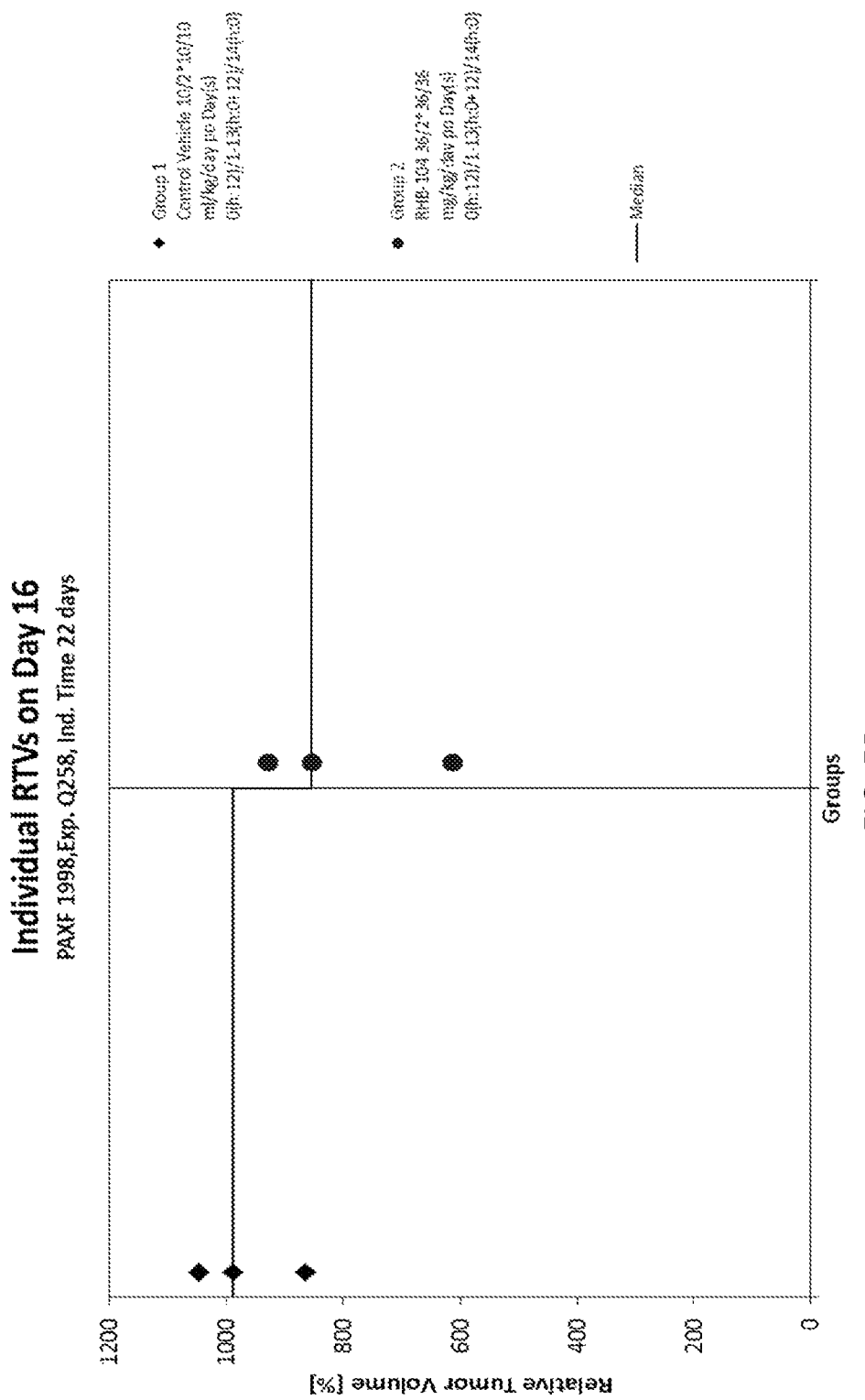

As used herein, the term "agent" refers to a compound having a pharmacological activity or effect on a patient. The terms "agent," "active ingredient," "compound," and "drug" are used interchangeably herein.

The term "administration" or "administering" includes routes of introducing the compounds of the invention to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, and rectal by suppositories. Oral administration is preferred. The injection can be bolus or can be continuous infusion. Depending on the route of administration, the compounds of the invention can be coated with or disposed in a selected material to protect it from natural conditions which may detrimentally effect its ability to perform its intended function. The compounds of the invention can be administered in conjunction with a pharmaceutically-acceptable carrier. Furthermore, the compounds of the invention can also be administered in a pro-drug form which is converted into its active metabolite, or more active metabolite in vivo.

"Apoptosis" (programmed cell death) is a process that plays an important role in preventing cancer and in the treatment of cancer by using agents that induce apoptosis of abnormal cancer cells. In an embodiment, an agent or agents of the present invention have the ability to induce apoptosis in an individual. Several in vitro assays can be used to test the efficacy of an agent of the present disclosure to induce apoptosis including, but not limited to, flow cytometry selected from one of plasma membrane, mitochondrial, caspase, nuclear apoptosis, and multiparametric apoptosis; microscopy selected from one of caspase activity, DNA fragmentation and morphology, annexin V staining, membrane potential and other mitochondrial assays; high-content analysis; and microplate assay such as a population-based assay for measuring caspase activity.

As used herein, the term "anti-invasion effects" means the ability of an agent or agents of the present invention to prevent cancer invasion or to reduce the incidence of tumor invasion in an individual. In an embodiment, an agent or agents of the present invention reduces the incidence of tumor invasion in an individual by about 1% to about 99.0% as compared to an existing drug known to have anti-invasion effects. In an embodiment, an agent or agents of the present invention reduces the incidence of tumor invasion in an individual by about 5% to about 95.0% as compared to an existing drug known to have anti-invasion effects. In an embodiment, an agent or agents of the present invention reduces the incidence of tumor invasion in an individual by about 10% to about 90.0% as compared to an existing drug known to have anti-invasion effects. In an embodiment, an agent or agents of the present invention reduces the incidence of tumor invasion in an individual by about 20% to about 80.0% as compared to an existing drug known to have anti-invasion effects. In an embodiment, an agent or agents of the present invention reduces the incidence of tumor invasion in an individual by about 30% to about 70.0% as compared to an existing drug known to have anti-invasion effects. In an embodiment, an agent or agents of the present invention reduces the incidence of tumor invasion in an individual by about 40% to about 60.0% as compared to an existing drug known to have anti-invasion effects. In an embodiment, an agent or agents of the present invention reduces the incidence of tumor invasion in an individual by about 50% as compared to an existing drug known to have anti-invasion effects.

As used herein, the term "anti-migration effects" means the ability of an agent or agents of the present invention to prevent cancer cell migration or to reduce the incidence of tumor cell migration in an individual once tumor cells acquire the ability to penetrate the surrounding tissues, the process of invasion is instigated as these moving cells pass through the basement membrane and extracellular matrix, progressing to intravasation as they penetrate the lymphatic or vascular circulation. The metastatic cells then journey through the circulatory system invading the vascular basement membrane and extracellular matrix in the process of extravasation. Ultimately, these cells will attach at a new location and proliferate to produce the secondary tumor. In an embodiment, an agent or agents of the present invention reduces the incidence of tumor cell migration in an individual by about 1% to about 99.0% as compared to an existing drug known to have anti-migration effects. In an embodiment, an agent or agents of the present invention reduces the incidence of tumor cell migration in an individual by about 5% to about 95.0% as compared to an existing drug known to have anti-migration effects. In an embodiment, an agent or agents of the present invention reduces the incidence of tumor cell migration in an individual by about 10% to about 90.0% as compared to an existing drug known to have anti-migration effects. In an embodiment, an agent or agents of the present invention reduces the incidence of tumor cell migration in an individual by about 20% to about 80.0% as compared to an existing drug known to have anti-migration effects. In an embodiment, an agent or agents of the present invention reduces the incidence of tumor cell migration in an individual by about 30% to about 70.0% as compared to an existing drug known to have anti-migration effects. In an embodiment, an agent or agents of the present invention reduces the incidence of tumor cell migration in an individual by about 40% to about 60.0% as compared to an existing drug known to have anti-migration effects. In an embodiment, an agent or agents of the present invention reduces the incidence of tumor cell migration in an individual by about 50% as compared to an existing drug known to have anti-migration effects.

As used herein, the term "anti-metastatic effects" means the ability of an agent or agents of the present invention to prevent, or reduce the incidence of, at least one of the following steps in the metastatic process: (1) detachment of cancer cells from the primary site, (2) induction and invasion into new blood vessels, (3) exiting from the blood circulation, and (4) establishment of a new colony at distant sites. In an embodiment, an agent or agents of the present invention reduces the incidence of one of the steps in the metastatic process in an individual by about 1% to about 99.0% as compared to an existing drug known to have anti-metastatic effects. In an embodiment, an agent or agents of the present invention reduces the incidence of one of the steps in the metastatic process in an individual by about 5% to about 95.0% as compared to an existing drug known to have anti-metastatic effects. In an embodiment, an agent or agents of the present invention reduces the incidence of one of the steps in the metastatic process in an individual by about 10% to about 90.0% as compared to an existing drug known to have anti-metastatic effects. In an embodiment, an agent or agents of the present invention reduces the incidence of one of the steps in the metastatic process in an individual by about 20% to about 80.0% as compared to an existing drug known to have anti-metastatic effects. In an embodiment, an agent or agents of the present invention reduces the incidence of one of the steps in the metastatic process in an individual by about 30% to about 70.0% as compared to an existing drug known to have anti-metastatic effects. In an embodiment, an agent or agents of the present invention reduces the incidence of one of the steps in the metastatic process in an individual by about 40% to about 60.0% as compared to an existing drug known to have anti-metastatic effects. In an embodiment, an agent or agents of the present invention reduces the incidence of one of the steps in the metastatic process in an individual by about 50% as compared to an existing drug known to have anti-metastatic effects. Several in vitro assays can be used to test the efficacy of an agent of the present disclosure to prevent or delay metastatic progression including, but not limited to, scratch or wound healing assays, trans-membrane migration assays (Modified Boyden chamber), gap-closure or exclusion zone assays as well as migration assays using microfluidic devices (MFDs).

As used herein the term "neoplasm" refers to an abnormal growth of cells or tissue and is understood to include benign, i.e., non-cancerous growths, and malignant, i.e., cancerous growths. The term "neoplastic" means of or related to a neoplasm. The term "anti-neoplastic agent" is understood to mean a substance producing an anti-neoplastic effect in a tissue, system, animal, mammal, human, or other subject.

As used herein, the term "anti-proliferative effects" means the ability of an agent or agents of the present invention to inhibit cancer cell growth and cell division or to reduce the incidence of cancer cell growth and cell division in an individual. In an embodiment, an agent of the present invention results in an anti-proliferative effect by affecting cytokine production. In an embodiment, an agent or agents of the present invention reduces the incidence of cancer cell growth and cell division in an individual by about 1% to about 99.0% as compared to an existing drug known to have anti-proliferative effects. In an embodiment, an agent or agents of the present invention reduces the incidence of cancer cell growth and cell division in an individual by about 5% to about 95.0% as compared to an existing drug known to have anti-proliferative effects. In an embodiment, an agent or agents of the present invention reduces the incidence of cancer cell growth and cell division in an individual by about 10% to about 90.0% as compared to an existing drug known to have anti-proliferative effects. In an embodiment, an agent or agents of the present invention reduces the incidence of cancer cell growth and cell division in an individual by about 20% to about 80.0% as compared to an existing drug known to have anti-proliferative effects. In an embodiment, an agent or agents of the present invention reduces the incidence of cancer cell growth and cell division in an individual by about 30% to about 70.0% as compared to an existing drug known to have anti-proliferative effects. In an embodiment, an agent or agents of the present invention reduces the incidence of cancer cell growth and cell division in an individual by about 40% to about 60.0% as compared to an existing drug known to have anti-proliferative effects. In an embodiment, an agent or agents of the present invention reduces the incidence of cancer cell growth and cell division in an individual by about 50% as compared to an existing drug known to have anti-proliferative effects. Several in vitro assays can be used to test the efficacy of an agent of the present disclosure to prevent or delay cell growth and cell division including, but not limited to, cell proliferation assays that measure DNA synthesis, cell proliferation assays that measure metabolic activity, cell proliferation assays that measure antigens associated with cell proliferation, and cell proliferation assays that measure ATP concentration.

The term "cytokine" refers to functional small peptides which under physiological conditions control the cell-to-cell communication within the various body tissues. Cytokines are also called interleukins, monokines, lymphokines, chemokines and growth factors. It has been observed that the local tissue or circulating cytokine levels is altered in a number of cancers, which may affect the development/advancement, treatment and prognosis. Elevated cytokine levels, for example, have been associated with reducing the anti-cancer activity of various treatments. Cytokines have also been demonstrated to exacerbate the toxic effects of chemotherapy and affect drug metabolism. Inflammatory cytokines such as interferons and interleukins produced in the tumor microenvironment play a role in stimulation or inhibition of disease progression.

Diseases that can be treated using the compounds of the present invention include, but are not limited to cancers, such as cancerous tumors. "Cancer" is meant to refer to any disease that is caused by or results in inappropriately high levels of cell division, inappropriately low levels of apoptosis, or both. In an embodiment, the cancer is a result of an infectious disease, such as a viral infection. In an embodiment, the cancer is a result of an infectious disease, such as a bacterial or parasitic infection. In an embodiment, the cancer is caused by a gene mutation. Cancers that can be treated include, but are not limited to, breast cancer, pancreatic cancer, kidney cancer, colon cancer, rectal cancer, ovarian cancer, stomach cancer, uterine cancer, carcinoma in situ, and leukemia.

As used herein, the term "pancreatic cancer" refers to any cancer having its origin in pancreas cells, and includes metastatic and local forms of pancreatic cancer. In 2012, pancreatic cancers of all types were the seventh most common cause of cancer deaths, resulting in 330,000 deaths globally. In the United States, pancreatic cancer is the fourth most common cause of deaths due to cancer. In certain embodiments, a particular subpopulation of patients with pancreatic cancer can be treated according to combination therapies of this invention. The combination of agents of the invention may be utilized to enhance the efficacy and a reduction in the required amount of either agent to achieve the efficacy.

A "patient" refers to any animal, such as a primate, such as a human. Any animal can be treated using the methods and composition of the present invention.

As used herein, the term "a suitable period of time" refers to the period of time starting when a subject begins treatment for a diagnosis of cancer using a method of the present disclosure, throughout the treatment, and up until when the subject stops treatment. In an embodiment, a suitable period of time is one (1) week. In an embodiment, a suitable period of time is between one (1) week and two (2) weeks. In an embodiment, a suitable period of time is two (2) weeks. In an embodiment, a suitable period of time is between two (2) weeks and three (3) weeks. In an embodiment, a suitable period of time is three (3) weeks. In an embodiment, a suitable period of time is between three (3) weeks and four (4) weeks. In an embodiment, a suitable period of time is four (4) weeks. In an embodiment, a suitable period of time is between four (4) weeks and five (5) weeks. In an embodiment, a suitable period of time is five (5) weeks. In an embodiment, a suitable period of time is between five (5) weeks and six (6) weeks. In an embodiment, a suitable period of time is six (6) weeks. In an embodiment, a suitable period of time is between six (6) weeks and seven (7) weeks. In an embodiment, a suitable period of time is seven (7) weeks. In an embodiment, a suitable period of time is between seven (7) weeks and eight (8) weeks. In an embodiment, a suitable period of time is eight (8) weeks.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

By "an effective amount" or "a therapeutically effective amount" is meant the amount of a compound, alone or in combination with another therapeutic regimen, required to treat a patient with caner in a clinically relevant manner. This amount will achieve the goal of reducing or eliminating the disease or disorder. A sufficient amount of an active compound used to practice the present invention for therapeutic treatment of conditions caused by cancer varies depending upon the manner of administration, the age, body weight, and general health of the patient. Ultimately, the prescribers will decide the appropriate amount and dosage regimen. In a combination therapy of the invention, the effective amount of an agent may be less than the effective amount if the agent were administered in a non-combinatorial (single-agent) therapy. Additionally, an effective amount may be an amount of an agent in a combination therapy of the invention that is safe and efficacious in the treatment of a patient having cancer over each agent alone as determined and approved by a regulatory authority (such as the U.S. Food and Drug Administration).

By "more effective" is meant that a treatment exhibits greater efficacy, or is less toxic, safer, more convenient, or less expensive than another treatment with which it is being compared. Efficacy may be measured by a skilled practitioner using any standard method that is appropriate for a given indication.

The term "minimize" or "reduce," or a derivative thereof, includes a complete or partial inhibition of a specified biological effect (which is apparent from the context in which the term minimize is used).

The term "modulate" refers to an increase or decrease, e.g., in the ability of a cell to proliferate in response to exposure to compounds of the invention, e.g., the inhibition of proliferation of at least a sub-population of cells in an animal such that a desired end result is achieved, e.g., a therapeutic result. In an embodiment, the modulation is an inhibition. The term "inhibition" means decrease, suppress, attenuate, diminish, arrest, or stabilize the target activity, e.g., cell proliferation.

The term "combination therapy" means the administration of two or more agents of the present invention to treat cancer. In an embodiment, each of the agents targets different parts of the cancer cell's signaling pathway. In an embodiment, each of the agents targets the cancer cell's relationship to the tissue environment. In an embodiment, one agent targets the cancer cell's signaling pathway and one agent targets the cancer cell's relationship to the tissue environment. Such administration encompasses co-administration of these agents in a substantially simultaneous manner, such as in a single capsule having a fixed ratio of active ingredients ("fixed-dose") or in multiple, separate capsules or tablets for each active ingredient. In addition, such administration also encompasses use of each type of agent in a sequential manner. In either case, the treatment regimen will provide beneficial effects of the drug combination in treating the conditions or disorders described herein. In an embodiment, a combination therapy of the present invention includes at least one fixed-dose combination of two or more agents. A fixed-dose provides the advantages of combination therapy while reducing the number of prescriptions and administrative costs. In an embodiment, a combination therapy of the present disclosure uses lower concentrations of each drug due to synergistic or additive effects. In an embodiment, the use of lower concentrations of each drug (as compared with a monotherapy approach of the drug) leads to reduced adverse events and a higher therapeutic ratio or index.

"Concurrently" means (1) simultaneously in time, or (2) at different times during the course of a common treatment schedule.

"Sequentially" refers to the administration of one active agent used in the method followed by administration of another active agent. After administration of one active agent, the next active agent can be administered substantially immediately after the first, or the next active agent can be administered after an effective time period after the first active agent; the effective time period is the amount of time given for realization of maximum benefit from the administration of the first active agent.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, by administration of separate pills or capsules, or by separate infusions. In general, during alternation therapy, an effective dosage of each active ingredient is administered sequentially, i.e., serially, whereas in combination therapy, effective dosages of two or more active ingredients are administered together.

The agents of the present invention are expected to be particularly useful as part of a combination therapy with existing standard of care for the treatment of cancer. In an embodiment, a combination therapy of the present disclosure includes administering at least two agents of the present invention and further co-administering the agents of the invention with standard of care chemotherapeutic agents. In an embodiment, a combination therapy of the present disclosure includes surgical removal of the affected tissue, administering at least two agents of the present invention, and further co-administering the agents of the invention with standard of care chemotherapy or radiation treatments. Current standard of care chemotherapeutic agents include, but are not limited to, antiangiogenic agents; cytostatic agents; and antiproliferative/antineoplastic agents and combinations thereof. For example, antineoplastic agents and combinations of agents used in managing pancreatic carcinoma include, but are not limited to, gemcitabine, gemcitabine/docetaxel/capecitabine, gemcitabine/capecitabine, gemcitabine/albumin-bound paclitaxel, 5-fluorouracil (5-FU), LV5-FU/oxaliplatin/irinotecan, paclitaxel/gemcitabine, erlotinib, erlotinib/gemcitabine and capecitabine, alone or in combination. Such agents have been shown to prolong survival in pancreatic cancer. In an embodiment at least two agents of the present invention are further co-administered with one or more of these standards of care chemotherapeutic agents.

In an embodiment, a combination therapy of the present disclosure includes administering at least two agents of the present invention and further co-administering the agents of the invention with an immunomodulator. Immunomodulators are the active agents used in immunotherapy, which modify the immune response of the immune system and can comprise a diverse array of recombinant, synthetic and natural preparations. Examples of immunomodulators include, but are not limited to, interleukins, cytokines, chemokines, and immunomodulatory imide drugs.

In an embodiment, a combination therapy of the present disclosure includes administering at least two agents of the present invention and further co-administering the agents of the invention with an immune checkpoint inhibitor. Drugs or drug candidates that inhibit/block the inhibitory checkpoint molecules are known as immune checkpoint inhibitors.

In an embodiment, a combination therapy of the present disclosure includes administering at least two agents of the present invention and further co-administering the agents of the invention with a matrix metalloproteinase inhibitor (MMPI). MMPIs inhibit cell migration and have potential antiangiogenic effects. Examples of MMPIs include exogenous MMPIs, including, but not limited to, tanomastat, prinomastat, batimastat and marimastat.

The terms "co-administering" or "co-administration" are intended to encompass simultaneous or sequential administration of therapies. For example, co-administration may include administering both a nucleoside analogue of the present invention and a serine protease inhibitor in a single composition. It may also include simultaneous administration of a plurality of such compositions. Alternatively, co-administration may include administration of a plurality of such compositions at different times during the same period.

The term "analog" of an agent or other chemical moiety includes, but is not limited to, compounds that are structurally similar to the agent or are in the same general chemical class as the agent or. The analog of the agent retains similar chemical and/or physical property (including, for example, functionality) of the agent.

The phrase "pharmaceutically-acceptable carrier" includes pharmaceutically-acceptable material, composition or vehicle, such as a liquid or solid filler, diluent, excipient, solvent or encapsulating material, involved in carrying or transporting the active or actives from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, "treating a cancer", "treating", and "treatment" includes, but is not limited to, preventing or reducing the development of a cancer, reducing the symptoms of cancer, suppressing or inhibiting the growth of an established cancer, preventing metastasis and/or invasion of an existing cancer, promoting or inducing regression of the cancer, inhibiting or suppressing the proliferation of cancerous cells, reducing angiogenesis, killing of malignant or cancerous tumor cells, or increasing the amount of apoptotic cancer cells. In some embodiments, the compounds of the invention are administered to a subject at risk of developing a cancer for the purpose of reducing the risk of developing the cancer. The phrase "inhibiting the growth" or "inhibiting the proliferation" of cancer cells, refers to the slowing, interrupting, arresting, or stopping its growth and metastasis, and does not necessarily indicate a total elimination of the neoplastic growth.

A "patient in need of treatment", as used herein, means a patient that is identified as being in need of treatment. For instance, a patient in need of cancer treatment is a patient identified as having cancer or being at risk for developing cancer. A patient may be diagnosed as being in need of treatment by a healthcare professional and/or by performing one or more diagnostic assays. For instance, patient in need of cancer treatment may be a patient diagnosed with cancer or being at risk of cancer by a healthcare professional. Diagnostic assays to evaluate if a patient has a cancer or is at risk for developing cancer are known in the art.

When the methods include administering to the patient more than one active agent, the agents may be administered within 7, 6, 5, 4, 3, 2 or 1 days; within 24, 12, 6, 5, 4, 3, 2 or 1 hours, within 60, 50, 40, 30, 20, 10, 5 or 1 minutes; or substantially simultaneously. The methods of the invention may include administering one or more agents to the patient by oral, systemic, parenteral, topical, intravenous, inhalational, or intramuscular administration.

The methods of the present invention include administering to a patient a first agent in combination with a second agent selected from the agents of Table 1, or an analog thereof, in an amount that is effective to treat the patient. In an embodiment, the method further includes administering a third agent selected from the agents of Table 1. In the present disclosure, the inventors have found that the mechanisms by which the agents listed in Table 1 work together in clinical combination may act as a more potent version of a single agent alone. A combination therapy of the present disclosure might be hypothesized to interact in two general ways: (a) one agent may reinforce the action of another agent, or (b) the two drugs may combine to exert effects that are distinct from either individual compound.

TABLE 1

| Clofazimine (anti-inflammatory) | Bactericidal Antibiotic (for example, rifabutin) | Macrolide Antibiotic (for example, clarithromycin) |
|---|---|---|
| 5' Substituted Nucleosides (for example, brivudine) | Sphingosine Kinase Inhibitors (for example, ABC294640) | Urokinase Inhibitors (for example, upamostat) |

The agents of Table 1 may be administered within 7, 6, 5, 4, 3, 2 or 1 days; within 24, 12, 6, 5, 4, 3, 2 or 1 hours, within 60, 50, 40, 30, 20, 10, 5 or 1 minutes; or substantially simultaneously. The methods of the invention may include administering an agent from Table 1 to the patient by oral, systemic, parenteral, topical, intravenous, inhalational, or intramuscular administration. In an embodiment, the methods of the invention include administering an agent from Table 1 to the patient by oral administration.

In an embodiment, the present disclosure describes a cancer combination therapy including two or more agents selected from the agents of Table 1. In an embodiment, the two or more agents are present in amounts that, when administered together to a patient with cancer, are effective to treat the patient. In an embodiment, the composition consists of active ingredients and excipients, and the active ingredients consist of two or more agents selected from agents of Table 1.

Active ingredients or agents useful in the invention include those described herein in any of their pharmaceutically acceptable forms, including isomers, salts, solvates, and polymorphs thereof, as well as racemic mixtures and prodrugs.

In an embodiment, a combination therapy of the present disclosure for treating cancer offers the advantage of having enhanced anti-invasion effects on cancer cells as compared with therapy that only includes administering a single compound of the combination.

In an embodiment, a combination therapy of the present disclosure for treating cancer offers the advantage of having enhanced anti-migration effects on cancer cells as compared with therapy that only includes administering a single compound of the combination.

In an embodiment, a combination therapy of the present disclosure for treating cancer offers the advantage of having enhanced anti-metastatic effects on cancer cells as compared with therapy that only includes administering a single compound of the combination.

In an embodiment, a combination therapy of the present disclosure for treating cancer offers the advantage of having enhanced anti-proliferative effects on cancer cells as compared with therapy that only includes administering a single compound of the combination. In an embodiment, the enhanced anti-proliferation effects on cancer cells is a result of one or more of the compounds ability to decrease or stop the production of, or overexpression of, cytokines in the tumor cells, stromal cells, or both. In an embodiment, the cytokine affected by the compound is interleukin-6 (IL-6). IL-6 has been shown to be involved in the proliferation and differentiation of various malignant tumor cells. In addition, overexpression of both IL-6 and its receptors (IL-6R and sIL-6R) has been found in various cancers. Elevated levels of IL-6 have been found in culture supernatant of multidrug resistant cell lines and the elevated IL-6 levels in the serum of cancer patient have been associated with poor clinical outcomes.

In an embodiment, each agent of the present invention alone is capable of at least one of anti-invasion effects, anti-migration effects, anti-metastatic effects, anti-proliferative effects, and apoptosis induction, and the combination of two or more agents of the present invention synergistically inhibit cell growth and increase apoptosis.

In an embodiment, a combination cancer therapy of the present disclosure includes administration of a therapeutically effective amount of clarithromycin and a therapeutically effective amount of a serine protease inhibitor. In an embodiment, the serine protease inhibitor is upamostat.

In an embodiment, a combination cancer therapy of the present disclosure includes administration of a therapeutically effective amount of clarithromycin and a therapeutically effective amount of a nucleoside analogue. In an embodiment, the nucleoside analogue is brivudine.

In an embodiment, a combination cancer therapy of the present disclosure includes administration of a therapeutically effective amount of clarithromycin and a therapeutically effective amount of an aryladamantane compound that is an inhibitor of sphingosine kinase, either sphingosine kinase 1 (SK1) or sphingosine kinases 2 (SK2). In an embodiment, the aryladamantane compound is [3-(4-chlorophenyl)-adamantane-1-carboxylic acid (pyridin-4-ylmethyl)amide] also known as "ABC294640". In an embodiment, the aryladamantane compound is ABC294735.

In an embodiment, a combination cancer therapy of the present disclosure includes administration of a therapeutically effective amount of clarithromycin; a therapeutically effective amount of a serine protease inhibitor; and a therapeutically effective amount of a nucleoside analogue. In an embodiment, the serine protease inhibitor is upamostat. In an embodiment, the nucleoside analogue is brivudine.

In an embodiment, a combination cancer therapy of the present disclosure includes administration of a therapeutically effective amount of clarithromycin; a therapeutically effective amount of a serine protease inhibitor; and a therapeutically effective amount of an aryladamantane compound that is an inhibitor of sphingosine kinase, either sphingosine kinase 1 (SK1) or sphingosine kinases 2 (SK2). In an embodiment, the serine protease inhibitor is upamostat. In an embodiment, the aryladamantane compound is [3-(4-chlorophenyl)-adamantane-1-carboxylic acid (pyridin-4-ylmethyl)amide] also known as "ABC294640". In an embodiment, the aryladamantane compound is ABC294735.

In an embodiment, a combination cancer therapy of the present disclosure includes administration of a therapeutically effective amount of clarithromycin; a therapeutically effective amount of a serine protease inhibitor; a therapeutically effective amount of a nucleoside analogue; and a therapeutically effective amount of an aryladamantane compound that is an inhibitor of sphingosine kinase, either sphingosine kinase 1 (SK1) or sphingosine kinases 2 (SK2). In an embodiment, the serine protease inhibitor is upamostat. In an embodiment, the nucleoside analogue is brivudine. In an embodiment, the aryladamantane compound is [3-(4-chlorophenyl)-adamantane-1-carboxylic acid (pyridin-4-ylmethyl)amide] also known as "ABC294640". In an embodiment, the aryladamantane compound is ABC294735.

In an embodiment, a combination cancer therapy of the present disclosure includes administration of a therapeutically effective amount of a serine protease inhibitor and a therapeutically effective amount of a nucleoside analogue. In an embodiment, the serine protease inhibitor is upamostat. In an embodiment, the nucleoside analogue is brivudine.

In an embodiment, a combination cancer therapy of the present disclosure includes administration of a therapeutically effective amount of a serine protease inhibitor and a therapeutically effective amount of an aryladamantane compound that is an inhibitor of sphingosine kinase, either sphingosine kinase 1 (SK1) or sphingosine kinases 2 (SK2). In an embodiment, the serine protease inhibitor is upamostat. In an embodiment, the aryladamantane compound is [3-(4-chlorophenyl)-adamantane-1-carboxylic acid (pyridin-4-ylmethyl)amide] also known as "ABC294640". In an embodiment, the aryladamantane compound is ABC294735.

In an embodiment, a combination cancer therapy of the present disclosure includes administration of a therapeutically effective amount of a nucleoside analogue and a therapeutically effective amount of an aryladamantane compound that is an inhibitor of sphingosine kinase, either sphingosine kinase 1 (SK1) or sphingosine kinases 2 (SK2). In an embodiment, the nucleoside analogue is brivudine. In an embodiment, the aryladamantane compound is [3-(4-chlorophenyl)-adamantane-1-carboxylic acid (pyridin-4-ylmethyl)amide] also known as "ABC294640". In an embodiment, the aryladamantane compound is ABC294735.

In an embodiment, a combination cancer therapy of the present disclosure includes administration of a therapeutically effective amount of a nucleoside analogue; a therapeutically effective amount of a serine protease; and a therapeutically effective amount of an aryladamantane compound that is an inhibitor of sphingosine kinase, either sphingosine kinase 1 (SK1) or sphingosine kinases 2 (SK2). In an embodiment, the nucleoside analogue is brivudine. In an embodiment, the serine protease inhibitor is upamostat. In an embodiment, the aryladamantane compound is [3-(4- chlorophenyl)-adamantane-1-carboxylic acid (pyridin-4-yl-methyl)amide] also known as "ABC294640". In an embodiment, the aryladamantane compound is ABC294735.

In an embodiment, a combination cancer therapy of the present disclosure includes administration of a therapeutically effective amount of a nucleoside analogue and a therapeutically effective amount of an aryladamantane compound that is an inhibitor of sphingosine kinase, either sphingosine kinase 1 (SK1) or sphingosine kinases 2 (SK2). In an embodiment, the nucleoside analogue is brivudine. In an embodiment, the aryladamantane compound is [3-(4-chlorophenyl)-adamantane-1-carboxylic acid (pyridin-4-yl-methyl)amide] also known as "ABC294640". In an embodiment, the aryladamantane compound is ABC294735.

In an embodiment, a pharmaceutical composition of the present invention comprises two or more agents together with one or more pharmaceutically acceptable carrier thereof and optionally one or more other therapeutic ingredients. The carrier must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present disclosure may be manufactured in a manner that is itself known, e.g., by means of conventional mixing, dissolving, granulating, levigating, emulsifying, encapsulating, entrapping or compression processes.

In an embodiment, a pharmaceutical composition of the present invention may conveniently be presented in unit dosage form and may be prepared by any of the methods well known in the art of pharmacy. All methods include the step of bringing into association an agent of the subject disclosure or a pharmaceutically acceptable salt, ester, analog, prodrug or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired composition.

In an embodiment, pharmaceutical compositions of the present disclosure suitable for oral administration may be presented as discrete units such as capsules, cachets or tablets each containing a predetermined amount of the active ingredients; as a powder or granules; as a solution or a suspension in an aqueous liquid or a non-aqueous liquid; or as an oil-in-water liquid emulsion or a water-in-oil liquid emulsion.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All compositions for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Agents of the Present Invention

5' Substituted Nucleosides

The following are presented as non-limiting examples of 5' substituted nucleosides of the present disclosure: 5-(2-bromovinyl-2'-deoxyuridine (BVDU), (E)-5-(2-bromovinyl)-1-.beta.-D-arabinofuranosyluracil, (E)-5-(2-bromovinyl-2'-deoxy-4'-thiouridine, 5-iodo-2'-deoxycytidine, 5-iodo-2'-deoxyuridine, and 2'-deoxy-5-trifluoromethyluridine. Particularly preferred are Brivudine (BVDU) and (E)-5-(2-bromovinyl-) uracil (BVU). BVDU may be used in its salt form, in a protected form or in a prodrug form.

Brivudine (bromovinyldeoxyuridine or BVDU for short), is a nucleoside analogue that interacts with two phenylalanine residues (Phe29 and Phe33) in the N-terminal domain of HspB1. The drug's full chemical description is (E)-5-(2-bromovinyl)-2-deoxyuridine. Brivudine has been shown to be an effective substance for preventing or reducing resistance formation against treatment with cytostatic agents. The occurrence of "drug resistance" is the main reason for failure in cancer chemotherapy. Tumors which initially react sensitively to cytostatic agents very frequently recover after a certain treatment time and then are resistant to the effects of various types of antineoplastic drugs.

A non-limiting example of the prodrug form of BVDU is represented below:

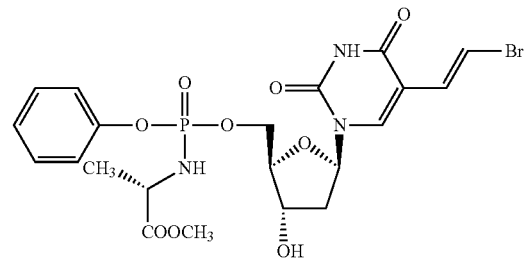 [SMILES: COC(=O)[C@H](C)NP(=O)(OC[C@H]1O[C@@H](n2cc(/C=C/Br)c(=O)[nH]c2=O)C[C@@H]1O)Oc1ccccc1]

Brivudine is represented below:

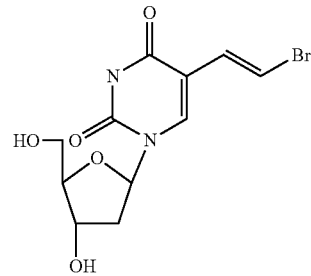 [SMILES: O=c1[nH]c(=O)n(C2CC(O)C(CO)O2)cc1/C=C/Br]

In an embodiment, a combination cancer therapy of the present disclosure includes co-administering to a patient having cancer and in need of treatment, brivudine, a salt thereof, or BVDU in protected or in prodrug form, along with at least one additional agent selected from Table 1, and in combination with at least one cytostatic agent selected from one or more of alkaloids, alkylating agents, antimetabolites, antibiotics, or cisplatin. During a method of treating cancer with a combination therapy that comprises BVDU, BVDU may be administered in an amount effective to produce a concentration of 0.02 μg/ml to 10.0 μg/ml in blood. During a method of treating cancer with a combination therapy that comprises BVDU, BVDU may be administered in an amount effective to produce a concentration of 0.05 μg/ml to 5 μg/ml in blood.

In an embodiment, a cancer combination therapy of the present disclosure for reducing resistance in cytostatic treatment comprises delivering to a patient a therapeutically effective amount of at least one cytostatic agent, a therapeutically effective amount of BVDU, a salt thereof, or BVDU in protected form or prodrug form, and a therapeutically effective amount of at least one additional agent selected from Table 1.

In an embodiment, a cancer combination therapy of the present disclosure for increasing the apoptotic effect of cytostatics after chemotherapy comprises administering (E)-5-(2-bromovinyl)-2'-deoxyuridine (BVDU), BVDU salt, or BVDU prodrug, or mixture thereof, the administering being without administration of a cytostatic, during a recovery phase after a cytostatic chemotherapy cycle, wherein the cytostatic chemotherapy cycle includes administration of (a) BVDU, prodrug of the general formula I, or BVDU salt, or mixture thereof (b) at least one additional agent selected from Table 1; and (c) a cytostatic. In an embodiment, during the cytostatic chemotherapy cycle, administered amounts of cytostatic are increased over a period of the cytostatic chemotherapy cycle, and the administered amount of BVDU, BVDU salt, or prodrug, or mixture thereof is constant. In an embodiment, the cytostatic chemotherapy cycle has a duration of from 7 to 60 days. In an embodiment, the recovery phase has a duration of from 3 to 10 days.

Urokinase Inhibitors

Upamostat ("WX-671" or "Mesupron") has been shown to inhibit the urokinase-type plasminogen activator (uPA) system. Upamostat is a serine protease inhibitor. After oral administration, serine protease inhibitor WX-671 is converted to the active Nα-(2,4,6-triisopropylphenylsulfonyl)-3-amidino-(L)-phenylalanine-4-ethoxycarbonylpiperazide ("WX-UK1"), which inhibits several serine proteases, particularly uPA. The drug's full chemical description is (S)-ethyl 4-(3-(3-(N-hydroxycarbamimidoyl)phenyl)-2-(2,4,6-triisopropylphenylsulfonamido)propanoyl) piperazine-1-carboxylate.

Upamostat is represented by the following formula:

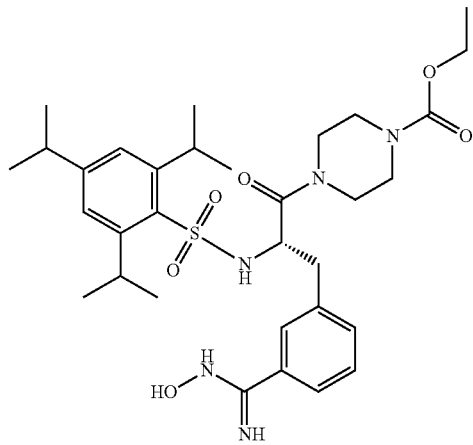 [SMILES: CCOC(=O)N1CCN(C(=O)[C@H](Cc2cccc(C(=N)NO)c2)NS(=O)(=O)c2c(C(C)C)cc(C(C)C)cc2C(C)C)CC1]

In an embodiment, a combination cancer therapy of the present disclosure includes co-administering to a patient having cancer and in need of treatment, upamostat, along with at least one additional agent selected from Table 1. During a method of treating cancer with a combination therapy that comprises upamostat, upamostat may be administered orally at a dose of about 0.5 mg/kg to about 1.1 mg/kg. In an embodiment, upamostat is administered orally at a daily dose of between about 200 mg to 400 mg. In an embodiment, upamostat is administered orally at a daily dose of between about 150 mg to 550 mg. In an embodiment, upamostat is administered orally at a daily dose of between about 200 mg to 550 mg. In an embodiment, upamostat is administered orally at a daily dose of between about 250 mg to 550 mg. In an embodiment, upamostat is administered orally at a daily dose of between about 300 mg to 550 mg. In an embodiment, upamostat is administered orally at a daily dose of between about 350 mg to 550 mg. In an embodiment, upamostat is administered orally at a daily dose of between about 400 mg to 550 mg. In an embodiment, upamostat is administered orally at a daily dose of between about 450 mg to 550 mg. In an embodiment, upamostat is administered orally at a daily dose of between about 500 mg to 550 mg. In an embodiment, upamostat is administered orally at a daily dose of between about 200 mg to 550 mg. In an embodiment, upamostat is administered orally at a daily dose of between about 200 mg to 500 mg. In an embodiment, upamostat is administered orally at a daily dose of between about 200 mg to 450 mg. In an embodiment, upamostat is administered orally at a daily dose of between about 200 mg to 350 mg. In an embodiment, upamostat is administered orally at a daily dose of between about 200 mg to 300 mg. In an embodiment, upamostat is administered orally at a daily dose of between about 200 mg to 250 mg. In an embodiment, upamostat is administered orally at a daily dose of between about 500 mg to 1000 mg. In an embodiment, upamostat is administered orally at a daily dose of between about 750 mg to 1000 mg. In an embodiment, upamostat is administered orally at a daily dose of between about 500 mg to 750 mg.

Clofazimine

The anti-leprosy drug Clofazimine is known to inhibit respiratory function and hence energy metabolism in yeast and in transformed fibroblasts. Clofazimine is represented by the following formula:

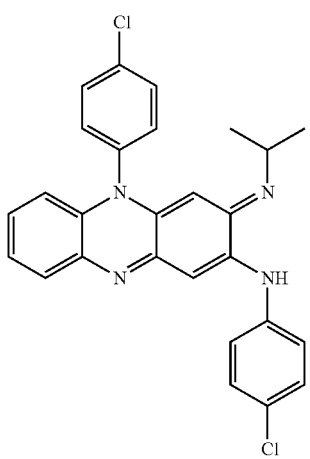 [SMILES: CC(C)/N=c1\cc2n(-c3ccc(Cl)cc3)c3ccccc3nc-2cc1Nc1ccc(Cl)cc1]

Clofazimine has been shown to inhibit the growth rate of tumor cells both in vitro and in vivo. In an embodiment, a combination cancer therapy of the present disclosure includes co-administering to a patient having cancer and in need of treatment clofazimine, along with at least one additional agent selected from Table 1. In an embodiment, clofazimine is administered orally to a patient as a component of a solid oral dosage form. In an embodiment, the dosage of clofazimine per day is from about 50 mg/day to about 580 mg/day. In an embodiment, the maximum dosage of clofazimine is 100 mg/day till recovery.

Rifabutin

Rifabutin is represented by the following formula:

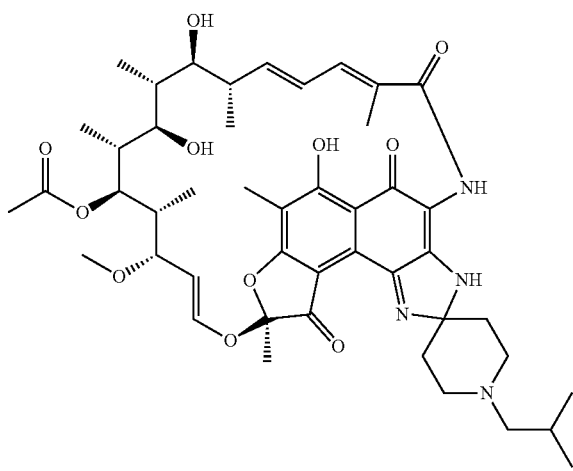

In an embodiment, a combination cancer therapy of the present disclosure includes co-administering to a patient having cancer and in need of treatment rifabutin, along with at least one additional agent selected from Table 1. In an embodiment, rifabutin is administered orally to a patient as a component of a solid oral dosage form. In an embodiment, the dosage of rifabutin per day is from about 80 mg/day to about 480 mg/day. In an embodiment, the maximum dosage of rifabutin is 480 mg/day till recovery. In an embodiment, rifabutin is administered orally as a 150 mg tablet twice per day. In an embodiment, rifabutin is administered orally as a 300 mg tablet once per day. In an embodiment, rifabutin is administered as a component of a solid oral dosage form comprising from 45 mg to 60 mg of rifabutin per dosage form, for up to six times per day.

Clarithromycin

Clarithromycin is represented by the following formula:

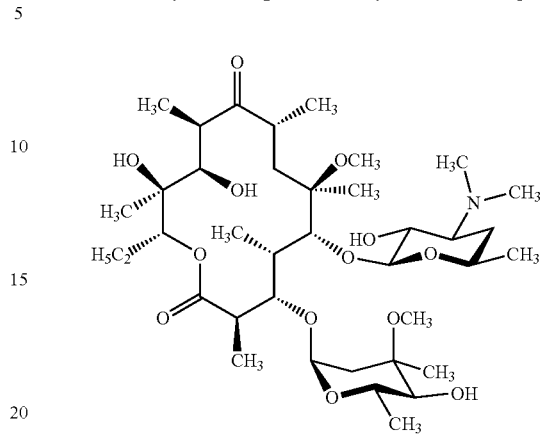

In an embodiment, a combination cancer therapy of the present disclosure includes co-administering to a patient having cancer and in need of treatment clarithromycin, along with at least one additional agent selected from Table 1. In an embodiment, clarithromycin is administered orally to a patient as a component of a solid oral dosage form. In an embodiment, clarithromycin is administered as an intravenous infusion to a patient.

In an embodiment, the dosage of clarithromycin per day is from about 180 mg/day to about 1000 mg/day till recovery. In an embodiment, the maximum dosage of clarithromycin is 980-1000 mg/day till recovery. In an embodiment, two doses of 500 mg clarithromycin is administered as an intravenously (IV) infusion, using a solution concentration of about 2 mg/ml. In an embodiment, 1 gram daily of clarithromycin can be administered as an intravenously (IV) infusion for a period of from two days to five days. In an embodiment, 1 gram daily of clarithromycin can be administered as an intravenously (IV) infusion for a period of three days. In an embodiment, clarithromycin is administered orally as a 500 mg tablet twice per day. In an embodiment, clarithromycin is administered as a component of a solid oral dosage form comprising from 95 mg to 125 mg of clarithromycin per dosage form.

In an embodiment, a combination cancer therapy of the present disclosure includes administering to a patient having cancer and in need of treatment, rifabutin, clarithromycin, and clofazimine as a single solid oral dosage form. In an embodiment, a solid oral dosage form of the present disclosure comprises rifabutin, clarithromycin, clofazimine, and a pharmaceutically acceptable carrier, wherein the amount of clofazimine is 5-18% w/w relative to the amount of clarithromycin (such as, 7-16%, 9-14%, 9-12%, 10-15%, or 0-11% w/w) and 10-25% w/w relative to the amount of rifabutin (such as, 12-25%, 12-23%, 15-25%, 15-23%, 18-25%, 18-23%, 20-25%, 20-23%, or 21-23% w/w).

In an embodiment, a solid oral dosage form of the present disclosure comprises rifabutin, clarithromycin, and clofazimine in a 8-10:18-20:1-2.5 w/w/w ratio (for example, a 8.5-9.5:18.5-19.5:1.5-2.5 w/w/w ratio or a 9:19:2 ratio, wherein each variable is free to vary 0.5 or 0.25). In an embodiment, a solid oral dosage form of the present disclosure comprises rifabutin, clarithromycin, and clofazimine in about a 9:19:2 w/w/w ratio, wherein each of the variables are free to vary ±2, 1, 0.5, or 0.25 (e.g., 9±0.5:19±5:2±0.0.5).

For example in an embodiment, a solid oral dosage form of the present disclosure comprises 90 mg rifabutin (±30, 20, 10, 5, 2, or 1 mg), 190 mg clarithromycin (±60, 40, 20, 10, 5, 2, or 1 mg), and 20 mg clofazimine (±10, 7, 5, 2, or 1 mg). In an embodiment, a solid oral dosage form of the present disclosure comprises 45 mg rifabutin (±15, 10, 7, 5, 2, or 1 mg), 95 mg clarithromycin (±30, 20, 10, 5, 2, or 1 mg), and 10 mg clofazimine (±6, 5, 2, or 1 mg).

In embodiment, a solid oral dosage form of the present disclosure having rifabutin, clarithromycin and clofazimine further comprises an absorption enhancer that may improve bioavailability of one or more of the active ingredients. The amount of absorption enhancer may between 300-700% w/w relative to the amount of clofazimine including 400-600% or 450-550% or 475-525%. In certain embodiments, the absorption enhancer is polyethylene glycol (PEG), for example, polyethylene glycol having an average molecular weight of between 200-20,000 including between 1000-15000 or 5000-12000 or 7000-9000 or 7500-8500, for example PEG 8000.

In embodiment, a solid oral dosage form of the present disclosure that includes rifabutin, clarithromycin and clofazimine further comprises one or more additional excipients, such as MCC-Tabulose type 200, Mg Stearate, SLS-Emal 10Pwd HD, a polysorbate (such as, polysorbate 80), or a combination thereof, including all of these. In some instances, the present compositions include both polyethylene glycol and a polysorbate, such as polysorbate 80, wherein the amount of polysorbate is 30-120% w/w relative to the amount of clofazimine (such as 50-100%, 50-85%, or 60-75%).

In an embodiment, a solid oral dosage form of the present disclosure that includes rifabutin, clarithromycin and clofazimine further comprises one or more additional excipients, such as Microcrystalline cellulose (MCC) TABU-LOSE® SC 200), Mg Stearate, Sodium Lauryl Sulfate (SLS) EMAL® 10Pwd HD, a polysorbate (such as, polysorbate 80), or a combination thereof, including all of these. In some instances, the present compositions include both polyethylene glycol and a polysorbate, such as polysorbate 80, wherein the amount of polysorbate is 30-120% w/w relative to the amount of clofazimine (such as 50-100%, 50-85%, or 60-75%).

In an embodiment, a pharmaceutical composition of the present invention comprises a capsule having 10 mg clofazimine, 95 mg of clarithromycin and 45 mf of rifabutin together with various excipients, known as RHB-104. In an embodiment, a RHB-104 capsule of the present invention includes the following components:

Composition of RHB-104 Capsules

| Ingredient(Grade) | Function | mg per capsule | % |
|---|---|---|---|
| Clofazimine (USP/Ph.Eur.). | Active | 10.00 | 3.23 |
| Rifabutin (USP/Ph.Eur.) | Active | 45.00 | 14.53 |
| Clarithromycin | Active | 95.00 | 30.67 |
| Polyethylene Glycol 8000 (NF/Ph.Eur.) | Dispersing Agent | 50.00 | 16.14 |
| Polysorbate 80 (NF/Ph.Eur.) | Wetting Agent | 6.66 | 2.15 |
| Microcrystalline Cellulose 200 (NF-Ph.Eur.) | Diluent | 28.00 | 9.04 |
| Magnesium Stearate, vegetable grade (NF/Ph.Eur.) | Lubricant | 4.65 | 1.51 |
| Sodium Lauryl Sulfate (NF/Ph.Eur.) | Wetting Agent | 10.00 | 3.23 |
| Microcrystalline Cellulose 200 | Diluent | 60.42 | 19.51 |
| Hard Gelatin Capsule (Mfg.Std) | — | 1 unit | — |
| Total | | 309.76 | 100 |

In an embodiment, a solid oral dosage form of the present disclosure is available in the form of a tablet or a capsule containing an active in a powdered form. In an embodiment, a solid oral dosage form of the present disclosure is in the form of a tablet or a capsule containing an active in a microencapsulated form. In an embodiment, a solid oral dosage form of the present disclosure is in the form of a tablet or a capsule containing an active in a microgranulated form.

Sphingosine Kinase Inhibitors

An aryladamantane compound of the present invention has been shown to be capable of selectively inhibiting SK2 activity in vitro. Examples of aryladamantane compounds of the present invention are generally represented by the formula below:

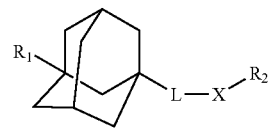

(I)

and pharmaceutically acceptable salts thereof, wherein
L is a bond or is —C(R$_3$,R$_4$)—;
X is —C(R$_3$, R$_4$)N(R$_5$)—, —C(O)N(R$_4$)—, —N(R$_4$)C(O)—, —C(R$_4$,R$_5$)—, —N(R$_4$)—, —O—, —S—, —C(O)—, —S(O)$_2$—, —S(O)$_2$N(R$_4$)— or —N(R$_4$)S(O)$_2$—;
R$_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —H, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;
R$_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;
R$_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, oxo (═O), —COOH, —OH, —SH, —S-alkyl, —CN—, —NO$_2$, —NH$_2$, —CO$_2$(alkyl), —OC (O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

wherein the alkyl and ring portion of each of the above $R_1$, $R_2$, and $R_3$ groups is optionally substituted with up to 5 groups that are independently $(C_1-C_6)$ alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or $(C_1-C_6)$ alkyl, and wherein each alkyl portion of a substituent is optionally further substituted with 1, 2, or 3 groups independently selected from halogen, CN, OH, and NH$_2$; and $R_4$ and $R_5$ are independently H or alkyl, provided that when $R_3$ and $R_4$ are on the same carbon and $R_3$ is oxo, then $R_4$ is absent.

Aryladamantane compounds include compounds of the following formula I-1:

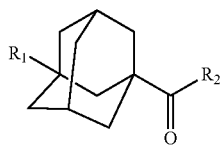

(I-1)

and pharmaceutically acceptable salts thereof, wherein:

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COH, —OH, —SH, —S-alkyl, —CN, —NO$_2$, —NH$_2$, —CO$_2$(alkyl), —C(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl; and $R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —NH-aryl, -alkenyl-heteroaryl, -heteroaryl, —NH-alkyl, —NH— cycloalkyl, or -alkenyl-heteroaryl-aryl, wherein the alkyl and ring portion of each of the above $R_1$, and $R_2$ groups is optionally substituted with up to 5 groups that are independently $(C_1-C_6)$ alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or $(C_1-C_6)$ alkyl, and wherein each alkyl portion of a substituent is optionally further substituted with 1, 2, or 3 groups independently selected from halogen, CN, OR NH$_2$.

Aryladamantane compounds include those of formula II:

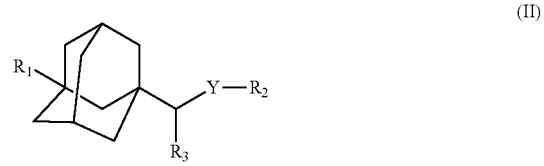

(II)

and pharmaceutically acceptable salts thereof, wherein:

Y is —C($R_4$,$R_5$)—, —N($R_4$)—, —O—, or —C(O)—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COH, —OH, —SH, —S-alkyl, —CN, —NO$_2$, —NH$_2$, —CO$_2$(alkyl), —C(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COH, —OH, —SH, —S-alkyl, —CN, —NO$_2$, —NH$_2$, —CO$_2$(alkyl), —C(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

$R_3$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, oxo (=O), —COOH, —OH, —SH, —S-alkyl, —CN, —NO$_2$, —NH$_2$, —CO$_2$(alkyl), —OC(O) alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

wherein the alkyl and ring portion of each of the above $R_1$, $R_2$, and $R_3$ groups is optionally substituted with up to 5 groups that are independently $(C_1-C_6)$ alkyl, halogen, haloalkyl, —OC(O)($C_1$-$C_6$ alkyl), —C(O)O($C_1$-$C_6$ alkyl), —CONR'R", —OC(O)NR'R", —NR'C(O)R", —CF$_3$, —OCF$_3$, —OH, $C_1$-$C_6$ alkoxy, hydroxyalkyl, —CN, —CO$_2$H, —SH, —S-alkyl, —SOR'R", —SO$_2$R', —NO$_2$, or NR'R", wherein R' and R" are independently H or $(C_1-C_6)$ alkyl, and wherein each alkyl portion of a substituent is optionally further substituted with 1, 2, or 3 groups independently selected from halogen, CN, OH, NH$_2$; and $R_4$ and $R_5$ are independently H or alkyl.

Compounds of the formula II include those wherein:

Y is —C($R_4$,$R_5$)— or —N($R_4$)—;

$R_1$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, or mono or dialkylthiocarbamoyl;

$R_2$ is H, alkyl, cycloalkyl, cycloalkylalkyl, alkenyl, alkynyl, heteroalkyl, aryl, alkylaryl, alkenylaryl, heterocyclyl, heteroaryl, alkylheteroaryl, heterocycloalkyl, alkyl-heterocycloalkyl, acyl, aroyl, halogen, haloalkyl, alkoxy, haloalkoxy, hydroxyalkyl, alkanoyl, —COOH, —OH, —SH, —S-alkyl, —CN, —NO$_2$, —NH$_2$, —CO$_2$(alkyl), —OC(O)alkyl, carbamoyl, mono or dialkylaminocarbamoyl, mono or dialkylcarbamoyl, mono or dialkylamino, aminoalkyl, mono- or dialkylaminoalkyl, thiocarbamoyl, mono or dialkylthiocarbamoyl, alkyl-S-alkyl, -heteroaryl-aryl, -alkyl-heteroaryl-aryl, —C(O)—NH-aryl, -alkenyl-heteroaryl, —C(O)-heteroaryl, or -alkenyl-heteroaryl-aryl;

wherein the alkyl and ring portion of each of the above $R_1$ and $R_2$ groups is optionally substituted with up to 5 groups that are independently ($C_1$-$C_6$) alkyl, halogen, haloalkyl, —OC(O)($C_1$-$C_6$ alkyl), —C(O)O($C_1$-$C_6$ alkyl), —CONR$_4$R$_5$, —OC(O)NR$_4$R$_5$, —NR$_4$C(O)R$_5$, —CF$_3$, —OCF$_3$, —OH, $C_1$-$C_6$ alkoxy, hydroxyalkyl, —CN, —CO$_2$H, —SH, —S-alkyl, —SOR$_4$R$_5$, —SO$_2$R$_4$R$_5$, —NO$_2$, or NR$_4$R$_5$, and wherein each alkyl portion of a substituent is optionally further substituted with 1, 2, or 3 groups independently selected from halogen, CN, OH, NH$_2$;

$R_3$ is H, alkyl, or oxo (=O); and $R_4$ and R are independently H or ($C_1$-$C_6$)alkyl.

Representative formula II compounds include:

| Cmpd | Chemical name | Y | R3 | R1 | R2 |
|---|---|---|---|---|---|
| 1 | 3-(4-Chloro-phenyl)-adamantane-1-carboxylic acidisopropylamide | NH | =O | Cl-phenyl | isopropyl |
| 2 | 3-(4-Chloro-phenyl)-adamantane-1-carboxylic acidcyclopropylamide | NH | =O | Cl-phenyl | cyclopropyl |
| 3 | 3-(4-Chloro-phenyl)-adamantane-1-carboxylic acid(2-ethylsulfanyl-ethyl)-amide | NH | =O | Cl-phenyl | -CH$_2$CH$_2$SEt |
| 4 | 3-(4-Chloro-phenyl)-adamantane-1-carboxylic acidphenylamide | NH | =O | Cl-phenyl | phenyl |
| 5 | Adamantane-1-carboxylic acid(4-hydroxy-phenyl)-amide | NH | =O | H | 4-hydroxyphenyl |
| 6 | 3-(4-Chloro-phenyl)-adamantane-4-carboxylic acid(4-hydroxy-phenyl)-amide | NH | =O | Cl-phenyl | 4-hydroxyphenyl |
| 7 | Acetic acid 4-{[3-(4-chloro-phenyl)-adamantane-1-carbonyl]-amino}-phenyl ester | NH | =O | Cl-phenyl | 4-OC(O)CH$_3$-phenyl |
| 8 | 3-(4-Chloro-phenyl)-adamantane-1-carboxylic acid(2,4-dihydroxy-phenyl)-amide | NH | =O | Cl-phenyl | 2,4-dihydroxyphenyl |
| 9 | 3-(4-Chloro-phenyl)-adamantane-1-carboxylic acid(3-hydroxymethyl-phenyl)-amide | NH | =O | Cl-phenyl | 3-hydroxymethylphenyl |
| 10 | Adamantane-1-carboxylic acid(4-cyanomethyl-phenyl)-amide | NH | =O | H | 4-cyanomethylphenyl |

-continued

| Cmpd | Chemical name | Y | R3 | R1 | R2 |
|---|---|---|---|---|---|
| 11 | 3-(4-Chloro-phenyl)-adamantane-1-carboxylic acid(4-cyanomethyl-phenyl)-amide | NH | =O | 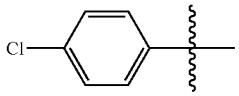 | 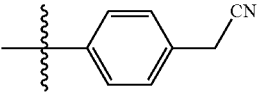 [SMILES: *c1ccc(CC#N)cc1] |
| 12 | 3-(4-Chloro-phenyl)-adamantane-1-carboxylic acidbenzylamide | NH | =O | 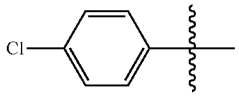 | 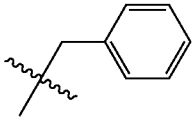 |
| 13 | 3-(4-Chloro-phenyl)-adamantane-1-carboxylic acid4-tert-butyl-benzylamide | NH | =O | 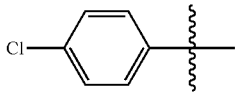 | 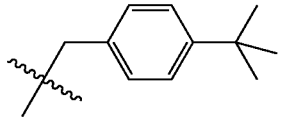 [SMILES: *Cc1ccc(C(C)(C)C)cc1] |
| 14 | 3-(4-Chloro-phenyl)-adamantane-1-carboxylic acid4-methylsulfamoyl-benzylamide | NH | =O | 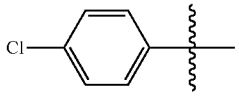 [SMILES: *c1ccc(Cl)cc1] | 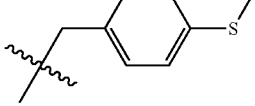 |
| 15 | 3-(4-Chloro-phenyl)-adamantane-1-carboxylic acid3-trifluoromethyl-benzylamide | NH | =O | 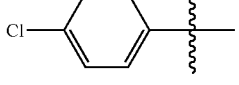 | 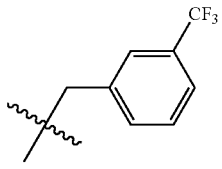 [SMILES: *Cc1cccc(C(F)(F)F)c1] |
| 16 | 3-(4-Chloro-phenyl)-adamantane-1-carboxylic acid4-trifluoromethyl-benzylamide | NH | =O | 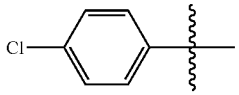 | 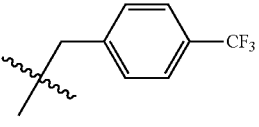 [SMILES: *Cc1ccc(C(F)(F)F)cc1] |
| 17 | 3-(4-Chloro-phenyl)-adamantane-1-carboxylic acid3,5-bis-trifluoromethyl-benzylamide | NH | =O | 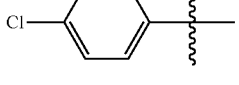 | 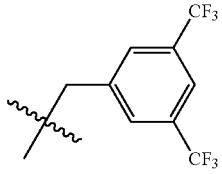 |
| 18 | 3-(4-Chloro-phenyl)-adamantane-1-carboxylic acid3-fluoro-5-trifluoromethyl-benzylamide | NH | =O | 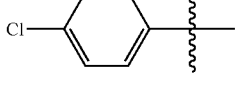 | 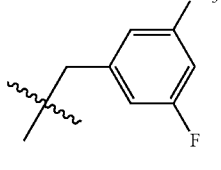 |
| 19 | 3-(4-Chloro-phenyl)-adamantane-1-carboxylic acid2-fluoro-4-trifluoromethyl-benzylamide | NH | =O | 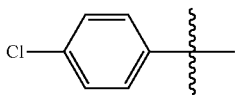 [SMILES: *c1ccc(Cl)cc1] | 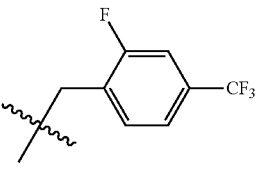 |
| 20 | 3-(4-Chloro-phenyl)-adamantane-1-carboxylic acid3,5-difluoro-benzylamide | NH | =O | 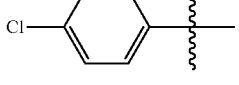 | 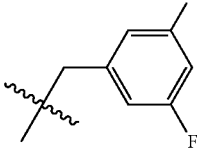 |

-continued

| Cmpd | Chemical name | Y | R3 | R1 | R2 |
|---|---|---|---|---|---|
| 21 | 3-(4-Chloro-phenyl)-adamantane-1-carboxylic acid3,5-difluoro-benzylamide | NH | =O | 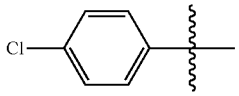 [SMILES: *c1ccc(Cl)cc1] | 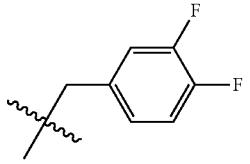 |
| 22 | 3-(4-Chloro-phenyl)-adamantane-1-carboxylic acid3,4,5-trifluoro-benzylamide | NH | =O | 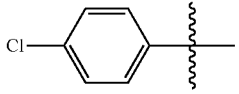 [SMILES: *c1ccc(Cl)cc1] | 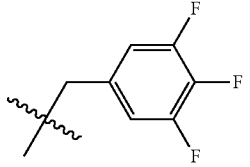 |
| 23 | 3-(4-Chloro-phenyl)-adamantane-1-carobxylic acid3-chloro-4-fluoro-benzylamide | NH | =O | 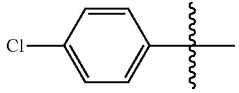 [SMILES: *c1ccc(Cl)cc1] | 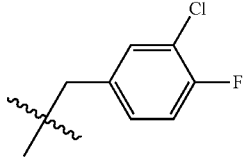 [SMILES: *Cc1ccc(F)c(F)c1] |
| 24 | 3-(4-Chloro-phenyl)-adamantane-1-carboxylic acid4-fluoro-3-trifluoromethyl-benzylamide | NH | =O | 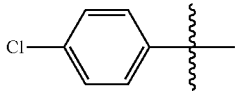 [SMILES: *c1ccc(Cl)cc1] | 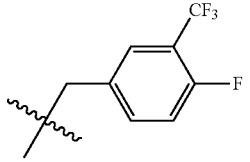 [SMILES: *Cc1ccc(F)c(Cl)c1] |
| 25 | 3-(4-Chloro-phenyl)-adamantane-1-carboxylic acid2-chloro-4-fluoro-benzylamide | NH | =O | 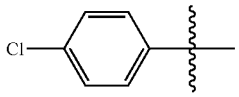 [SMILES: *c1ccc(Cl)cc1] | 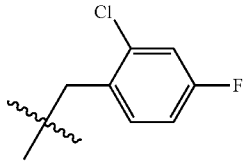 [SMILES: *Cc1ccc(F)cc1Cl] |
| 26 | 3-(4-Chloro-phenyl)-adamantane-1-carboxylic acid4-chloro-3-trifluoromethyl-benzylamide | NH | =O | 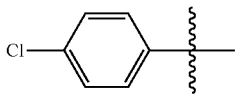 [SMILES: *c1ccc(Cl)cc1] | 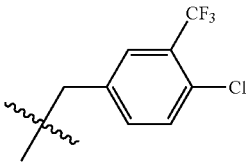 [SMILES: *Cc1ccc(Cl)c(C(F)(F)F)c1] |
| 27 | 3-(4-Chloro-phenyl)-adamantane-1-carboxylic acid3-aminomethyl-2,4,5,6-tetrachloro-benzylamide | NH | =O | 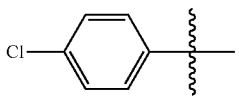 [SMILES: *c1ccc(Cl)cc1] | 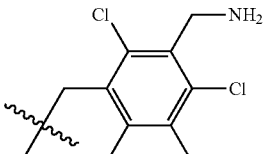 |
| 28 | 3-(4-Chloro-phenyl)-adamantane-1-carboxylic acid[1-(4-chloro-phenyl)-ethyl]-amide | NH | =O | 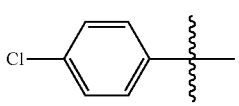 [SMILES: *c1ccc(Cl)cc1] | 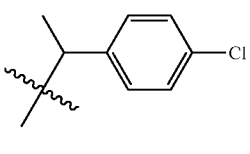 [SMILES: *C(C)c1ccc(Cl)cc1] |
| 29 | 3-(4-Chloro-phenyl)-adamantane-1-carboxylic acid[1-(4-bromo-phenyl)-ethyl]-amide | NH | =O | 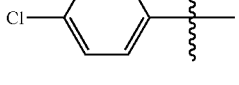 | 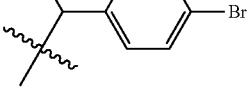 |

-continued

| Cmpd | Chemical name | Y | R3 | R1 | R2 |
|---|---|---|---|---|---|
| 30 | 3-(4-Chloro-phenyl)-adamantane-1-carboxylic acid 4-methanesulfonyl-benzylamide | NH | =O | 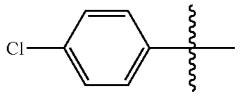 [SMILES: *c1ccc(Cl)cc1] | 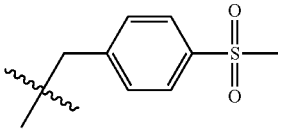 [SMILES: *Cc1ccc(S(C)(=O)=O)cc1] |
| 31 | 3-(4-Chloro-phenyl)-adamantane-1-carboxylic acid 4-dimethylamino-benzylamide | NH | =O | 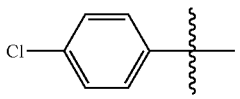 [SMILES: *c1ccc(Cl)cc1] | 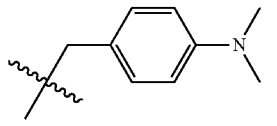 [SMILES: *Cc1ccc(N(C)C)cc1] |
| 32 | 3-(4-Chloro-phenyl)-adamantane-1-carboxylic acid 4-trifluoromethoxy-benzylamide | NH | =O | 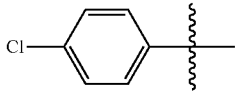 [SMILES: *c1ccc(Cl)cc1] | 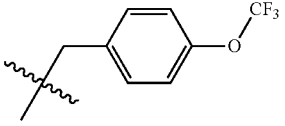 |
| 33 | 3-(4-Chloro-phenyl)-adamantane-1-carboxylic acid 3-trifluoromethoxy-benzylamide | NH | =O | 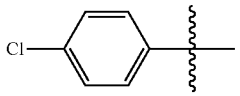 [SMILES: *c1ccc(Cl)cc1] | 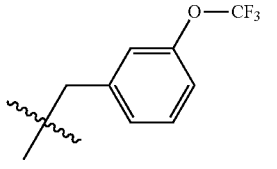 [SMILES: *Cc1cccc(OC(F)(F)F)c1] |
| 34 | 3-(4-Chloro-phenyl)-adamantane-1-carboxylic acid 4-phenoxy-benzylamide | NH | =O | 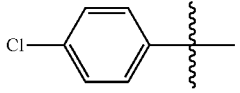 [SMILES: *c1ccc(Cl)cc1] | 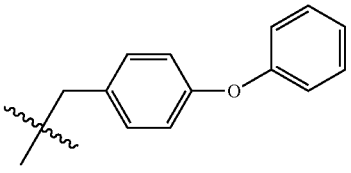 [SMILES: *Cc1ccc(Oc2ccccc2)cc1] |
| 35 | Adamantane-1-carboxylic acid 3,4-dihydroxy-benzylamide | NH | =O | H | 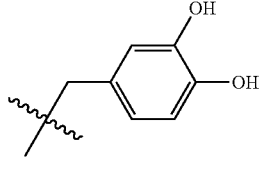 [SMILES: *Cc1ccc(O)c(O)c1] |
| 36 | 3-(4-Chloro-phenyl)-adamantane-1-carboxylic acid 3,4-dihydroxy-benzylamide | NH | =O | 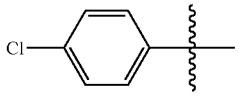 [SMILES: *c1ccc(Cl)cc1] | 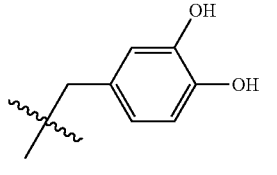 [SMILES: *Cc1ccc(O)c(O)c1] |
| 37 | 3-(4-Chloro-phenyl)-adamantane-1-carboxylic acid phenethyl-amide | NH | =O | 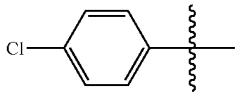 [SMILES: *c1ccc(Cl)cc1] | 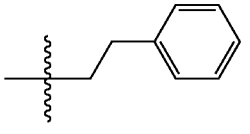 [SMILES: *CCc1ccccc1] |
| 38 | 3-(4-Chloro-phenyl)-adamantane-1-carboxylic acid [2-(4-fluoro-phenyl)-ethyl]-amide | NH | =O | 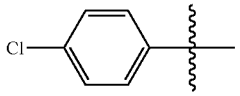 [SMILES: *c1ccc(Cl)cc1] | 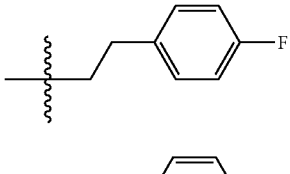 |
| 39 | 3-(4-Chloro-phenyl)-adamantane-1-carboxylic acid [2-(4-bromo-phenyl)-ethyl]-amide | NH | =O | 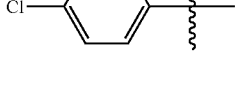 | 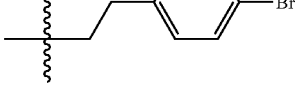 |

-continued

| Cmpd | Chemical name | Y | R3 | R1 | R2 |
|---|---|---|---|---|---|
| 40 | 3-(4-Chloro-phenyl)-adamantane-1-carboxylic acid[2-(4-hydroxy-phenyl)-ethyl]-amide | NH | =O | 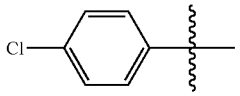 | 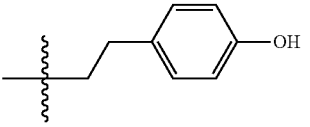 |
| 41 | 3-(4-Chloro-phenyl)-adamantane-1-carboxylic acid4-phenoxy-benzylamide | NH | =O | 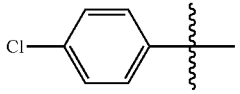 | 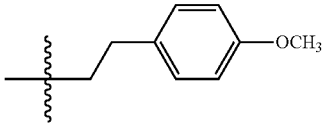 [SMILES: *CCc1ccc(OC)cc1] |
| 42 | 3-(4-Chloro-phenyl)-adamantane-1-carboxylic acid[2-(3-bromo-4-methoxy-phenyl)-ethyl]-amide | NH | =O | 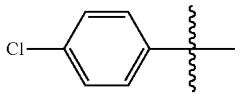 [SMILES: *c1ccc(Cl)cc1] | 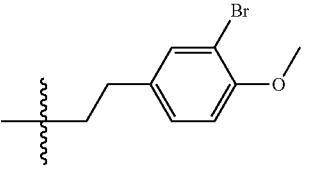 [SMILES: *CCc1ccc(OC)c(Br)c1] |
| 43 | Adamantane-1-carboxylic acid[2-(3,4-dihydroxy-phenyl)-ethyl]-amide | NH | =O | H | 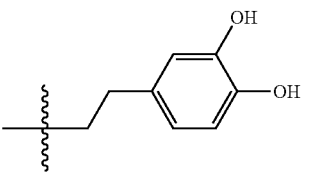 [SMILES: *CCc1ccc(O)c(O)c1] |
| 44 | 3-(4-Chloro-phenyl)-adamantane-1-carboxylic acid[2-(3,4-dihydroxy-phenyl)-ethyl]-amide | NH | =O | 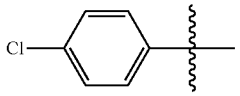 [SMILES: *c1ccc(Cl)cc1] | 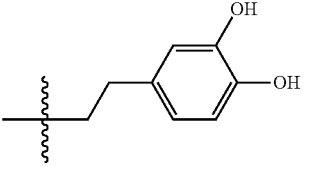 |
| 45 | 3-(4-Chloro-phenyl)-adamantane-1-carboxylic acid(2-benzo[1,3]dioxol-5-yl-ethyl)-amide | NH | =O | 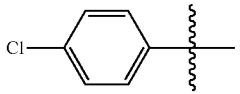 [SMILES: *c1ccc(Cl)cc1] | 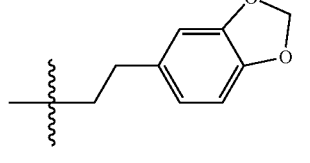 |
| 46 | 3-(4-Chloro-phenyl)-adamantane-1-carboxylic acid[2-(3-phenoxy-phenyl)-ethyl]-amide | NH | =O | 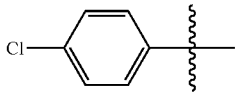 [SMILES: *c1ccc(Cl)cc1] | 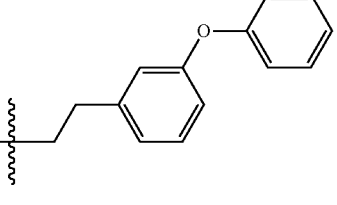 |
| 47 | 3-(4-Chloro-phenyl)-adamantane-1-carboxylic acid[2-(4-phenoxy-phenyl)-ethyl]-amide | NH | =O | 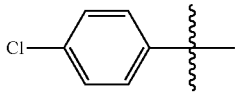 [SMILES: *c1ccc(Cl)cc1] | 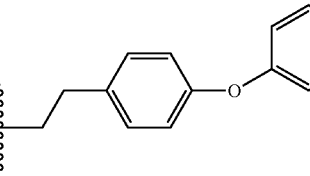 |
| 48 | 3-(4-Chloro-phenyl)-adamantane-1-carboxylic acid(3-phenyl-propyl)-amide | NH | =O | 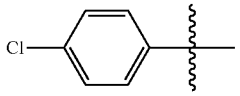 [SMILES: *c1ccc(Cl)cc1] | 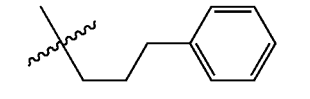 [SMILES: *CCCc1ccccc1] |

-continued

| Cmpd | Chemical name | Y | R3 | R1 | R2 |
|---|---|---|---|---|---|
| 49 | 3-(4-Chloro-phenyl)-adamantane-1-carboxylic acid(biphenyl-4-ylmethyl)-amide | NH | =O | 4-Cl-phenyl | biphenyl-4-ylmethyl |
| 50 | Adamantane-1-carboxylic acid(1-methyl-piperidin-4-yl)-amide | NH | =O | H | 1-methyl-piperidin-4-yl |
| 51 | 3-(4-Chloro-phenyl)-adamantane-1-carboxylic acid(1-methyl-piperidin-4-yl)-amide | NH | =O | 4-Cl-phenyl | 1-methyl-piperidin-4-yl |
| 52 | 3-(4-Chloro-phenyl)-adamantane-1-carboxylic acid(4-methyl-piperazin-1-yl)-amide | NH | =O | 4-Cl-phenyl | 4-methyl-piperazin-1-yl |
| 53 | 3-(4-Chloro-phenyl)-adamantane-1-carboxylic acid(3-tert-butylamino-propyl)-amide | NH | =O | 4-Cl-phenyl | 3-tert-butylamino-propyl |
| 54 | 3-(4-Chloro-phenyl)-adamantane-1-carboxylic acid(3-pyrrolidin-1-yl-propyl)-amide | NH | =O | 4-Cl-phenyl | 3-pyrrolidin-1-yl-propyl |
| 55 | 3-(4-Chloro-phenyl)-adamantane-1-carboxylic acid[3-(2-oxo-pyrrolidin-1-yl)-propyl]-amide | NH | =O | 4-Cl-phenyl | 3-(2-oxo-pyrrolidin-1-yl)-propyl |
| 56 | Adamantane-1-carboxylic acid[2-(1-methyl-pyrrolidin-2-yl)-ethyl]-amide | NH | =O | H | 2-(1-methyl-pyrrolidin-2-yl)-ethyl |
| 57 | 3-(4-Chloro-phenyl)-adamantane-1-carboxylic acid[2-(1-methyl-pyrrolidin-2-yl)-ethyl]-amide | NH | =O | 4-Cl-phenyl | 2-(1-methyl-pyrrolidin-2-yl)-ethyl |
| 58 | 3-(4-Chloro-phenyl)-adamantane-1-carboxylic acid(2-morpholin-4-yl-ethyl)-amide | NH | =O | 4-Cl-phenyl | 2-morpholin-4-yl-ethyl |
| 59 | 3-(4-Chloro-phenyl)-adamantane-1-carboxylic acid(2-piperazin-1-yl-ethyl)-amide | NH | =O | 4-Cl-phenyl | 2-piperazin-1-yl-ethyl |
| 60 | Adamantane-1-carboxylic acid(pyridin-4-ylmethyl)-amide | NH | =O | H | pyridin-4-ylmethyl |

-continued

| Cmpd | Chemical name | Y | R3 | R1 | R2 |
|---|---|---|---|---|---|
| 61 | 3-(4-Fluoro-phenyl)-adamantane-1-carboxylic acid(pyridin-4-ylmethyl)-amide | NH | =O | 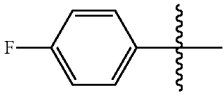 | 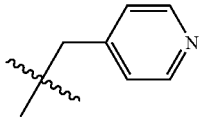 |
| 62 | 3-(4-Chloro-phenyl)-adamantane-1-carboxylic acid(pyridin-4-ylmethyl)-amide | NH | =O | 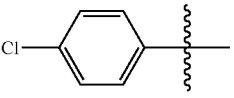 [SMILES: *c1ccc(Cl)cc1] | 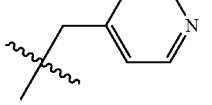 |
| 63 | Adamantane-1-carboxylic acid(pyridin-4-ylmethyl)-amide | NH | =O | H | 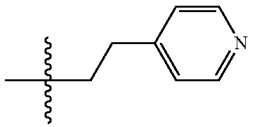 |
| 64 | 3-(4-Chloro-phenyl)-adamantane-1-carboxylic acid(2-pyridin-4-yl-ethyl)-amide | NH | =O | 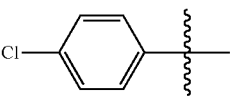 [SMILES: *c1ccc(Cl)cc1] | 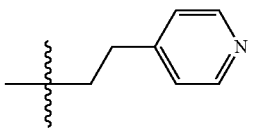 |
| 65 | 3-(4-Chloro-phenyl)-adamantane-1-carboxylic acid(3-imidazol-1-yl-propyl)-amide | NH | =O | 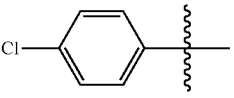 [SMILES: *c1ccc(Cl)cc1] | 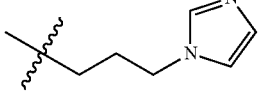 |
| 66 | 3-(4-Chloro-phenyl)-adamantane-1-carboxylic acid(2-methyl-1H-indol-5-yl)-amide | NH | =O | 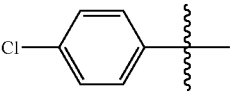 [SMILES: *c1ccc(Cl)cc1] | 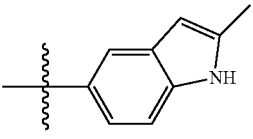 [SMILES: *c1ccc2[nH]c(C)cc2c1] |
| 67 | 3-(4-Chloro-phenyl)-adamantane-1-carboxylic acid(1H-tetrazol-5-yl)-amide | NH | =O | 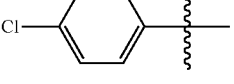 | 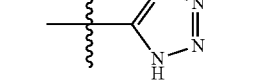 |
| 68 | 3-(4-Chloro-phenyl)-adamantane-1-carboxylic acid(9-ethyl-9H-carbazol-3-yl)-amide | NH | =O | 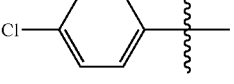 | 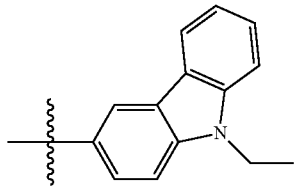 [SMILES: *c1ccc2c(c1)c1ccccc1n2CC] |
| 69 | Adamantane-1-carboxylic acid[4-(4-chloro-phenyl)-thiazol-2-yl]-amide | NH | =O | H | 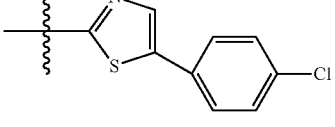 |
| 70 | 3-(4-Chloro-phenyl)-adamantane-1-carboxylic acid[4-(4-chloro-phenyl)-thiazol-2-yl]-amide | NH | =O | 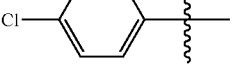 | 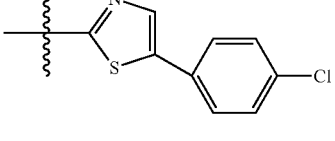 |
| 71 | 3-(4-Chloro-phenyl)-adamantane-1-carboxylic acidbenzothiazol-2-ylamide | NH | =O | 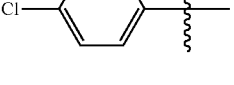 | 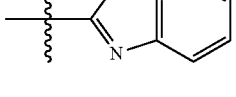 |

-continued

| Cmpd | Chemical name | Y | R3 | R1 | R2 |
|---|---|---|---|---|---|
| 72 | 3-(4-Chloro-phenyl)-adamantane-1-carboxylic acid(5-chloro-benzooxazol-2-yl)-amide | NH | =O | 4-Cl-phenyl | 5-chloro-benzoxazol-2-yl |
| 73 | 3-(4-Chloro-phenyl)-adamantane-1-carboxylic acid(9H-purin-6-yl)-amide | NH | =O | 4-Cl-phenyl | 9H-purin-6-yl |
| 75 | [3-(4-Chloro-phenyl)-adamantan-1-ylmethyl]-isopropyl-amine | NH | H | 4-Cl-phenyl | isopropyl |
| 76 | 4- and -phenol | NH | H | 4-Cl-phenyl | 4-hydroxyphenyl |
| 77 | [3-(4-Chloro-phenyl)-adamantan-1-ylmethyl]-(4-trifluoromethyl-benzyl)-amine | NH | H | 4-Cl-phenyl | 4-trifluoromethyl-benzyl |
| 78 | [3-(4-Chloro-phenyl)-adamantan-1-ylmethyl]-(2-fluoro-4-trifluoromethyl-benzyl)-amine | NH | H | 4-Cl-phenyl | 2-fluoro-4-trifluoromethyl-benzyl |
| 79 | [3-(4-Chloro-phenyl)-adamantan-1-ylmethyl]-(4-fluoro-3-trifluoromethyl-benzyl)-amine | NH | H | 4-Cl-phenyl | 4-fluoro-3-trifluoromethyl-benzyl |
| 80 | [3-(4-Chloro-phenyl)-adamantan-1-ylmethyl]-(4-trifluoromethoxy-benzyl)-amine | NH | H | 4-Cl-phenyl | 4-trifluoromethoxy-benzyl |
| 81 | [3-(4-Chloro-phenyl)-adamantan-1-ylmethyl]-[2-(3-phenoxy-phenyl)-ethyl]-amine | NH | H | 4-Cl-phenyl | 2-(3-phenoxy-phenyl)-ethyl |
| 82 | [3-(4-Chloro-phenyl)-adamantan-1-ylmethyl]-(1-methyl-piperidin-4-yl)-amine | NH | H | 4-Cl-phenyl | 1-methyl-piperidin-4-yl |
| 83 | [3-(4-Chloro-phenyl)-adamantan-1-ylmethyl]-(4-methyl-piperazin-1-yl)-amine | NH | H | 4-Cl-phenyl | 4-methyl-piperazin-1-yl |

-continued

| Cmpd | Chemical name | Y | R3 | R1 | R2 |
|---|---|---|---|---|---|
| 84 | N-tert-Butyl-N'-[3-(4-chloro-phenyl)-adamantan-1-ylmethyl]-propane-1,3-diamine | NH | H | 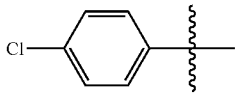 | 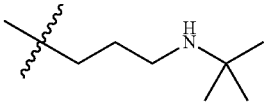 [SMILES: *CCCNC(C)(C)C] |
| 85 | [3-(4-Chloro-phenyl)-adamantan-1-ylmethyl]-(3-pyrrolidin-1-yl-propyl)-amine | NH | H | 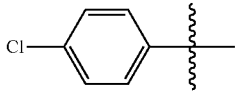 | 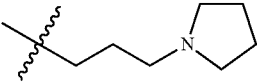 [SMILES: *CCCN1CCCC1] |
| 86 | [3-(4-Chloro-phenyl)-adamantan-1-ylmethyl]-[2-(1-methyl-pyrrolidin-2-yl)-ethyl]-amine | NH | H | 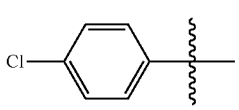 | 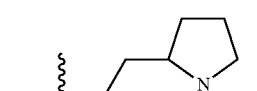 |
| 87 | [3-(4-Chloro-phenyl)-adamantan-1-ylmethyl]-(2-morpholin-4-yl-ethyl)-amine | NH | H | 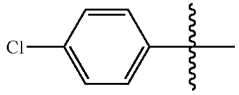 | 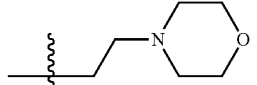 |
| 88 | [3-(4-Chloro-phenyl)-adamantan-1-ylmethyl]-pyridin-4-ylmethyl-amine | NH | H | 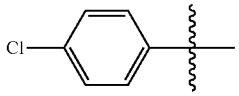 | 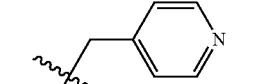 |
| 89 | [3-(4-Chloro-phenyl)-adamantan-1-ylmethyl]-(9-ethyl-9H-carbazol-3-yl)-amine | NH | H | 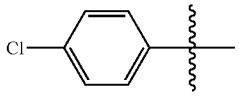 |  |
| 90 | [3-(4-Chloro-phenyl)-adamantan-1-ylmethyl]-[5-(4-chloro-phenyl)-thiazol-2-yl]-amine | NH | H | 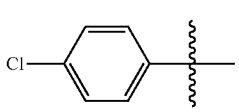 | 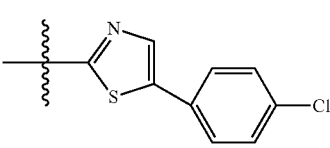 [SMILES: *c1ncc(-c2ccc(Cl)cc2)s1] |
| 91 | 1-[3-(4-Chloro-phenyl)-adamantan-1-yl]-ethylamine | NH | CH3 | 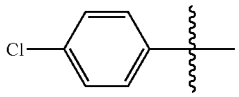 | H |
| 92 | {1-[3-(4-Chloro-phenyl)-adamantan-1-yl]ethyl}-isopropyl-amine | NH | CH3 | 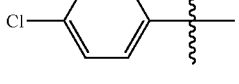 |  |
| 93 | Phenyl-[1-(3-phenyl-adamantan-1-yl)-ethyl]-amine | NH | CH3 | 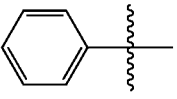 [SMILES: *c1ccccc1] | 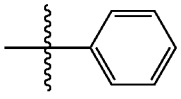 |
| 94 | {1-[3-(4-Fluoro-phenyl)-adamantan-1-yl]-ethyl}-phenyl-amine | NH | CH3 | 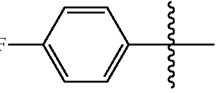 | 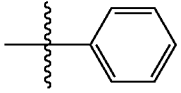 |
| 95 | {1-[3-(4-Chloro-phenyl)-adamantan-1-yl]-ethyl}-phenyl-amine | NH | CH3 | 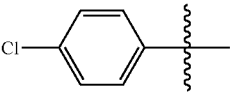 | 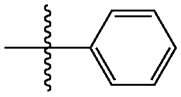 |

-continued

| Cmpd | Chemical name | Y | R3 | R1 | R2 |
|---|---|---|---|---|---|
| 96 | (1-Adamantan-1-yl-ethyl)-benzyl-amine | NH | CH3 | H | 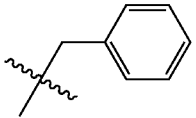 [SMILES: *Cc1ccccc1] |
| 97 | Benzyl-[1-(3-phenyl-adamantan-1-yl)-ethyl]-amine | NH | CH3 | 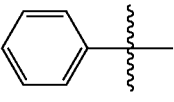 | 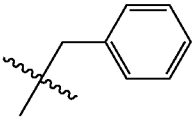 [SMILES: *Cc1ccccc1] |
| 98 | Benzyl-{1-[3-(4-fluoro-phenyl)-adamantan-1-yl]-ethyl}-amine | NH | CH3 | 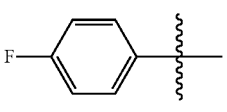 | 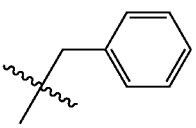 |
| 99 | Benzyl-{1-[3-(4-chloro-phenyl)-adamantan-1-yl]-ethyl}-amine | NH | CH3 | 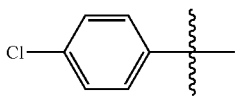 [SMILES: *c1ccc(Cl)cc1] | 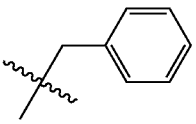 |
| 100 | {1-[3-(4-chloro-phenyl)-adamantan-1-yl]-ethyl}-amine | NH | CH3 | 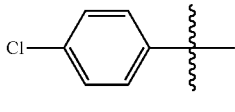 [SMILES: *c1ccc(Cl)cc1] | 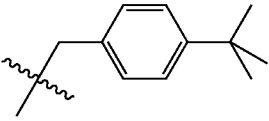 [SMILES: *Cc1ccc(C(C)(C)C)cc1] |
| 101 | [1-(4-Bromo-phenyl)-ethyl]-{1-[3-(4-chloro-phenyl)-adamantan-1-yl]-ethyl}-amine | NH | CH3 | 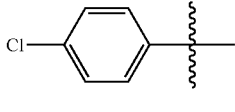 [SMILES: *c1ccc(Cl)cc1] | 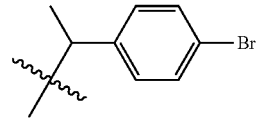 [SMILES: *C(C)c1ccc(Br)cc1] |
| 102 | (1-Adamantan-1-yl-ethyl)-[2-(4-bromo-phenyl)-ethyl]-amine | NH | CH3 | H | 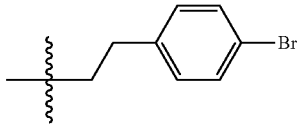 [SMILES: *CCc1ccc(Br)cc1] |
| 103 | [2-(4-Bromo-phenyl)-ethyl]-{1-[3-(4-chloro-phenyl)-adamantan-1-yl]ethyl}-amine | NH | CH3 | 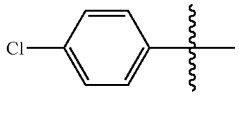 [SMILES: *c1ccc(Cl)cc1] | 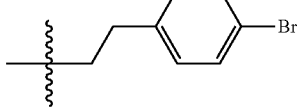 |
| 104 | (1-Adamantan-1-yl-ethyl)-(1-methyl-piperidin-4-yl)-amine | NH | CH3 | H | 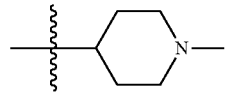 |
| 105 | (1-Methyl-piperidin-4-yl)-[1-(3-phenyl-adamantan-1-yl)-ethyl]-amine | NH | CH3 | 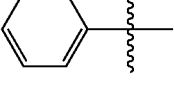 | 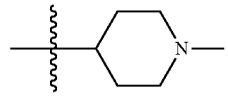 [SMILES: *C1CCN(C)CC1] |
| 106 | {1-[3-(4-Fluoro-phenyl)-adamantan-1-yl]-ethyl}-(1-methyl-piperidin-4-yl)-amine | NH | CH3 | 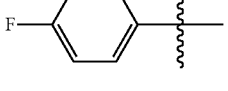 | 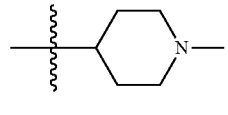 |
| 107 | {1-[3-(4-Chloro-phenyl)-adamantan-1-yl]-ethyl}-(1-methyl-piperidin-4-yl)-amine | NH | CH3 | 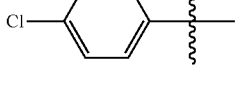 | 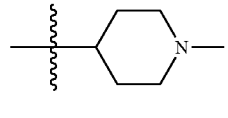 |

-continued

| Cmpd | Chemical name | Y | R3 | R1 | R2 |
|------|---------------|----|----|----|----|
| 108 | {1-[3-(4-Chloro-phenyl)-adamantan-1-yl]-ethyl}-(4-methyl-piperazin-1-yl)-amine | NH | CH3 | 4-chlorophenyl | 4-methylpiperazin-1-yl |
| 109 | {1-[3-(Phenyl)-adamantan-1-yl]-ethyl}-pyridin-4-ylmethyl-amine | NH | CH3 | phenyl | pyridin-4-ylmethyl |
| 110 | {1-[3-(4-Chloro-phenyl)-adamantan-1-yl]-ethyl}-(6-chloro-pyridin-3-ylmethyl)-amine | NH | CH3 | 4-chlorophenyl | (6-chloro-pyridin-3-yl)methyl |
| 111 | {1-[3-(4-Chloro-phenyl)-adamantan-1-yl]-ethyl}-(1-pyridin-4-yl-ethyl)-amine | NH | CH3 | 4-chlorophenyl | 1-(pyridin-4-yl)ethyl |
| 112 | {1-[3-(4-Chloro-phenyl)-adamantan-1-yl]-ethyl}-(3H-imidazol-4-ylmethyl)-amine | NH | CH3 | 4-chlorophenyl | (3H-imidazol-4-yl)methyl |
| 113 | {1-[3-(4-Chloro-phenyl)-adamantan-1-yl]-ethyl}-(2-methyl-1H-indol-5-yl)-amine | NH | CH3 | 4-chlorophenyl | 2-methyl-1H-indol-5-yl |
| 114 | {1-[3-(4-Chloro-phenyl)-adamantan-1-yl]-ethyl}-(9-ethyl-9H-carbazol-3-yl)-amine | NH | CH3 | 4-chlorophenyl | 9-ethyl-9H-carbazol-3-yl |
| 115 | {1-[3-(4-Chloro-phenyl)-adamantan-1-yl]-ethyl}-(9-ethyl-9H-carbazol-3-ylmethyl)-amine | NH | CH3 | 4-chlorophenyl | (9-ethyl-9H-carbazol-3-yl)methyl |
| 116 | 9-Ethyl-9H-carbazol-3-carboxylic acid {1-[3-(4-chloro-phenyl)-adamantan-1-yl]-ethyl}-amide | NH | CH3 | 4-chlorophenyl | 9-ethyl-9H-carbazol-3-yl carbonyl |
| 117 | 1-{1-[3-(4-Chloro-phenyl)-adamantan-1-yl]-ethyl}-3-(4-chloro-3-trifluoromethyl-phenyl)-urea | NH | CH3 | 4-chlorophenyl | C(=O)NH-(4-chloro-3-trifluoromethyl-phenyl) |

-continued

| Cmpd | Chemical name | Y | R3 | R1 | R2 |
|---|---|---|---|---|---|
| 118 | 1-{1-[3-(4-Chloro-phenyl)-adamantan-1-yl]-ethyl}-3-(4-chloro-3-trifluoromethyl-phenyl)-urea | NH | CH3 | 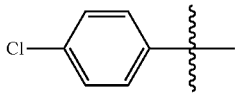 [SMILES: *c1ccc(Cl)cc1] | 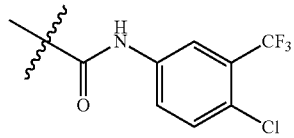 [SMILES: *C(=O)Nc1ccc(Cl)c(C(F)(F)F)c1] |
| 119 | (4-Bromo-thiophen-2-ylmethyl)-{1-[3-(4-chloro-phenyl)-adamantan-1-yl]-ethyl}-amine | NH | CH3 | 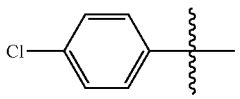 | 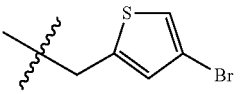 |
| 120 | {1-[3-(4-Chloro-phenyl)-adamantan-1-yl]-ethyl}-(4-phenyl-thiophen-2-ylmethyl)-amine | NH | CH3 | 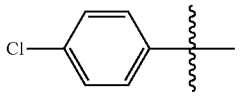 [SMILES: *c1ccc(Cl)cc1] | 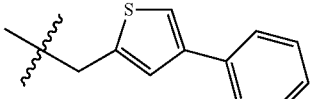 |

Representative formula I-1 compounds include:

| Cmpd | Chemical name | R1 | R2 |
|---|---|---|---|
| 121 | 3-Phenyl-adamantane-1-carboxylicacid | 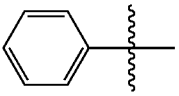 | OH |
| 122 | 3-(4-Fluoro-phenyl)-adamantane-1-carboxylic acid | 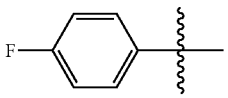 | OH |
| 123 | 3-(4-Chloro-phenyl)-adamantane-1-carboxlic acid | 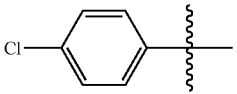 | OH |
| 124 | 1-Adamantan-1-yl-ethanone | H | CH3 |
| 125 | 1-(3-Phenyl-adamantan-1-yl)-ethanone | 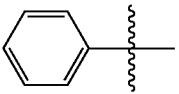 | CH3 |
| 126 | 1-[3-(4-Fluoro-phenyl)-adamantan-1-yl]-ethanone | 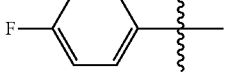 | CH3 |
| 127 | 1-[3-(4-Chloro-phenyl)-adamantan-1-yl]-ethanone | 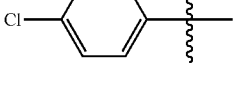 | CH3 |
| 128 | 2-(Adamantane-1-carbonyl)-malonicacid dimethyl ester | H | 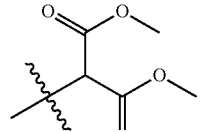 |
| 129 | 2-[3-(4-Chloro-phenyl)-adamantan-1-carbonyl]-malonic acid dimethylester | 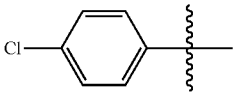 | 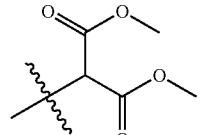 |

-continued

| Cmpd | Chemical name | R1 | R2 |
|---|---|---|---|
| 130 | 3-(4-Chloro-phenyl)-1-[3-(4-chloro-phenyl)-adamantan-1-yl]-propenone | 4-Cl-C6H4- | -CH=CH-C6H4-4-Cl |
| 131 | 4-{3-[3-(4-Chloro-phenyl)-adamantan-1-yl]-3-oxo-propenyl}-benzonitrile | 4-Cl-C6H4- | -CH=CH-C6H4-4-CN |
| 132 | 1-[3-(4-Chloro-phenyl)-adamantan-1-yl]-3-(4-hydroxy-phenyl)-propenone | 4-Cl-C6H4- | -CH=CH-C6H4-4-OH |
| 133 | 1-[3-(4-Chloro-phenyl)-adamantan-1-yl]-3-naphthalen-2-yl-propenone | 4-Cl-C6H4- | -CH=CH-(naphthalen-2-yl) |
| 134 | 1-[3-(4-Chloro-phenyl)-adamantan-1-yl]-3-(6-chloro-pyridin-3-yl)-propenone | 4-Cl-C6H4- | -CH=CH-(6-chloro-pyridin-3-yl) |
| 135 | 1-[3-(4-Chloro-phenyl)-adamantan-1-yl]-3-(1H-imidazol-4-yl)-propenone | 4-Cl-C6H4- | -CH=CH-(1H-imidazol-4-yl) |
| 136 | 1-[3-(4-Chloro-phenyl)-adamantan-1-yl]-3-(9-ethyl-9H-carbazol-3-yl)-propenone | 4-Cl-C6H4- | -CH=CH-(9-ethyl-9H-carbazol-3-yl) |
| 137 | 1-[3-(4-Chloro-phenyl)-adamantan-1-yl]-3-(4-phenyl-thiophen-2-yl)-propenone | 4-Cl-C6H4- | -CH=CH-(4-phenyl-thiophen-2-yl) |

A particularly preferred aryladamantane compound of the present invention is illustrated below and referred to as ABC294640 [3-(4-chlorophenyl)adamantane-1-carboxylicacid (pyridin-4-ylmethyl)amide]:

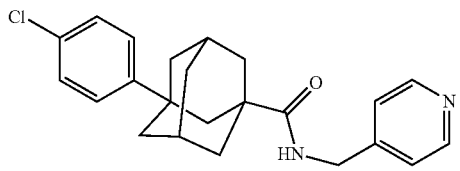

ABC294640

In an embodiment, an aryladamantane compound of the present invention is selected from a compound of Formula 8:

Formula 8

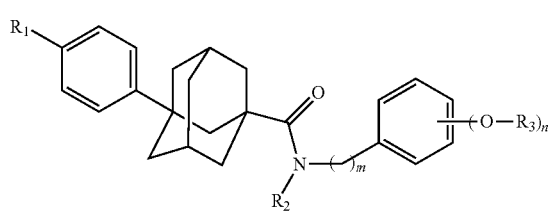

(I)

and pharmaceutically acceptable salts thereof, wherein
R₁ is H, Cl or F;
R₂ is H or alkyl;
m is 0, 1 or 2;
n is 1, 2, 3, 4 or 5;
each R₃ is independently H, —C(O)alkyl, —C(O)CH₂CH₂C(O)OH, R₄, —C(O)NR₅R₆, —P(O)(OR₇)₂ or glucosyl, provided that at least one R₃ is not H, wherein
  R₄ is a natural or unnatural amino acid linked through the carboxyl moiety as an ester,
  R₅ is H or alkyl,
  R₆ is H or alkyl, and
each R₇ is independently H or alkyl.
In certain embodiments of the compounds of formula (I) as described above, the

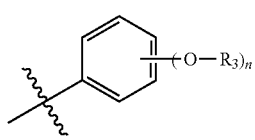

moiety is a catechol with substitution at least one catechol —OH. For example, in one embodiment, the

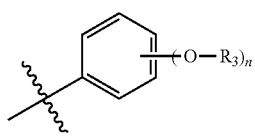

moiety has the structure

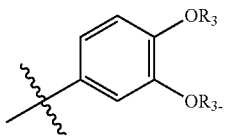

In one particularly preferred embodiment of the compounds of formula (I) as described above, the

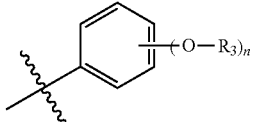

moiety has the structure

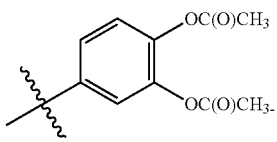

In one especially preferred embodiment of the invention, compounds of formula (I) have R₁=Cl, R₂=H, m=2, n=2, and each R₃=—C(O)alkyl, especially —C(O)CH₃.
For example, compounds of the invention include:
Acetic acid 2-acetoxy-5-(2-{[3-(4-chlorophenyl)-adamantane-1-carbonyl]-amino}ethyl)phenyl ester;
Propionic acid 2-propionyloxy-5-(2-{[3-(4-chlorophenyl)-adamantane-1-carbonyl]-amino}ethyl)phenyl ester;
Butyric acid 2-butyryloxy-5-(2-{[3-(4-chlorophenyl)-adamantane-1-carbonyl]-amino}ethyl)phenyl ester;
Isobutyric acid 5-(2-{[3-(4-chlorophenyl)adamantane-1-carbonyl]amino}ethyl)-2-hydroxyphenyl ester; and
2-Amino-3-methyl-butyric acid 5-(2-{[3-(4-chlorophenyl)adamantane-1-carbonyl]amino}ethyl)-2-hydroxyphenyl ester.

A particularly preferred aryladamantane compound of the present invention is illustrated below and referred to as ABC294735:

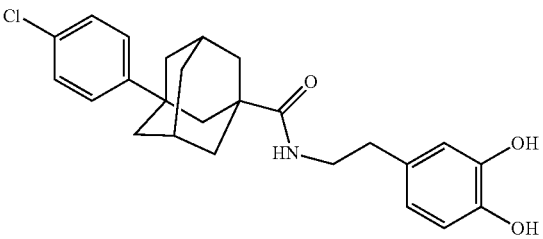

ABC294735

Solid forms for oral administration may contain pharmaceutically acceptable binders, sweeteners, disintegrating agents, diluents, flavorings, coating agents, preservatives, lubricants, and/or time delay agents. Suitable binders include gum acacia, gelatin, corn starch, gum tragacanth, sodium alginate, carboxymethylcellulose or polyethylene glycol (PEG). Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange, or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Solid forms for oral administration may contain pharmaceutically acceptable binders, sweeteners, disintegrating agents, diluents, flavorings, coating agents, preservatives, lubricants, and/or time delay agents. Suitable binders include gum acacia, gelatin, corn starch, gum tragacanth, sodium alginate, carboxymethylcellulose or polyethylene glycol (PEG). Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange, or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Compounds of the invention determined to be effective for the prevention or treatment of disease or disorders in animals, e.g., rodents, dogs, and monkeys, may also be useful in treatment of tumors in humans. Those skilled in the art of treating tumors in humans will know, based upon data obtained in animal studies, the dosage and route of administration of the compounds to humans. In general, the dosage and route of administration in humans is expected to be similar to that in animals.

A method of assessing the efficacy of a treatment in a subject includes determining the pre-treatment extent of a cancer by methods well known in the art (e.g., determining tumor size or screening for cancer markers) and then administering a cancer therapy of the present invention to the subject. After an effective treatment period after the administration of the combination therapy (e.g., 1 day, 1 week, 2 weeks, one month, six months), the extent of the cancer is determined again. In an embodiment, the modulation (e.g., decrease) of the extent of invasiveness of the cancer indicates efficacy of the treatment. The extent or invasiveness of the cancer may be determined periodically throughout treatment. For example, the extent or invasiveness of the cancer may be checked every few hours, days or weeks to assess the further efficacy of the treatment. A decrease in extent or invasiveness of the cancer indicates that the treatment is efficacious.

EXAMPLES

In Vivo Screening of Four Selected Patient-Derived Pancreatic Cancer Xenografts for Sensitivity to a Combination Cancer Therapy of the Present Disclosure Comprising Rifabutin, Clarithromycin, and Clofazimine RHB-104 is a combination drug capsule composed of the three antibiotics: Rifabutin, Clofazimine and Clarithromycin, RedHill Biopharma Ltd, and described above. In this study, the anti-tumor efficacy and tolerability of RHB-104 was screened in vivo in nude mice subcutaneously implanted with four different patient-derived pancreatic cancer tumor xenografts (patient-derived tumor xenografts, PDXs). The four PAXF models were selected based on IL6 and IL8 expression and on sensitivity to the standard-of-care (SoC) compound gemcitabine. The four efficacy experiments were preceded by a dose-finding study in tumor-free mice.

The aim of the efficacy studies was to screen for tumor sensitivity towards treatment with RHB-104 as monotherapy in four different tumor models. The selected tumor models were PAXF 546, PAXF 736, PAXF 1872 and PAXF 199. Each experiment consisted of two groups of three animals receiving oral treatment with RHB-104 or with the vehicle of RHB-104. Treatments were given orally twice daily for two weeks and were followed by a two week observation period. Relative tumor volumes (RTV) for control (C) and treatment (T) mice were calculated. The mean RTV for control and treatment mice for each study were calculated and the minimum T/C value based on RTVs and the vehicle group was used for evaluation of anti-tumor efficacy on the day of min. T/C. At the end of the experiment, tumors were collected and snap-frozen for further analysis. This experiment allowed for the calculation of the tumor growth delay.

Study Design for Dose Finding Experiment

| Group ID | Therapy | Total Daily Dose [mg/kg/day] | Schedule [Dosing days] | Appl. Route | No. of Animals |
|---|---|---|---|---|---|
| 1 | Vehicle | 10 ml/kg/day | 1-21 (h:0) | p.o. | 3 |
| 2 | RHB-104 | 36 | 1-21 (h:0) | p.o. | 3 |
| 3 | RHB-104 | 36/2*36/36 (72 mg/kg/day) | 0(h:12)/1-20(h:0 + 12)/21 (h:0) | p.o. | 3 |
| 4 | RHB-104 | 54/2*54/54 (108 mg/kg/day) | 0(h:12)/1-20(h:0 + 12)/21 (h:0) | p.o. | 3 |

Vehicle for RHB-104: ORA-Plus ®.

Study Design for Efficacy Experiments

| Group ID | Therapy | Total Daily Dose [mg/kg/day] | Schedule [Dosing days] | Appl. Route | No. of Animals |
|---|---|---|---|---|---|
| 1 | Vehicle | 10/2*10/10 ml/kg/day | 0(h:12)/1-13(h:0 + 12)/14 (h:0) | p.o. | 3 |
| 2 | RHB-104 | 36/2*36/36 (72 mg/kg/day) | 0(h:12)/1-13(h:0 + 12)/14 (h:0) | p.o. | 3 |

Vehicle for RHB-104: ORA-Plus ®.

Details of Sample Collection

| Group ID | No. of Animals to be Sampled | Type of Sample, Fixation | Time or Time Frame After Last Treatment | Sample Amount |
|---|---|---|---|---|
| All | All | Tumors, SF | At the end of the observation period | Whole tumor |

ORA-Plus® (an oral suspending vehicle): provided as solution from Perrigo, Habari; shipped and stored at ambient temperature.

RHB-104: provided as pills from Corealis Pharma; shipped at ambient temperature, the pills were crushed with mortar and pestle and the powder was combined and stored at ambient temperature prior to use.

RHB-104 (efficacy study): a dosing solution with a concentration of 3.6 mg/ml, for dosing of RHB-104 at 36 mg/kg/dose, was prepared daily by dissolving 26.27 mg dry matter (corresponding to 8.64 mg API) in 2.4 milliliter ORA-Plus® and stirred (vortexed) at room temperature for 5 minutes followed by sonification until a homogenous suspension was achieved. The dosing solution was stored at ambient temperature, protected from light and used within the same dosing day (vortexed again before second application).

RHB-104 (dose-finding study): a dosing solution with a concentration of 3.6 mg/ml, for dosing of RHB-104 at 36 mg/kg/dose, was prepared daily by dissolving 39.4 mg dry matter (corresponding to 12.96 mg API) in 3.6 milliliter ORA-Plus® and stirred (vortexed) at room temperature for 5 minutes followed by sonification until a homogenous suspension was achieved. The dosing solution was stored at ambient temperature, protected from light and used within the same dosing day (vortexed again before second application).

RHB-104 (dose-finding study): a dosing solution with a concentration of 5.4 mg/ml, for dosing of RHB-104 at 54 mg/kg/dose, was prepared daily by dissolving 39.4 mg dry matter (corresponding to 12.96 mg API) in 2.4 milliliter ORA-Plus® and stirred (vortexed) at room temperature for 5 minutes followed by sonification until a homogenous suspension was achieved. The dosing solution was stored at ambient temperature, protected from light and used within the same dosing day (vortexed again before second application).

All dosing solutions were administered at a dose volume of 10 ml/kg.

Immunodeficient rodents enable the xenotransplantation and growth of human tumors. Subcutaneous tumor implantation is a well-described method allowing visualization and quantification of tumor growth. Usually, female immunodeficient NMRI-Foxn1$^{nu}$ mice are used. Male animals are used only if required by the tumor model (e.g. prostate cancer) or for other scientific reasons. The animals are delivered at the age of four to six weeks and are used for implantation after at least one week of quarantine. Only animals with unobjectionable health are selected to enter testing procedures. Animals used were NMRI nu/nu.

The tumor xenografts were derived from surgical specimens from cancer patients. Following excision at surgery, tumor pieces are subcutaneously implanted into immunodeficient mice and are therefore referred to as patient tumor explants passaged subcutaneously in nude mice or as patient-derived tumor xenografts (PDX). Establishment and characterization of the PDXs is performed following their primary implantation into immunodeficient mice (passage 1). The tumor xenografts are passaged until establishment of a stable growth pattern. At that point, master stocks of early passage PDXs are frozen in liquid nitrogen. Usually, a particular stock batch is only used for a limited number of further passages.

Tumor fragments were obtained from xenografts in serial passage in nude mice. After removal from donor mice, tumors were cut into fragments (3-4 mm edge length) and placed in PBS containing 10% penicillin/streptomycin. Recipient animals were anesthetized by inhalation of isoflurane and received unilateral or bilateral tumor implants subcutaneously in the flank. Tumor xenografts with a take rate <65% (Table 2) were implanted with one or two tumors per mouse and in case of a bilateral take, one of these tumors was explanted prior to randomization.

TABLE 2

Overview of Experiments

| Tumor Designation/ Passage [1] | Number (Gender) of Animals | Tumors Implanted per Animal | Number of Animals | Group Median Tumor Volume [2] |
|---|---|---|---|---|
| — | 12 (female) | 0 | 12 | — |
| PAXF 546/ 8N4 | 12 (female) | 1 | 6 | 133.5-153.5 |
| PAXF 736/ 9N2 | 12 (female) | 1 | 6 | 100.1-102.7 |
| PAXF 1872/ 6N2 | 12 (female) | 1 | 6 | 105.0-107.6 |
| PAXF 1998/ 5N2 | 12 (female) | 1 | 6 | 116.5-120.3 |

[1] The number preceding the N represents the total number of passages and the number following the N represents the passage number after the last freeze/thaw cycle.
[2] Range at randomization [mm³]

Animals and tumor implants were monitored daily until clear signs of beginning solid tumor growth were detectable in a sufficient number of animals. At randomization, the volume of growing tumors was determined. Animals fulfilling the randomization criteria (i.e. bearing tumors of 50-250 mm³, preferably 80-200 mm³) were then distributed into experimental groups, aiming at comparable median and mean group tumor volumes of approximately 100-120 mm³. Animals not randomized are euthanized. The day of randomization is designated as day 0 of an experiment.

The percentage of all tumor implants suitable for randomization at the standard volume is defined as the take rate according to the following equation:

$$\text{Take Rate } [\%] = \frac{\text{number of tumors suitable for randomization}}{\text{total number of implanted fragments}} \times 100$$

A median take rate was calculated for characterization purposes (see Table 3 for the median take rates of the PDXs used in the present study). For the calculation of the number of animals and tumor fragments needed at implantation, the median take rate was taken into account.

The time from implantation to randomization at a standard tumor volume is expressed in days as "Induction time (IT)". A median IT is calculated for characterization purposes (see Table 2 for median ITs of PDXs used in the present study).

TABLE 3

Characteristics of the Human Tumor Xenografts

| Tumor Designation | Histology/ Differentiation | Origin | Stage | Age (Gender) of Patient | TR [%] | IT [Days] | Td [Days] |
|---|---|---|---|---|---|---|---|
| PAXF 546 | adenosquamous carcinoma good | Metastasis | M1 liver, peritoneum | 70 (Male) | 75 | 18 | 6.5 |
| PAXF 736 | adeno carcinoma poor | Recurrent | M1 | 65 (Male) | 77 | 18 | 8.5 |
| PAXF 1872 | adeno carcinoma moderate | Primary | pT1pN1pMx | 39 (Female) | 80 | 20 | 6.1 |
| PAXF 1998 | adeno carcinoma moderate | Primary | pT3pN1pM1 (ADR) | 74 (Male) | 80 | 22 | 5.6 |

TR, take rate; IT, induction time; Td, tumor volume doubling time: typical values (median)

Animals were weighed twice a week, or daily if body weight losses in excess of 15% were recorded. Relative body weights of individual animals were calculated by dividing the individual body weight on Day X ($BW_x$) by the individual body weight on Day 0 ($BW_0$) multiplied by 100%:

$$RBW_x[\%] = \frac{BW_x[g]}{BW_0[g]} \times 100$$

Group median relative body weights were calculated as well, considering only animals that were alive on the day in question.

The absolute tumor volumes (ATVs) were determined by two-dimensional measurement with a caliper on the day of randomization and then twice weekly. Tumor volumes were calculated according to the formula:

$$\text{Tumor volume} = (a \times b^2) \times 0.5$$

where a represents the largest and b the perpendicular tumor diameter of the tumor representing an idealized ellipsoid.

Relative volumes of individual tumors (individual RTVs) for Day x were calculated by dividing the absolute individual tumor volume on Day x ($T_x$) by the absolute individual tumor volume of the same tumor on Day 0 (To) multiplied by 100%:

$$RTV_x[\%] = \frac{T_x \times 100}{T_0}$$

Group median RTV values were used for drawing growth curves and for treatment evaluation for as long as at least 50% of the animals in a group remain alive or a minimum of three animals.

For calculation of the group median tumor volumes the values from animals that were alive on the day in question were considered. In addition, tumor volumes of animals that were euthanized due to their tumor load were carried forward using the Last-Observation-Carried-Forward (LOCF) methodology for as long as this increases the group median tumor volume.

Dosing in the present study was performed as described in Table 4. The first day of dosing is either the day of randomization (day 0, see below) or the following day (day 1, but no later than 24 hours after randomization) as seen in Table 4.

The time of the first dose on a dosing day is designated as h:0. Multiple daily dosages of the same reagent are indicated with the time interval between therapies, e.g. h:0+12. Therapy with other reagents is indicated in relation to the first daily dose, e.g. h:8, where applicable.

TABLE 4

Anti-tumor Efficacy

| Therapy[1] | Dose Level [mg/kg/day] | Schedule [Day] | Route | Minimum T/C [%] (Day)[2] | Efficacy Rating | Td [Days] | Tq [Days] |
|---|---|---|---|---|---|---|---|
| Tumor Model PAXF 546-Exp. Q255 | | | | | | | |
| Vehicle control | 10/2*10/10 ml/kg/day | 0(h:12)/1-13(h:0 + 12)/14 (h:0) | p.o. | n/a | n/a | 5.1 | 18.5 |
| RHB-104 | 36/2*36/36 | 0(h:12)/1-13(h:0 + 12)/14 (h:0) | p.o. | 67.7 (28) | – | 6.4 | 20.8 |
| Tumor Model PAXF 736-Exp. Q256 | | | | | | | |
| Vehicle control | 10/2*10/10 ml/kg/day | 0(h:12)/1-13(h:0 + 12)/14 (h:0) | p.o. | n/a | n/a | 4.5 | 8.6 |
| RHB-104 | 36/2*36/36 | 0(h:12)/1-13(h:0 + 12)/14 (h:0) | p.o. | 71.1 (10) | – | 5.9 | 11.2 |

TABLE 4-continued

Anti-tumor Efficacy

| Therapy[1] | Dose Level [mg/kg/day] | Schedule [Day] | Route | Minimum T/C [%] (Day)[2] | Efficacy Rating | Td [Days] | Tq [Days] |
|---|---|---|---|---|---|---|---|
| Tumor Model PAXF 1872-Exp. Q257 | | | | | | | |
| Vehicle control | 10/2*10/10 ml/kg/day | 0(h:12)/1-13(h:0 + 12)/14 (h:0) | p.o. | n/a | n/a | 3.7 | 8.2 |
| RHB-104 | 36/2*36/36 | 0(h:12)/1-13(h:0 + 12)/14 (h:0) | p.o. | 58.3 (14) | +/− | 6.0 | 10.4 |
| Tumor Model PAXF 1998-Exp. Q258 | | | | | | | |
| Vehicle control | 10/2*10/10 ml/kg/day | 0(h:12)/1-13(h:0 + 12)/14 (h:0) | p.o. | n/a | n/a | 3.5 | 9.3 |
| RHB-104 | 36/2*36/36 | 0(h:12)/1-13(h:0 + 12)/14 (h:0) | p.o. | 86.4 (16) | − | 3.4 | 8.9 | n/a, not applicable; n.r., not reached (i.e. group median RTVs always <200%/400%)
Efficacy rating: ++++, T/C < 5%; +++, T/C 5-<10%; ++, T/C 10-<25%; +, T/C 25-<50%; +/−, T/C: 50-65%; −, T/C ≥ 65%
[1]Vehicle for RHB-104: ORA-Plus ®.
[2]Minimum T/C values are calculated based on median values.

When considerable body weight loss is recorded in efficacy studies the following measures are taken:
no therapy for individual animals with body weight loss >20%
daily body weight measurements of individual animals with body weight loss >15%
facilitated access to feed and water for animals with body weight loss >20%
resumption of dosing when individual animals have regained a relative body weight of at least 85%

Efficacy experiments were generally terminated at the earliest four weeks after the start of dosing, including a standard observation period of two weeks after the end of treatment.

The maximum tolerated dose (MTD) is defined herein as the dose which shall allow uninterrupted treatment of an animal with the respective compound according to the intended schedule, without applying dose adjustments or termination criteria. This definition may also be applied to combination therapy regimens. Dose-finding studies are conducted in tumor-free animals.

The overall survival rate (Table 5) was calculated by counting the number of animals that would have survived beyond the last experimental day of each group and dividing them by the total number of animals in the group. Animals that died or were euthanized on the last day of the group for any other reason than sample collection or termination of the group were not counted as survivors. The adjusted survival rate in Table 6 is calculated by counting all surviving animals including those that were euthanized for tumor-related reasons and dividing them by the total number of animals in the group. The following reasons for euthanasia are classed as tumor-related: 1) tumors fulfilling volume-related termination criteria including accessory tumors and 2) ulcerating tumors. Euthanasia of animals due to symptoms of tumor-induced cachexia is not counted as tumor-related.

TABLE 5

Body Weight Losses and Survival Rates

| Therapy | Dose Level [mg/kg/day] | Schedule [Day] | Last Day of Group | Maximum Median BWL [%] (Day)[1] | Overall Survival Rate [2] |
|---|---|---|---|---|---|
| Vehicle control | 10 ml/kg/day | 0-21 (h:0) | 28 | n.r. | 3/3 (100%) |
| RHB-104 | 36 | 0-21 (h:0) | 28 | 2.4 (1) | 3/3 (100%) |
| RHB-104 | 36/2*36/36 | 0(h:12)/1-20(h:0 + 12)/21 (h:0) | 28 | n.r. | 3/3 (100%) |
| RHB-104 | 54/2*54/54 | 0(h:12)/1-20(h:0 + 12)/21 (h:0) | 28 | n.r. | 3/3 (100%) |

Vehicle for RHB-104: ORA-Plus ®.
[1]Day on which the minimum median body weight was recorded; n.r., not relevant, no body weight loss recorded (i.e. group median RBWs always >100%).
[2] Number of animals that would have survived beyond the last experimental day over total number of animals in the group.
3 Survival rate adjusted for (i.e. not counting) all animals that were euthanized for tumor-related reasons.

TABLE 6

Median Body Weight Losses and Adjusted Survival Rates

| Therapy | Dose Level [mg/kg/day] | Schedule [Day] | Last Day of Group | Maximum Median BWL [%] (Day)[1] | Overall Survival Rate[2] | Euthanasia for Tumor-related Reasons (Day) | Adjusted Survival Rate[3] |
|---|---|---|---|---|---|---|---|
| Tumor Model PAXF 546*-Exp. Q255 | | | | | | | |
| Vehicle control | 10/2*10/10 ml/kg/day | 0(h:12)/1-13(h:0 + 12)/14 (h:0) | 28 | 6.8 (28) | 2/3 (67%) | 1× TV > 2000 mm³ (28) | 100% |
| RHB-104 | 36/2*36/36 | 0(h:12)/1-13(h:0 + 12)/14 (h:0) | 28 | 0.7 (21) | 2/3 (67%) | 1× TV > 2000 mm³ (28) | 100% |
| Tumor Model PAXF 736-Exp Q256 | | | | | | | |
| Vehicle control | 10/2*10/10 ml/kg/day | 0(h:12)/1-13(h:0 + 12)/14 (h:0) | 28 | n.r. | 1/3 (33%) | 2× TV > 2000 mm³ (24,24) | 100% |
| RHB-104 | 36/2*36/36 | 0(h:12)/1-13(h:0 + 12)/14 (h:0) | 28 | n.r. | 2/3 (67%) | 1× TV > 2000 mm³ (21) | 100% |
| Tumor Model PAXF 1872-Exp. Q257 | | | | | | | |
| Vehicle control | 10/2*10/10 ml/kg/day | 0(h:12)/1-13(h:0 + 12)/14 (h:0) | 28 | 1.0 (7) | 1/3 (33%) | 2× TV > 2000 mm³ (21, 21) | 100% |
| RHB-104 | 36/2*36/36 | 0(h:12)/1-13(h:0 + 12)/14 (h:0) | 28 | n.r. | 2/3 (67%) | 1× TV > 2000 mm³ (25) | 100% |
| Tumor Model PAXF 1998-Exp. Q258 | | | | | | | |
| Vehicle control | 10/2*10/10 ml/kg/day | 0(h:12)/1-13(h:0 + 12)/14 (h:0) | 27 | 2.3 (13) | 1/3 (33%) | 2× TV > 2000 mm³ (20, 20) | 100% |
| RHB-104 | 36/2*36/36 | 0(h:12)/1-13(h:0 + 12)/14 (h:0) | 27 | n.r. | 1/3 (33%) | 2× TV > 2000 mm³ (20, 20) | 100% |

Vehicle for RHB-104: ORA-Plus ®.
[1] Day on which the minimum median body weight was recorded; n.r., not relevant, no body weight loss recorded (i.e. group median RBWs always >100%).
[2] Number of animals that would have survived beyond the last experimental day over total number of animals in the group.
[3] Survival rate adjusted for (i.e. not counting) all animals that were euthanized for tumor-related reasons.

Tumor volume doubling/quadruplication time (Td/Tq) for test and control groups is defined as the time interval (in days) required for a group to reach a median RTV of 200%/400%. Data are presented in Table 4.

The test versus control value for a particular day (T/C in %) is calculated from the ratio of the median RTV values of test versus control groups on day x multiplied by 100%.

$$T/C_x[\%] = \frac{\text{median } RTV_x \text{ treated group}}{\text{median } RTV_x \text{ control group}} \times 100$$

The minimum T/C value recorded for a particular test group during an experiment represents the maximum anti-tumor efficacy for the respective treatment. Minimum T/C values are calculated if at least 50% and at least three of the randomized animals in the test and in the control group were alive on the day in question. The minimum T/C values are always calculated without using the LOCF methodology.

Group minimum T/C values are used for efficacy rating as follows:

| | | |
|---|---|---|
| – | Inactive | T/C ≥ 65% |
| +/– | Borderline efficacy | 50% ≤ T/C < 65% |
| + | Moderate efficacy | 25% ≤ T/C < 50% |
| ++ | High efficacy | 10% ≤ T/C < 25% |
| +++ | Very high efficacy | 5% ≤ T/C < 10% |
| ++++ | Complete remission | T/C < 5% |

Statistical significance of the anti-tumor efficacy was evaluated by a non-parametric Kruskal-Wallis test followed by Dunn's posttest. Individual RTVs of test and control groups are compared on days on which the minimum T/C values are achieved in the relevant test groups. Usually, statistical analysis is only carried out if at least 50% of the initially randomized animals (and at least four animals) in a relevant group are still alive, in this study the group size is only three animals at randomization and the result of the statistical evaluation is therefore less reliable than it would be in a study with a larger group size. By convention, p-values ≤0.05 indicate significance of tumor inhibition.

An overview of the experiments is given in Table 3. The results are summarized in Table 4 and in FIGS. 1-5.

Figure 6A:
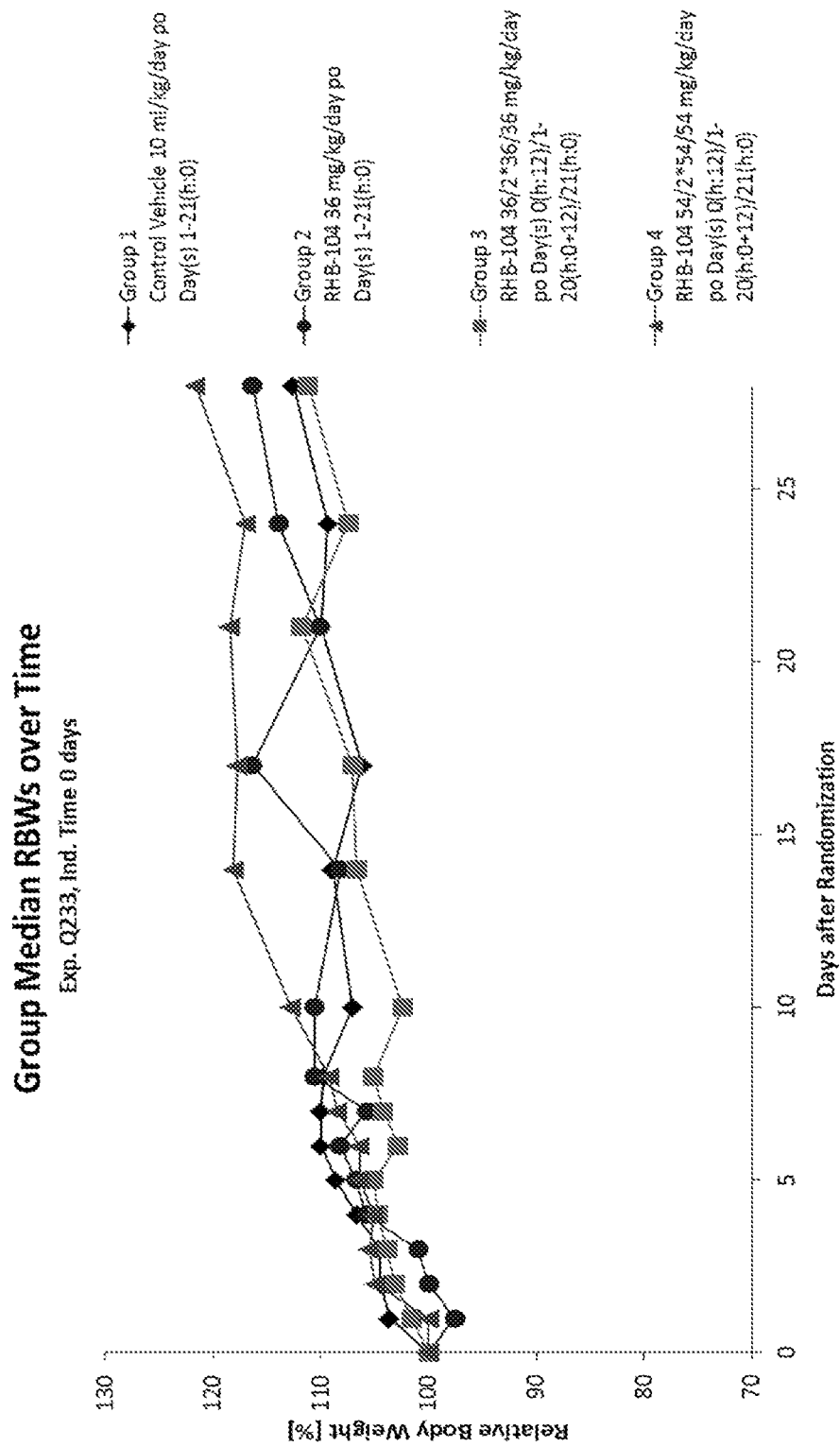
FIGS. 6A-6E show the impact of treatments on body weights of mice. Shown are the group median relative body weights over time of all experiments (FIG. 6A) and group median relative body weights over time for each of the four different patient-derived pancreatic cancer tumor xenografts (FIGS. 6B-6E).
Figure 6B:
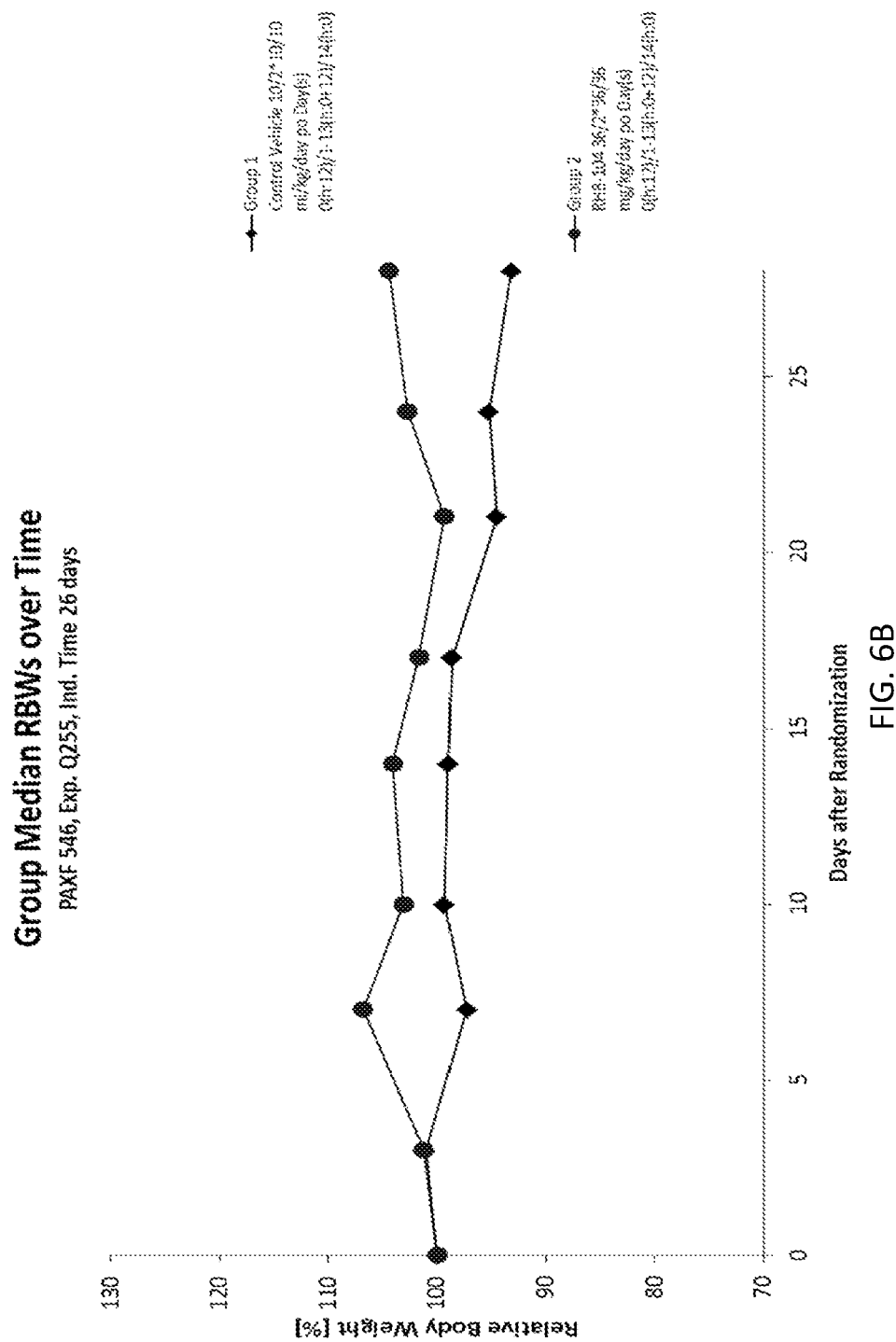
Figure 6C:
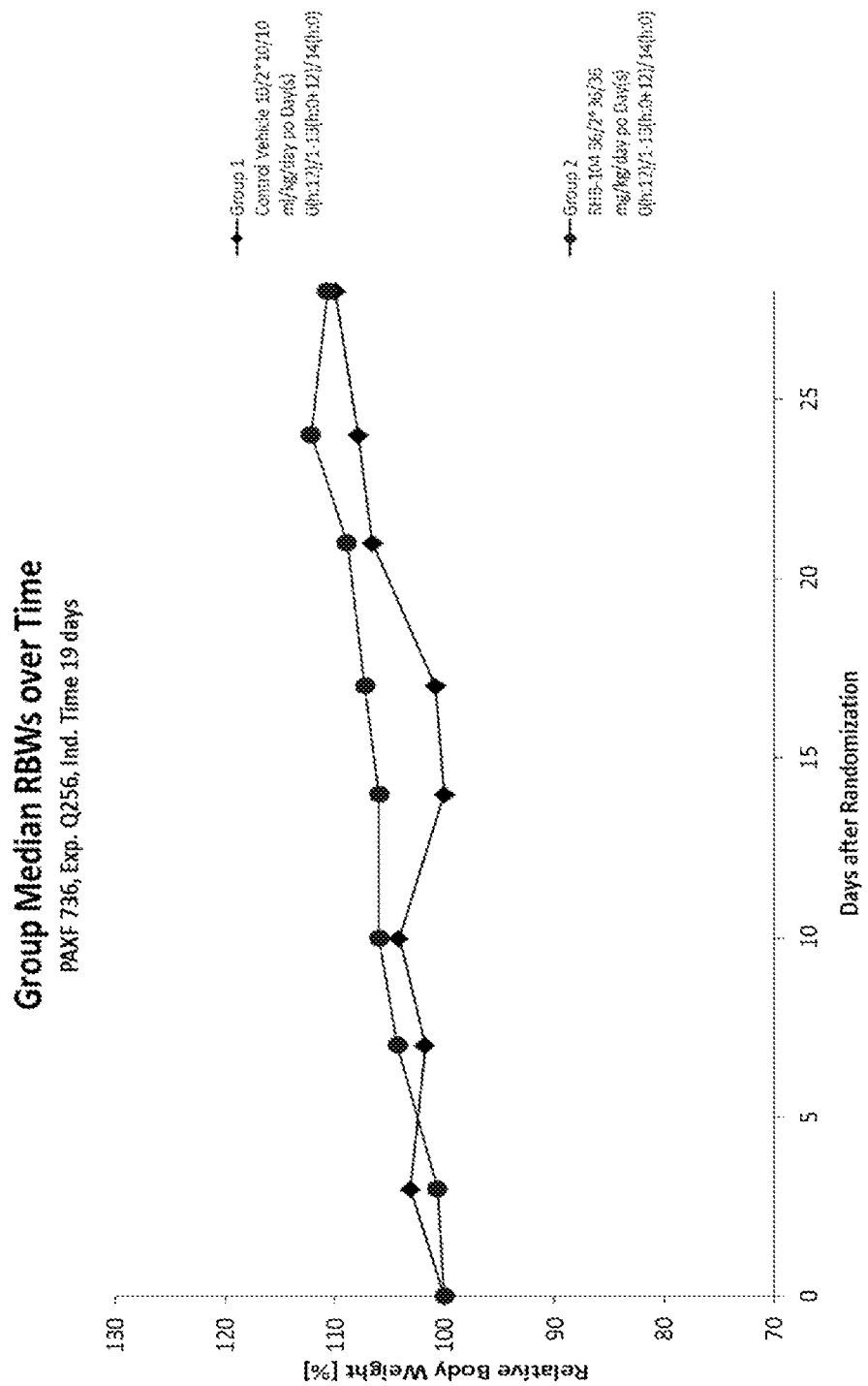
Figure 6D:
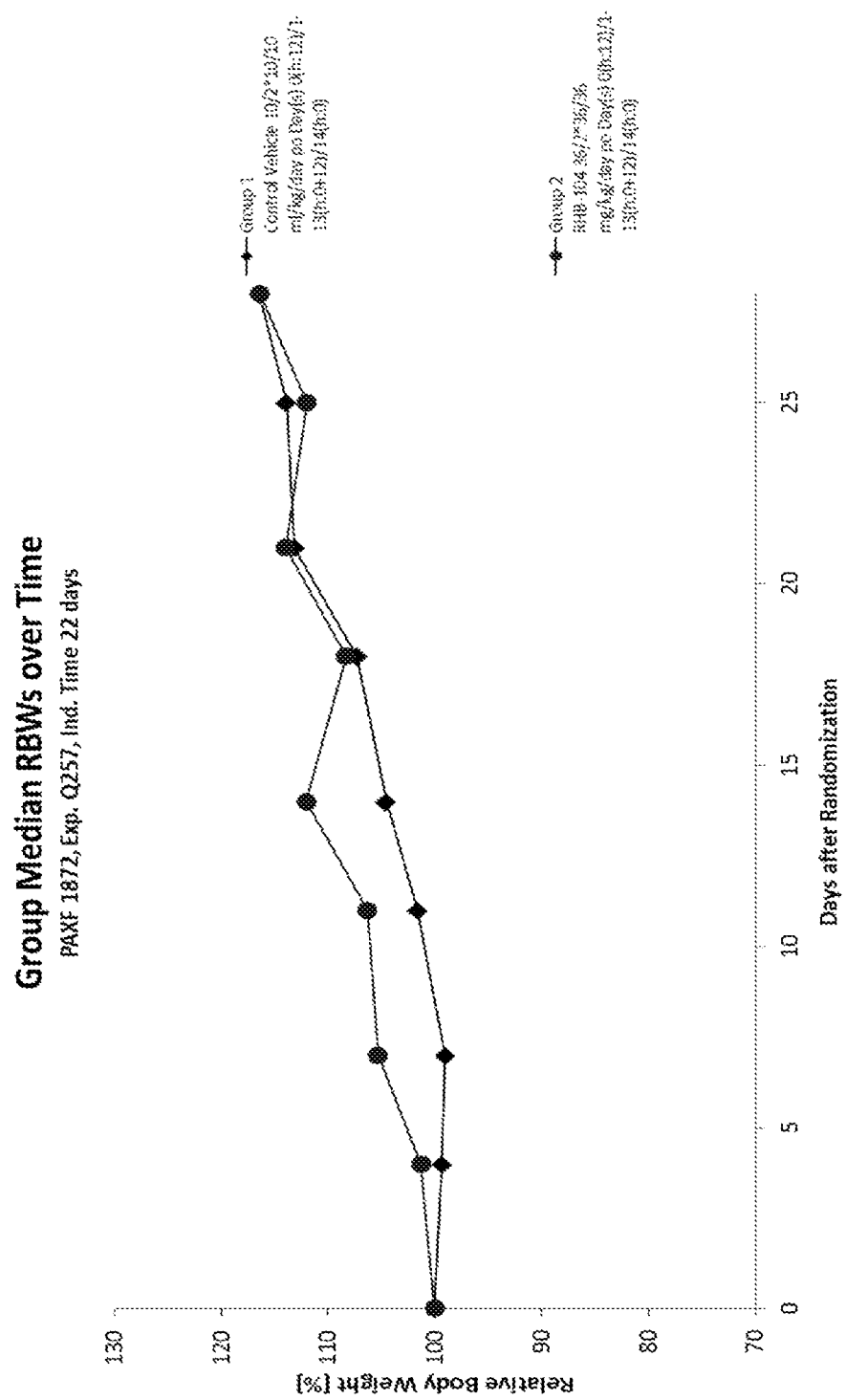
Figure 6E:
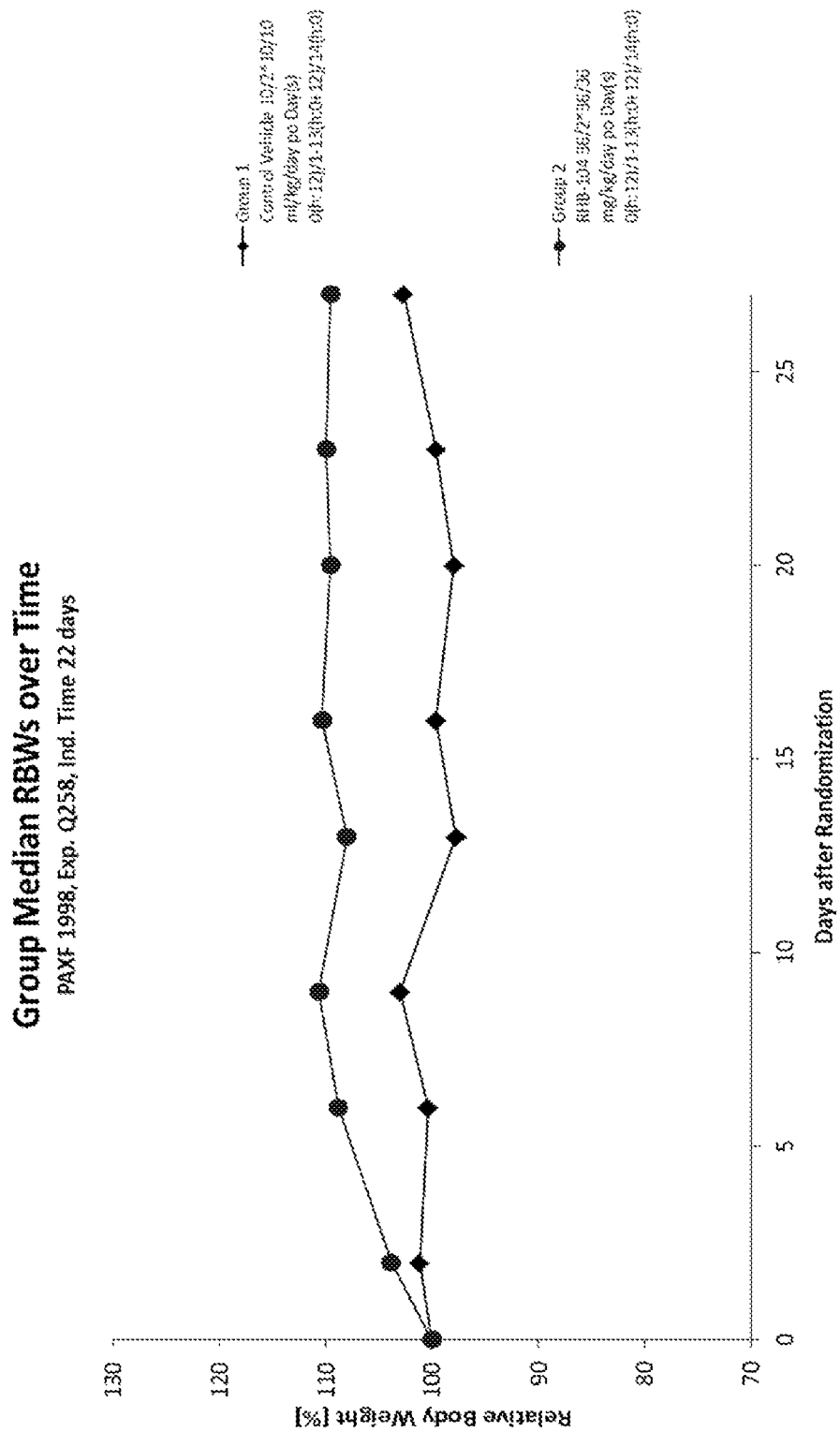

In this study, the anti-tumor efficacy of RHB-104 was assessed in monotherapy in immunodeficient mice implanted subcutaneously with four different pancreatic PDXs. Groups of three mice were administered the compound orally, twice daily, for two weeks followed by an observation period of two weeks. At the end of the experiment tumors from all animals were collected and snap-frozen for further analysis. The anti-tumor efficacy was evaluated as minimum T/C value and was calculated from group median relative tumor volumes (RTVs) in the treatment group compared to a control group that received the vehicle of RHB-104 (ORA-Plus). Statistical significance of tumor growth inhibition was assessed on the day of min. T/C by a Kruskal-Wallis test of the relative tumor volumes followed by Dunn's post test. The efficacy experiments were preceded by a dose-finding study in tumor-free mice, where groups of three mice were treated orally with RHB-104 for three weeks at three different regimens. Either, a dose-level of 36 mg/kg was given once daily, or a dose level of 36 mg/kg or 54 mg/kg was given twice daily. Additionally, one group was treated with ORA-Plus®, the vehicle of RHB-104 (Group 1). As illustrated in FIGS. 6A-6E, RHB-104 was well tolerated in tumor-free mice with regard to body weight losses and survival rates. As seen in FIG. 6A, a minor BWL of 2.4% on day 1 of the study was observed for the group treated once daily at a dose level of 36 mg/kg (Group 2), no BWLs were observed in the other groups and survival rates were 100% in all four groups. Based on these observations, it was decided to dose RHB-104 at a dose level of 36 mg/kg twice daily in the efficacy experiments with tumor-bearing mice.

Highest sensitivity to treatment with RHB-104 was observed in the PAXF 1872 tumor model, where a min. T/C value of 58.3% was reached on the last day of treatment and rated as anti-tumor efficacy. Treatments with RHB-104 in the other three tumor models resulted in min. T/C values of 67.7%, 71.1% and 86.4% for the PAXF 546, PAXF 736 and PAXF 1998 tumor models, respectively.

Table 4 and FIGS. 6A-6E summarize the results in body weight change, survival and observations. Treatments with RHB-104 were well tolerated with BWLs≤0.7% and adjusted survival rates of 100% in all four tumor models. The PAXF 546 tumor model is known to induce cachexia and here a moderate BWL of 6.8% was observed in the vehicle control group.

Treatments with RHB-104 were well tolerated with BWLs≤0.7% and adjusted survival rates of 100% in all four tumor models.

RHB-104 was tested orally at a twice-daily dose level of 36 mg/kg in groups of three mice, anti-tumor efficacy was assessed as minimum T/C value based on group median relative tumor volumes (RTV). Statistical significance was evaluated by a Kruskal Wallis test of RTVs on the day of min. T/C in comparison to a control group receiving the vehicle of RHB-104. The treatment period lasted two weeks in the efficacy experiments and was followed by a two week observation period, whereafter tumors were collected and snap-frozen for further analysis. In the dose-finding experiment the treatment lasted three weeks and was followed by a one week observation period. Good tolerability of RHB-104 was observed in the dose-finding study, where RHB-104 was tested in groups of three mice at three different regimens, additionally, one group of three mice received ORA-Plus®, the vehicle of RHB-104. All four groups displayed BWLs≤2.4% and adjusted survival rates of 100%.

Effects of RHB-104 on LPS-Induced Cytokine Production in C57BL/6 Mice

This study was performed to evaluate the effects of RHB-104 (as detailed above) dosed orally at 108 mg/kg on lipopolysaccharide (LPS)-induced cytokine production in mice. The LPS-induced cytokine production model in mice is commonly used to test the ability of compounds to suppress production of pro-inflammatory cytokines TNF and IL-6 in vivo.

In this model LPS is injected into mice intraperitoneally (i.p.) or intravenously. Two hours after the LPS injection, concentrations of IL-6 and TNF reach peak levels in serum of the injected mice. At that time the concentration of anti-inflammatory cytokine IL-10 is also increased, but the serum concentration of IL-10 peaks approximately 6 hours after the LPS administration.

30 female C57BL/6 mice, 11 weeks old, were dosed once with RHB-104, then injected with LPS 1 hour later. 2 hours after LPS injection, mice were bled and serum was isolated. The concentration of cytokines in serum was measured. Dexamethasone administered at 5 mg/kg i.p. was used as positive control for suppression of the immune response. Dexamethasone suppresses production of pro-inflammatory cytokines TNF and IL-6 increases production of anti-inflammatory cytokine IL-10.

There were 3 groups in the study, according to Table 7 below:

TABLE 7

Study Design

| Group | # mice | Treatment | Dose | Route | Frequency | Volume | Purpose |
|---|---|---|---|---|---|---|---|
| 1 | 10 | Vehicle (Ora-Plus) | — | p.o. | Once | 15 mL/kg | Negative control |
| 2 | 10 | Dexamethasone | 5 mg/kg | i.p. | Once | 10 mL/kg | Positive control |
| 3 | 10 | RHB-104 | 108 mg/kg | p.o. | Once | 15 mL/kg | Test |

Serum concentrations of IL-2, IL-4, IL-6, IL-10, IL-17, IFN-γ and TNF were measured using cytokine bead analysis (CBA) Th1/Th2/Th17 kit (Becton Dickinson). Concentrations of cytokines in serum between groups were compared using 2-tailed Student's t-test.

Serum concentrations of IL-2, IL-4, IL-17 and IFN-γ were below detection level in all groups, as expected for this model. Serum concentrations of IL-6, TNF, and IL-10 are shown in Table 8 below and FIGS. 7, 8 and 9.

TABLE 8

Serum Concentration of Cytokines

| Group | Body weight (g) ± SD | P value | IL-6 (pg/mL) ± SD | P value | TNF (pg/mL) ± SD | P value | IL-10 (pg/mL) ± SD | P value |
|---|---|---|---|---|---|---|---|---|
| 1 | 20.07 ± 0.89 | | 5092 ± 1515 | | 332 ± 148 | | 76 ± 72 | |
| 2 | 20.19 ± 0.84 | 0.7610 | 1259 ± 295 | 0.0000* | 35 ± 10 | 0.0000* | 106 ± 66 | 0.3451 |
| 3 | 20.09 ± 0.96 | 0.9620 | 2618 ± 962 | 0.0004* | 154 ± 62 | 0.0025* | 63 ± 40 | 0.6133 |

$p < 0.05$

Figure 7:
FIG. 7 is a bar graph showing the concentration of IL-6 in mouse serum after administration of vehicle (negative control), dexamethasone (positive control), or RHB-104, followed by an LPS injection, to female C57BL/6 mice.
Figure 8:
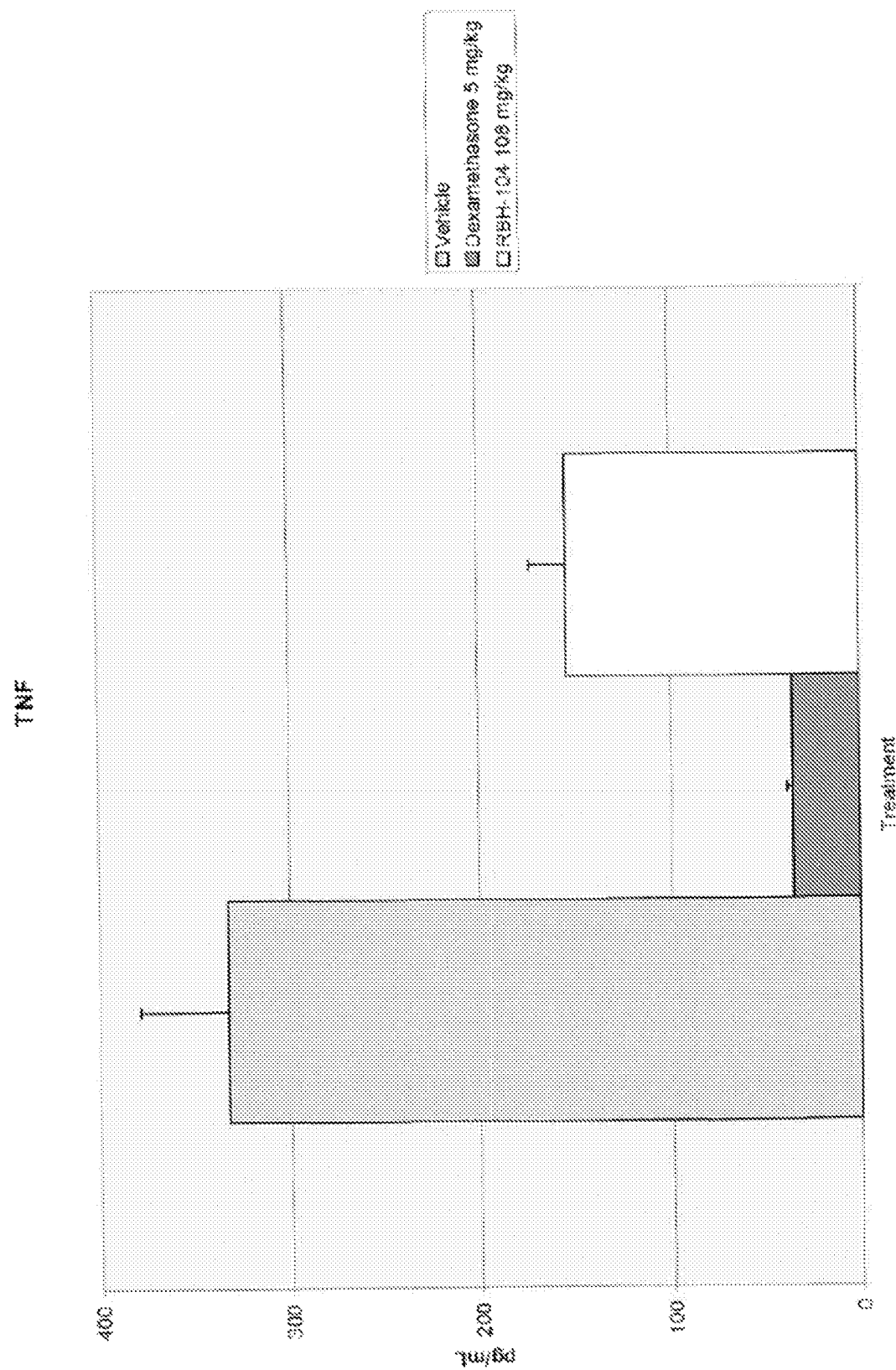
FIG. 8 is a bar graph showing the concentration of TNF in mouse serum after administration of vehicle (negative control), dexamethasone (positive control), or RHB-104, followed by an LPS injection, to female C57BL/6 mice.
Figure 9:
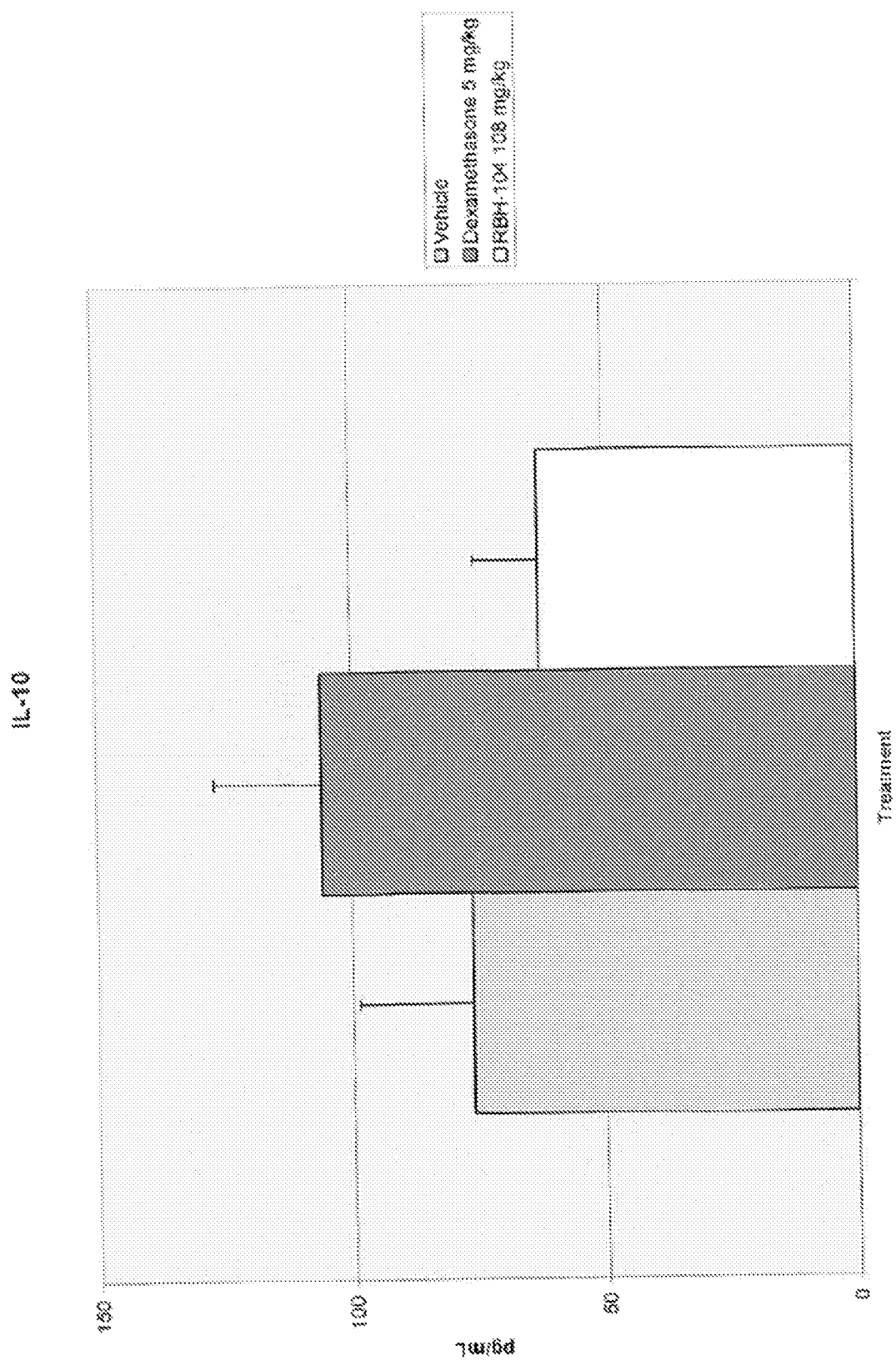
FIG. 9 is a bar graph showing the concentration of IL-10 in mouse serum after administration of vehicle (negative control), dexamethasone (positive control), or RHB-104, followed by an LPS injection, to female C57BL/6 mice.

In the serum of vehicle treated mice, concentrations of IL-6, TNF and IL-10 were as expected for this model (FIGS. 7-9).

In the dexamethasone treated group, serum concentrations or pro-inflammatory cytokines IL-6 and TNF were significantly lower than in the vehicle treated group, as expected (FIGS. 7 and 8). The IL-10 concentration was higher than in the vehicle group, but the difference was not statistically significant (FIG. 9). These results confirm that dexamethasone worked as a positive control.

RHB-104 treated mice had serum concentrations of IL-6 and TNF significantly lower than in the vehicle treated group (FIGS. 7 and 8). The concentration of IL-10 was not significantly different from the vehicle control mice (FIG. 9).

In Vitro Cytotoxicity Assay

The following experiment was performed to assess the potential of combination agents of the present disclosure for their capability of inhibiting the growth or proliferation of pancreatic cancer cells comprising contacting pancreatic cancer cells with effective amounts of the agents, alone and in combination, thereby inhibiting the growth or proliferation of the pancreatic cancer cells.

The present study investigated whether clarithromycin+rifabutin+clofazimine ("Combo") would be synergistic with [3-(4-chlorophenyl)-adamantane-1-carboxylic acid (pyridin-4-ylmethyl)amide] ("ABC2640") against MIA PaCa-2, PANC-1, and Hs 766T pancreatic cancer cell lines. Hs 766T is a cell line derived from the lymph node metastasis of a 64-year-old male with pancreas carcinoma. MIA PaCa-2 is a cell line derived from the pancreas adenocarcinoma of a 65-year-old man who presented with abdominal pain for 6 months and a palpable upper abdominal mass. PANC-1 was cultured from a 56-year-old male with an adenocarcinoma in the head of the pancreas which invaded the duodenal wall.

The MTT assay is commonly used to determine cytotoxicity of potential medicinal agents, since these types of materials are expected to stimulate or inhibit cell viability and growth. Briefly, 3,000 cells were plated/well-100 μl/well. After overnight, prior to the assay, 50 μl supernatant was removed from each well. Each drug was added at 4× of the final concentration (in 50 μl). Total volume of each well was 200 μl. 4 wells had been used as a control and contained no cells at all. The plate was developed after being incubated for 3 days at 37° C. 20 μl of Promega Substrate Cell Titer 96 Aqueous One Solution Reagent was added to each well, incubated at 37° C. and read OD at 490 nm. The MTT test is based on the enzymatic reduction of the tetrazolium salt MTT [3-(4,5-dimethylthiazol-2-yl)-2,5-diphenyl-tetrazoliumbromide+++] in living, metabolically active cells but not in dead cells. The reaction is carried out in situ in multiwell plates, and the reaction product, a purple-colored formazan soluble in dimethylsulfoxide, is measured colorimetrically, using a multiwell plate reader.

| Results for Hs 766T | | |
|---|---|---|
| Agent | Concentration (μM) | Toxicity (%) |
| clarithromycin | 100 | 29 |
| rifabutin | 70 | 20 |
| Clofazimine | 5 | 62 |
| Combo | above | 59 |
| ABC640 | 25 | 17 |
| ABC640 | 50 | 72 |
| UK-1 | 5 | 35 |
| UK-1 | 10 | 28 |
| UK-1 | 20 | 19 |
| Combo + $ABC_{25}$ | above | 96 |
| Combo + $ABC_{50}$ | above | 95 |
| Combo + $UK-1_5$ | above | 81 |
| Combo + $UK-1_{10}$ | above | 93 |
| Combo + $UK-1_{20}$ | above | 96 |
| Combo + $UK-1_{10}$ + $ABC_{25}$ | above | 96 |
| Combo + $UK-1_{10}$ + $ABC_{50}$ | above | 95 |

| Results for MIA PaCa-2 | | |
|---|---|---|
| Agent | Concentration (μM) | Toxicity (%) |
| clarithromycin | 100 | 0 |
| rifabutin | 35 | 8 |
| Clofazimine | 5 | 4 |
| Combo | above | 64 |
| ABC640 | 25 | 11 |
| ABC640 | 50 | 92 |
| UK-1 | 5 | 33 |
| UK-1 | 10 | 0 |
| UK-1 | 20 | 0 |
| Combo + $ABC_{25}$ | above | 96 |
| Combo + $ABC_{50}$ | above | 96 |
| Combo + $UK-1_5$ | above | 95 |
| Combo + $UK-1_{10}$ | above | 97 |
| Combo + $UK-1_{20}$ | above | 97 |
| Combo + $UK-1_{10}$ + $ABC_{25}$ | above | 96 |
| Combo + $UK-1_{10}$ + $ABC_{50}$ | above | 97 |

| Results for PANC-1 | | |
|---|---|---|
| Agent | Concentration (μM) | Toxicity (%) |
| clarithromycin | 100 | 7 |
| rifabutin | 70 | 0 |
| Clofazimine | 5 | 41 |
| Combo | above | 79 |
| ABC640 | 25 | 0 |
| ABC640 | 50 | 68 |
| UK-1 | 5 | 0 |
| UK-1 | 10 | 0 |
| UK-1 | 20 | 14 |
| Combo + $ABC_{25}$ | above | 86 |
| Combo + $ABC_{50}$ | above | 96 |
| Combo + $UK-1_5$ | above | 70 |
| Combo + $UK-1_{10}$ | above | 80 |
| Combo + $UK-1_{20}$ | above | 97 |
| Combo + $UK-1_{10}$ + $ABC_{25}$ | above | 94 |
| Combo + $UK-1_{10}$ + $ABC_{50}$ | above | 92 |

The inventors found additive to synergistic antitumor interactions of the agents tested in all three cell lines by MTT assays. Combination therapy using these agents may enhance the response rate of different cancers to these drugs and may significantly reduce side effects by permitting a lower therapeutic dose to be administered. These novel combinations synergistically decrease cancer cell growth without increasing the toxicity profile compared to the individual drugs.

In Vivo Assay of the uPA Inhibitor Prodrug WX-671 with Regard to Tumor Spreading, Tumor Growth and Metastasizing in Rats

Breast Cancer Model

Fragments of 10-25 mm³ of the BN472 breast cancer (Kort et al., J. Natl. Cancer Inst 72, 709-713, 1984) from a donor animal were implanted underneath the fatty body of a mammary gland of groups (n=15 per group) of female brown Norwegian rats aged 7-8 weeks. The treatments started 72 h after tumor implantation and were repeated daily until the animals were sacrificed after 30 days. The control group (A) received 0.75 ml of the substance-free substance carrier solution consisting of 5% ethanol, 5% D-mannitol and 5% Tween 20 in water orally by gavage. The treatment groups (B and C) received, orally by gavage, either 1 mg/kg (group B) or 5 mg/kg (group C) WX-671 in a volume of 0.75 ml of substance carrier solution. The comparative group D received 1 mg/kg WX-UK1 dissolved in 5% D-mannitol by intraperitoneal injection.

Growth of the inoculated tumors was determined in the dimensions length and width twice weekly, using a slide gauge. After the animals had been sacrificed, the therapy end points, tumor weight, weights of the axillary and intraperitoneal lymph nodes and also the number of macroscopic lung metastases were determined.

In all experiments, treatment with WX-671 achieved a considerable reduction in the size and, respectively, the weight of the tumors and in the number and, respectively, mass of metastases, in comparison with the control group. In the mammary tumor model, the average tumor weights at the end of the treatment were reduced in the WX-671-treated group by more than 66% (p.o.) compared to the control, while an i.p. treatment with the comparative inhibitor substance WX-UK1 achieved only a reduction by approx. 5%. The number of lung foci in the inhibitor prodrug-treated groups was reduced by more than 42% (p.o.) and the average weights of the axillary lymph nodes by more than 63% (p.o.).

The development of bodyweight increase and the comparison of organ weights between inhibitor-treated and vehicle-treated groups gave no indication of a possible considerable toxicity of the inhibitor under the conditions described.

Prophetic Example—In Vivo Assay of the SK2 Inhibitor ABC294640 and the uPA Inhibitor Prodrug WX-671 with Regard to Tumor Spreading, Tumor Growth and Metastasizing in Rats Breast Cancer Model Fragments of 10-25 mm$^3$ of the BN472 breast cancer (Kort et al., J. Natl. Cancer Inst 72, 709-713, 1984) from a donor animal are implanted underneath the fatty body of a mammary gland of groups (n=15 per group) of female brown Norwegian rats aged 7-8 weeks. The treatments start 72 h after tumor implantation and are repeated daily until the animals are sacrificed after 30 days. The control group (A) receives 0.75 ml of the substance-free substance carrier solution consisting of 5% ethanol, 5% D-mannitol and 5% Tween 20 in water orally by gavage. The treatment groups (B and C) receive, orally by gavage, either 50 mg/kg (group B) or 100 mg/kg (group C) ABC294640 in a volume of 0.75 ml of substance carrier solution. The treatment groups (D and E) receive, orally by gavage, either 1 mg/kg (group D) or 5 mg/kg (group E) WX-671 in a volume of 0.75 ml of substance carrier solution. The treatment groups (F and G) receive, orally by gavage, 1 mg/kg WX-671 in a volume of 0.75 ml of substance carrier solution along with 50 mg/kg ABC294640 (group F) or 5 mg/kg WX-671 in a volume of 0.75 ml of substance carrier solution along with 100 mg/kg ABC294640 (group G).

Growth of the inoculated tumors is determined in the dimensions length and width twice weekly, using a slide gauge. After the animals are sacrificed, the therapy end points, tumor weight, weights of the axillary and intraperitoneal lymph nodes and also the number of macroscopic lung metastases are determined.

It is believed that treatment with the combination of WX-671 and ABC294640 will achieve a considerable reduction in the size and, respectively, the weight of the tumors and in the number and, respectively, mass of metastases, in comparison with the treatment groups receiving either agent alone. In some embodiments, the combination therapy result in a reduction of about 10% or more, about 20% or more, about 30% or more, about 40% or more, about 50% or more, about 60% or more, about 70% or more, about 80% or more, about 90% or more, about 95% or more, about 99% or more reduction in the size and, respectively, the weight of the tumors and in the number and, respectively, mass of metastases, in comparison with the treatment groups receiving either agent alone.

Prophetic Example—In Vivo Assay of the uPA Inhibitor Prodrug WX-671 and Clarithromycin with Regard to Tumor Spreading, Tumor Growth and Metastasizing in Rats Breast Cancer Model Fragments of 10-25 mm$^3$ of the BN472 breast cancer (Kort et al., J. Natl. Cancer Inst 72, 709-713, 1984) from a donor animal are implanted underneath the fatty body of a mammary gland of groups (n=15 per group) of female brown Norwegian rats aged 7-8 weeks. The treatments start 72 h after tumor implantation and are repeated daily until the animals are sacrificed after 30 days. The control group (A) receives 0.75 ml of the substance-free substance carrier solution consisting of 5% ethanol, 5% D-mannitol and 5% Tween 20 in water orally by gavage. The treatment groups (B and C) receive, orally by gavage, either 1 mg/kg (group B) or 5 mg/kg (group C) WX-671 in a volume of 0.75 ml of substance carrier solution. The treatment groups (D and E) receive, orally by gavage, either 10 mg/kg/day (group D) or 50 mg/kg/day (group E) CAM. The treatment groups (F and G) receive, orally by gavage, 1 mg/kg WX-671 in a volume of 0.75 ml of substance carrier solution along with 10 mg/kg/day CAM (group F) or 5 mg/kg WX-671 in a volume of 0.75 ml of substance carrier solution along with 50 mg/kg/day CAM (group G).

Growth of the inoculated tumors is determined in the dimensions length and width twice weekly, using a slide gauge. After the animals are sacrificed, the therapy end points, tumor weight, weights of the axillary and intraperitoneal lymph nodes and also the number of macroscopic lung metastases are determined.

It is believed that treatment with the combination of WX-671 and CAM achieve a considerable reduction in the size and, respectively, the weight of the tumors and in the number and, respectively, mass of metastases, in comparison with the treatment groups receiving either agent alone.

In some embodiments, the combination therapy result in a reduction of about 10% or more, about 20% or more, about 30% or more, about 40% or more, about 50% or more, about 60% or more, about 70% or more, about 80% or more, about 90% or more, about 95% or more, about 99% or more reduction in the size and, respectively, the weight of the tumors and in the number and, respectively, mass of metastases, in comparison with the treatment groups receiving either agent alone.

Prophetic Example—In Vivo Assay of the SK2 Inhibitor ABC294640 and Clarithromycin with Regard to Tumor Spreading, Tumor Growth and Metastasizing in Rats Breast Cancer Model Fragments of 10-25 mm$^3$ of the BN472 breast cancer (Kort et al., J. Natl. Cancer Inst 72, 709-713, 1984) from a donor animal are implanted underneath the fatty body of a mammary gland of groups (n=15 per group) of female brown Norwegian rats aged 7-8 weeks. The treatments start 72 h after tumor implantation and are repeated daily until the animals are sacrificed after 30 days. The control group (A) receives 0.75 ml of the substance-free substance carrier solution consisting of 5% ethanol, 5% D-mannitol and 5% Tween 20 in water orally by gavage. The treatment groups (B and C) receive, orally by gavage, either 50 mg/kg (group B) or 100 mg/kg (group C) ABC294640 in a volume of 0.75 ml of substance carrier solution. The treatment groups (D and E) receive, orally by gavage, either 10 mg/kg/day (group D) or 50 mg/kg/day (group E) CAM. The treatment groups (F and G) receive, orally by gavage, 50 mg/kg ABC294640 along with 10 mg/kg/day CAM (group F) or 100 mg/kg ABC294640 along with 50 mg/kg/day CAM (group G).

Growth of the inoculated tumors is determined in the dimensions length and width twice weekly, using a slide gauge. After the animals are sacrificed, the therapy end points, tumor weight, weights of the axillary and intraperitoneal lymph nodes and also the number of macroscopic lung metastases are determined.

It is believed that treatment with the combination of ABC294640 and CAM will achieve a considerable reduction in the size and, respectively, the weight of the tumors and in the number and, respectively, mass of metastases, in comparison with the treatment groups receiving either agent alone.

In some embodiments, the combination therapy result in a reduction of about 10% or more, about 20% or more, about 30% or more, about 40% or more, about 50% or more, about 60% or more, about 70% or more, about 80% or more, about 90% or more, about 95% or more, about 99% or more reduction in the size and, respectively, the weight of the tumors and in the number and, respectively, mass of metastases, in comparison with the treatment groups receiving either agent alone.

In Vivo Test of the Effectiveness of WX-671 in the Colon Carcinoma Model CC531

The anti-tumor efficacy of WX-671 was demonstrated using the transplantable rat colon carcinoma CC531. Six to seven week old female animals (n=18 per group, body weight range 100-130 g received from day 3 after tumor inoculation onwards 0.03, 0.3 or 3.0 mg/kg of WX-671. Control animals received the vehicle (5% ethanol, 5% Tween2o, 5% D-mannitol in water). Seven weeks after tumor implantation the animals were killed and evaluated with respect to primary tumor weight and metastatic endpoints.

The final median tumor weight in treatment groups versus vehicle group was unchanged in the group receiving WX-671 at 0.03 mg/kg, reduced non-significantly by 6% in the group receiving WX-671 at 0.3 mg/kg and significantly (p=0.015) reduced by 15% in the group treated with 3 mg/kg. The difference between terminal tumor sizes in the 0.3 mg/kg groups and the 3.0 mg/kg group was not significant, however. Regarding metastatic endpoints the median number of macroscopic lung foci was significantly reduced (P<0.0001) by 37%, 64% and 57% relative to control in the treatment groups receiving 0.03, 0.3 and 3.0 mg/kg, respectively. The median intraperitoneal lymph node weights were reduced by 31%, 41% and 46% relative to control in the three treatment groups, the latter two reductions being statistically significant (P<0.001).

A highly significant reduction of the number of macroscopic lung foci was apparent in all treatment groups with the lowest dose (0.03 mg/kg, reduction by 37%) being the least efficacious. At 0.3 mg/kg the effect was maximum (reduction by 64%) and was not improved (reduction by 57%) in the group receiving WX-671 at the ten-fold dose i.e. 3.0 mg/kg. A similar pattern was apparent regarding the weights of intraperitoneal lymph nodes. Median weight reductions were achieved by 31% at 0.03 mg/kg (non-significant) and 41% and 46% at the medium and high dose level, respectively.

In Vivo Test of the Effectiveness of WX-671 in the Pancreatic Adenocarcinoma Model CA20948

The anti-tumor efficacy of WX-671 was assayed in a metastatic rat pancreatic tumor model, CA20948. Groups of eighteen rats were inoculated with tumor by intraperitoneal injection of a tumor cell suspension, prepared from a solid tumor harvested from a donor rat.

In this model the intraperitoneally grafted cells migrate to the pancreas to form a pancreatic tumor intimately associated with the pancreas. Within 3 weeks the tumor disseminates typically to the liver to form metastatic lesions which can be counted. Treatments at dose levels of 0.03, 0.3 and 3.0 mg/kg once daily were orally applied daily from day 3 onwards. One group received vehicle as a control and one group received 0.3 mg/kg of WX-UK1 by intraperitoneal injection.

The table below lists the respective percentage reduction of median tumor endpoints relative to control. All treatment schedules had a highly significant effect on the final intraperitoneally grafted tumor plus pancreas mass and on the number of macroscopic liver foci compared with control. Reduction of liver metastasis seemed to be dose dependent.

To assess whether the treatments would have influence not only on liver foci counts but also on the growth rate of metastatic lesions, the relative abundance of large metastases (>2 mm) in the various groups was assessed. The percentage of large liver foci was determined by dividing the number of large lesions by the number of total lesion detected on the livers. Results are listed in the Table below. In the vehicle group the percentage of large metastases was 30.7% whereas in the treatment groups the percentage of large liver lesions was uniformly smaller. This indicates that the treatments with WX-671 (and WX-UK1) not only reduced the number of liver foci but may have also had an inhibitory activity on the growth rate of the metastatic lesions.

Percentage of the number of large (>2 mm) metastatic liver lesion of the total number of liver lesions in the various treatment groups.

| CA20948 pancreatic tumor | percentage large mets |
|---|---|
| Vehicle control | 30.7% |
| WX-671 0.03 mg/kg | 12.4% |
| WX-671 0.3 mg/kg | 16.2% |
| WX-671 3.0 mg/kg | 20.4% |
| WX-UK1 0.3 mg/kg | 13.4% |

The anti-tumor efficacy of intraperitoneal WX-UK1 at 0.3 mg/kg was similar as the efficacy of oral WX-671 at the same dose or higher.

Cytotoxicity Profile of ABC294640

To assess the biological efficacy of ABC294640 in intact cells, ABC294640 was evaluated for cytotoxicity using human cancer cell lines. These experiments followed methods that have been extensively used. Cell lines tested included MCF-7 human breast adenocarcinoma cells and MCF-10A non-transformed human breast epithelial cells. The indicated cell lines were treated with varying doses of ABC294640 for 48 h. Cell survival was then determined using the SRB binding assay (Skehan et al., 1990, J Natl Cancer Inst 82: 1107), and the concentration of ABC294640 that inhibited proliferation by 50% (the $IC_{50}$) was calculated. In MCF-7 human breast adenocarcinoma cells, the $IC_{50}$ was 17 µM (represents the mean±sd for replicate trials). In MCF-10A non-transformed human breast epithelial cells, the $IC_{50}$ was 21 µM (represents the mean±sd for replicate trials). ABC294640 is antiproliferative at sub-to-low-micromolar. The transformed MCF-7 cells were significantly more sensitive than were the non-transformed MCF-10A cells. This indicates that ABC294640 will inhibit the growth of tumor cells without inducing toxicity to normal cells within the patient. Overall, the data demonstrated that ABC294640 is able to enter intact cells and prevent their proliferation.

Survey of Anticancer Activity of ABC294640

The data provided above demonstrates the ability of ABC294640 to inhibit the proliferation of human breast carcinoma cells. To examine the range of anticancer, the chemotherapeutic potency of ABC294640 towards a panel of varied human tumor cell lines representing several major tumor types were determined. The data are described below, and demonstrate that ABC294640 has anticancer activity against a wide variety of cancers.

Potencies of SK inhibitors toward human tumor cell lines.

| Cell Line | Tissue | $IC_{50}$ (µM) Compound 62 |
| --- | --- | --- |
| 1025LU | melanoma | 33.7 ± 2.7 |
| A-498 | kidney | 12.2 ± 6.0 |
| Caco-2 | colon | 11.8 ± 5.6 |
| DU145 | prostate | 21.9 ± 1.5 |
| Hep-G2 | liver | 6.0 ± 2.6 |
| HT-29 | colon | 48.1 ± 7.6 |
| MCF-7 | breast, ER+ | 18.4 ± 7.4 |
| MDA-MB-231 | breast, ER− | 29.1 ± 11.1 |
| Panc-1 | pancreas | 32.8 ± 0.1 |
| SK-OV-3 | ovary | 10.5 ± 2.6 |
| T24 | bladder | 39.4 ± 7.4 |

Sparsely plated cells were treated with an SK inhibitor for 48 hours, and cell viability was determined using sulforhodamine B staining and compared to vehicle-(DMSO) treated cells.

Values are the mean sd for at least three separate experiments.

In Vivo Toxicity of ABC294640

ABC294640 was found to be soluble to at least 15 mg/ml (~30-40 mM) in DMSO:PBS for intraperitoneal (IP) administration or PEG400 for oral dosing. Acute toxicity studies using IP dosing demonstrated no immediate or delayed toxicity in female Swiss-Webster mice treated with up to at least 50 mg/kg of ABC294640. Repeated injections in the same mice every other day over 15 days showed similar lack of toxicity. ABC294640 could also be administered orally to mice at doses up to at least 100 mg/kg without noticeable toxicity.

Antitumor Activity of ABC294640

The antitumor activity of ABC294640 was evaluated using a syngeneic tumor model that uses the mouse JC mammary adenocarcinoma cell line growing subcutaneously in immunocompetent Balb/c mice (Lee et al., 2003, Oncol Res 14: 49). These cells express elevated levels of SK activity relative to non-transformed cells, as well as the multidrug resistance phenotype due to P-glycoprotein activity.

Balb/c mice, 6-8 weeks old, were injected subcutaneously with $10^6$ JC cells suspended in phosphate-buffered saline. ABC294640 was dissolved in PEG400 and administered to mice every-other day at a dose of 100 mg/kg. Body weights and tumor volumes were monitored daily. Tumor growth in animals treated with ABC294640 was significantly lower (>70% decreased at day 16) than tumor growth in control animals. ABC294640 inhibited tumor growth relative to controls by 69%. Dose-response studies with ABC294640 demonstrated that the compound has antitumor activity when orally administered at doses of 35 mg/kg or higher.

Prevention of the Formation of "Multi-Drug Resistance" (MDR) in Human and Animal Tumor Cells to Treatment with Cytostatic Agents by Simultaneous Administration of BVDU The human tumor cell strain K562-WT and the tumor cell strain F46-WT of the mouse (WT=wild type=sensitive to cytostatic treatment=no amplification of the MDR-gene) is treated over several weeks with staged increase in concentrations of adriamycin. During the treatment the cells acquire a resistance to this treatment. With non-resistant cells, 20 ng/ml adriamycin at a treatment time of 4 days has a severely toxic effect—the cells after long term treatment with staged increase in concentration become totally insensitive to 20 ng/ml adriamycin. The formation of resistance is based on the amplification of the MDR gene. In parallel experiments with adriamycin with either 0.5 or 1 µg/ml BVDU given together (BVDU acts in human tumor cells only from about 10 µg/ml in a toxic manner, and in mouse cells from about 8 µg/ml, BVDU prevents the formation of resistance to adriamycin. The tumor cells remain sensitive to the cytostatic treatment and die off. The effect of BVDU is so intense that the treatment must be interrupted by rest stages (growth without substances), so that the experiment extends over 6 to 8 weeks.

BVDU+adriamycin treatment leads to a considerably weaker amplification of the MDR gene than adriamycin treatment alone. At the end of the treatment, there remain only cells which have acquired at least a certain resistance to the adriamycin treatment. The cells which have remained non-resistant as a result of the BVDU treatment have already previously died off.

As the formation of resistance to cytostatic treatment in human tumors is likewise based on the amplification of the MDR gene, the combination of BVDU with an optional cytostatic agent offers the possibility of carrying out therapy at low doses and over longer periods of time than previously.

Prevention of the Formation of "Multi-Drug-Resistance" (MDR) in Tumor Cells to Cytostatic Treatment by Simultaneous Administration of Anti-Recombinogenic BVDU The tumor cell strain F4-6-WT of the mouse (WT=wild type=sensitive to cytostatic treatment=no amplification of the MDR gene) is treated over several weeks with staged increases in concentration of adriamycin. During the treatment the cells acquire a resistance to this treatment. Whereas 20 ng/ml of adriamycin at a treatment time of 4 days has an extremely toxic effect on non-resistant cells, the cells after a long term treatment with staged increases in concentration become totally insensitive to 20 ng/ml adriamycin. The formation of resistance is based on the amplification of the MDR gene. The levels of β-actin MRNA are likewise analyzed as comparison. β-actin is used as an internal control for the RNA quantity.

In parallel experiments, adriamycin is administered with 1 μg/ml of BVDU, and prevented the formation of resistance to adriamycin. The tumor cells remain sensitive to the cytostatic treatment and die off. The effect of BVDU is so intense that the treatment has to be interrupted by rest phases (growth without substances), so that the experiment extends over 6 to 8 weeks.

BVDU Treatment Increases the Sensitivity of AH13r Sarcoma Cells to Chemotherapy-Induced Apoptosis. This Effect is Maintained Even after Discontinuation of the Cytostatic in the so-Called Recovery Phase AH13r cells were subjected to increasing doses of the cytostatic mitomycin C (MMC). BVDU, given alone, showed no toxic effect. MMC+BVDU treatment led, after three treatment cycles, to reduction in the cell number in comparison to treatment with MMC alone. This inhibitory effect was maintained even after discontinuation of the cytostatic in the next cycle, in the so-called recovery phase. The cells without MMC and BVDU continued to grow without inhibition. However, those which continued to receive BVDU were greatly inhibited in their growth. Corresponding results were achieved with methotrexate (MTX), doxorubicin (DOX) and mitoxantrone (MXA). The indication that the reduction in cell number is based on apoptosis, was detected by means of Hoechst 33258/propidium iodide (Hopi) double colouration.

Prophetic Example: Screening Compounds of the Invention to Determine Effects on Cell Cycle and Cell Viability The aim of this study is to determine the effect of agents of the present invention on cell cycle and cell viability in human cancer cell lines. Human cancer cell lines are treated with each agent individually at various concentrations for 48, 72 and 96 hours. Cell viability is monitored using a technique known in the art. For example, cell viability can be assessed using the CellTiter-Blue® Cell Viability Assay (#G8081, Promega, Mannheim, Germany), which provides a homogeneous, fluorescence-based method for monitoring cell viability. The cell cycle can be analysed using flow cytometry, and apoptotic cells can be identified by terminal deoxynucleotidyl transferase-mediated dUTP nick labelling (TUNEL) and by DAPI.

Prophetic Example: Screening Compounds of the Invention to Determine Effects on Cytokine Production In this experiment, the levels of a broad panel of cytokines, including at least some of IL-6, IL-8, IL-10, IL-12, IL-17, IL-23, and TNFα, are monitored in the human cancer cell line supernatants using commercially available ELISA kits. More particularly, it is ascertained whether any of the human cancer cell lines show a downregulation in their ability to produce cytokines after being incubated with agents of the present invention at various concentrations.

Novel strategies for the treatment of cancer patients based on a combination of drugs are disclosed herein.

A combination of a 5' substituted nucleoside and at least one antibiotic for use in the treatment of cancer, wherein (a) the 5' substituted nucleoside is administered to a patient in one or more doses to establish a therapeutically effective plasma level for a period of at least one week, (b) the antibiotic is administered to a patient in one or more doses to establish a therapeutically effective plasma level for a period of at least one week, and (c) the periods of a) and b) overlap. In an embodiment, the 5' substituted nucleoside is brivudine. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a 5' substituted nucleoside and clofazimine, wherein (a) the 5' substituted nucleoside is administered to a patient in one or more doses to establish a therapeutically effective plasma level for a period of at least one week, (b) the clofazimine is administered to a patient in one or more doses to establish a therapeutically effective plasma level for a period of at least one week, and (c) the periods of a) and b) overlap. In an embodiment, the 5' substituted nucleoside is brivudine. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a 5' substituted nucleoside, clofazimine, and at least one antibiotic for use in the treatment of cancer, wherein (a) the 5' substituted nucleoside is administered to a patient in one or more doses to establish a therapeutically effective plasma level for a period of at least one week, (b) the clofazimine is administered to a patient in one or more doses to establish a therapeutically effective plasma level for a period of at least one week, (c) the antibiotic is administered to a patient in one or more doses to establish a therapeutically effective plasma level for a period of at least one week, and (d) the periods of a), b) and c) overlap. In an embodiment, the 5' substituted nucleoside is brivudine. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a 5' substituted nucleoside, a sphingosine kinase inhibitor, and at least one antibiotic for use in the treatment of cancer, wherein (a) the 5' substituted nucleoside is administered to a patient in one or more doses to establish a therapeutically effective plasma level for a period of at least one week, (b) the sphingosine kinase inhibitor is administered to a patient in one or more doses to establish a therapeutically effective plasma level for a period of at least one week, (c) the antibiotic is administered to a patient in one or more doses to establish a therapeutically effective plasma level for a period of at least one week, and (d) the periods of a), b) and c) overlap. In an embodiment, the 5' substituted nucleoside is brivudine. In an embodiment, the sphingosine kinase inhibitor is ABC294640. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a 5' substituted nucleoside, a sphingosine kinase inhibitor, a urokinase inhibitor, and at least one antibiotic for use in the treatment of cancer, wherein (a) the 5' substituted nucleoside is administered to a patient in one or more doses to establish a therapeutically effective plasma level for a period of at least one week, (b) the sphingosine kinase inhibitor is administered to a patient in one or more doses to establish a therapeutically effective plasma level for a period of at least one week, (c) the urokinase inhibitor is administered to a patient in one or more doses to establish a therapeutically effective plasma level for a period of at least one week, (d) the antibiotic is administered to a patient in one or more doses to establish a therapeutically effective plasma level for a period of at least one week, and (e) said periods of a), b), c) and d) overlap. In an embodiment, the 5' substituted nucleoside is brivudine. In an embodiment, the sphingosine kinase inhibitor is ABC294640. In an embodiment, the urokinase inhibitor is upamostat. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a sphingosine kinase inhibitor and at least one antibiotic for use in the treatment of cancer, wherein (a) the sphingosine kinase inhibitor is administered to a patient in one or more doses to establish a therapeutically effective plasma level for a period of at least one week, and (b) the antibiotic is administered to a patient in one or more doses to establish a therapeutically effective plasma level for a period of at least one week, and (c) said periods of a) and b) overlap. In an embodiment, the sphingosine kinase inhibitor is ABC294640. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a urokinase inhibitor and at least one antibiotic for use in the treatment of cancer, wherein (a) the sphingosine kinase inhibitor is administered to a patient in one or more doses to establish a therapeutically effective plasma level for a period of at least one week, and (b) the antibiotic is administered to a patient in one or more doses to establish a therapeutically effective plasma level for a period of at least one week, and (c) said periods of a) and b) overlap. In an embodiment, the urokinase inhibitor is upamostat. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a sphingosine kinase inhibitor, clofazimine, and at least one antibiotic for use in the treatment of cancer, wherein (a) the sphingosine kinase inhibitor is administered to a patient in one or more doses to establish a therapeutically effective plasma level for a period of at least one week, (b) the clofazimine is administered to a patient in one or more doses to establish a therapeutically effective plasma level for a period of at least one week, (c) the at least one antibiotic is administered to a patient in one or more doses to establish a therapeutically effective plasma level for a period of at least one week, and (d) the periods of a), b) and c) overlap. In an embodiment, the sphingosine kinase inhibitor is ABC294640. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a sphingosine kinase inhibitor and clofazimine, wherein (a) the sphingosine kinase inhibitor is administered to a patient in one or more doses to establish a therapeutically effective plasma level for a period of at least one week, (b) the clofazimine is administered to a patient in one or more doses to establish a therapeutically effective plasma level for a period of at least one week, and (c) the periods of a) and b) overlap. In an embodiment, the sphingosine kinase inhibitor is ABC294640. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a sphingosine kinase inhibitor, a urokinase inhibitor, and at least one antibiotic for use in the treatment of cancer, wherein (a) the sphingosine kinase inhibitor is administered to a patient in one or more doses to establish a therapeutically effective plasma level for a period of at least one week, (b) the urokinase inhibitor is administered to a patient in one or more doses to establish a therapeutically effective plasma level for a period of at least one week, (c) the antibiotic is administered to a patient in one or more doses to establish a therapeutically effective plasma level for a period of at least one week, and (d) said periods of a), b) and c) overlap. In an embodiment, the sphingosine kinase inhibitor is ABC294640. In an embodiment, the urokinase inhibitor is upamostat. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a urokinase inhibitor and clofazimine for use in the treatment of cancer, wherein (a) the urokinase inhibitor is administered to a patient in one or more doses to establish a therapeutically effective plasma level for a period of at least one week, and (b) the clofazimine is administered to a patient in one or more doses to establish a therapeutically effective plasma level for a period of at least one week, and (c) said periods of a) and b) overlap. In an embodiment, the urokinase inhibitor is upamostat.

A combination of a urokinase inhibitor, at least one antibiotic, and clofazimine for use in the treatment of cancer, wherein (a) the urokinase inhibitor is administered to a patient in one or more doses to establish a therapeutically effective plasma level for a period of at least one week, (b) the at least one antibiotic is administered to a patient in one or more doses to establish a therapeutically effective plasma level for a period of at least one week, (c) the clofazimine is administered to a patient in one or more doses to establish a therapeutically effective plasma level for a period of at least one week, and (d) said periods of a), b) and c) overlap. In an embodiment, the urokinase inhibitor is upamostat. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

A combination of a urokinase inhibitor and at least one antibiotic for use in the treatment of cancer, wherein (a) the sphingosine kinase inhibitor is administered to a patient in one or more doses to establish a therapeutically effective plasma level for a period of at least one week, and (b) the antibiotic is administered to a patient in one or more doses to establish a therapeutically effective plasma level for a period of at least one week, and (c) said periods of a) and b) overlap. In an embodiment, the urokinase inhibitor is upamostat. In an embodiment, the at least one antibiotic is selected from one of a bactericidal or macrolide antibiotic. In an embodiment, the bactericidal antibiotic is rifabutin. In an embodiment, the macrolide antibiotic is clarithromycin. In an embodiment, the composition further comprises clofazimine. In an embodiment, the composition further comprises at least one anticancer agent selected from the group consisting of chemotherapeutical agents, cytotoxic agents, cytostatic agents, immunotoxic agents and radiotherapy.

What is claimed is:

1. A combination comprising:
    a first compound, wherein the first compound is 3-(4-chlorophenyl)-adamantane-1-carboxylic acid (pyridine-4-ylmethyl)-amide or a pharmaceutical acceptable salt thereof; and
    (ii) a second compound, wherein the second compound is N-α-(2,4,6-triisopropylphenylsulfonyl)-3-hydroxy-amidino-phenylalanine-4-ethoxycarbonylpiperazide, a stereoisomer, a racemic mixture, a metabolite, a salt, crystal, or any combination thereof.

2. The combination of claim 1, wherein the second compound is present as a sulfate or a hydrogen sulfate salt.

3. The combination of claim 1, wherein the second compound is selected from the group consisting of:
    N-α-(2,4,6-triisopropylphenylsulfonyl)-3-hydroxyamidino-(L)phenylalanine-4 ethoxycarbonylpiperazide,
    N-α-(2,4,6-triisopropylphenylsulfonyl)-3-hydroxyamidino-(D)phenylalanine-4-ethoxycarbonylpiperazide, and
    N-α-(2,4,6-triisopropylphenylsulfonyl)-3-hydroxyamidino-(D,L)phenylalanine-4-ethoxycarbonylpiperazide, or a physiologically compatible salt thereof.

4. The combination of claim 1, wherein the second compound is N-α-(2,4,6-triisopropylphenylsulfonyl)-3-hydroxyamidino-(L)phenylalanine-4-ethoxycarbonylpiperazide hydrogen sulfate.

5. The combination of claim 1, wherein the second compound is a crystalline form of N-α-(2,4,6-triisopropylphenylsulfonyl)-3-hydroxyamidino-(L)phenylalanine-4-ethoxycarbonylpiperazide or a physiologically compatible salt thereof.

6. The combination of claim 1, wherein the first compound and the second compound are formulated for oral administration to a subject.

7. The combination of claim 1 further comprising a chemotherapeutic agent.

8. The combination of claim 1 further comprising a radiation therapy agent.

9. The combination of claim 1 further comprising an immunomodulator.

10. The combination of claim 1 further comprising an immune checkpoint inhibitor.

11. The combination of claim 1 further comprising a matrix metalloproteinase inhibitor.

12. A pharmaceutical composition comprising (i) a first pharmaceutical composition, wherein the first pharmaceutical composition comprises a first compound, wherein the first compound is 3-(4-chlorophenyl)-adamantane-1-carboxylic acid (pyridine-4-ylmethyl)-amide or a pharmaceutical acceptable salt thereof; and (ii) a second pharmaceutical composition, wherein the second pharmaceutical composition comprises a second compound, wherein the second compound is N-α-(2,4,6-triisopropylphenylsulfonyl)-3-hydroxyamidino-phenylalanine-4-ethoxycarbonylpiperazide, a stereoisomer, a racemic mixture, a metabolite, a salt, crystal, or any combination thereof.

13. The pharmaceutical composition of claim 12, wherein the first pharmaceutical composition includes a pharmaceutically acceptable excipient and wherein the second pharmaceutical composition includes a pharmaceutically acceptable excipient.

14. The pharmaceutical composition of claim 12, wherein the second compound is present as a sulfate or a hydrogen sulfate salt.

15. The pharmaceutical composition of claim 12, wherein the second compound is selected from the group consisting of:
- N-α-(2,4,6-triisopropylphenylsulfonyl)-3-hydroxyamidino-(L)phenylalanine-4 ethoxycarbonylpiperazide,
- N-α-(2,4,6-triisopropylphenylsulfonyl)-3-hydroxyamidino-(D)phenylalanine-4-ethoxycarbonylpiperazide, and
- N-α-(2,4,6-triisopropylphenylsulfonyl)-3-hydroxyamidino-(D,L)phenylalanine-4-ethoxycarbonylpiperazide, or a physiologically compatible salt thereof.

16. The pharmaceutical composition of claim 12, wherein the second compound is N-α-(2,4,6-triisopropylphenylsulfonyl)-3-hydroxyamidino-(L)phenylalanine-4-ethoxycarbonylpiperazide hydrogen sulfate.

17. The pharmaceutical composition of claim 12, wherein the second compound is a crystalline form of N-α-(2,4,6-triisopropylphenylsulfonyl)-3-hydroxyamidino-(L)phenylalanine-4-ethoxycarbonylpiperazide or a physiologically compatible salt thereof.

18. The pharmaceutical composition of claim 12, further comprising a chemotherapeutic agent, a radiation therapy agent, an immunomodulator, an immune checkpoint inhibitor, a matrix metalloproteinase inhibitor or combinations thereof.

19. The pharmaceutical composition of claim 12, wherein the pharmaceutical composition is formulated for oral administration to a subject.

* * * * *